United States Patent
Lustenberger et al.

(10) Patent No.: US 7,205,294 B2
(45) Date of Patent: Apr. 17, 2007

(54) SELECTED CGRP-ANTAGONISTS PROCESS FOR PREPARING THEM AND THEIR USE AS PHARMACEUTICAL COMPOSITIONS

(75) Inventors: Philipp Lustenberger, Warthausen (DE); Klaus Rudolf, Warthausen (DE); Stephan Georg Mueller, Warthausen (DE); Dirk Stenkamp, Biberach (DE); Henri Doods, Warthausen (DE); Kirsten Arndt, Biberach (DE); Gerhard Schaenzle, Biberach-Mettenberg (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/073,341

(22) Filed: Mar. 3, 2005

(65) Prior Publication Data

US 2005/0227968 A1 Oct. 13, 2005

(30) Foreign Application Priority Data

Mar. 3, 2004 (DE) .................. 10 2004 010 254
Jun. 15, 2004 (DE) .................. 10 2004 028 751

(51) Int. Cl.
*C07D 243/10* (2006.01)
*C07D 401/00* (2006.01)
*C07D 421/00* (2006.01)
*A61K 31/55* (2006.01)
*A61P 25/06* (2006.01)

(52) U.S. Cl. .............. 514/221; 514/252.13; 514/316; 514/318; 514/319; 514/320; 514/321; 514/322; 540/500; 544/360; 546/187

(58) Field of Classification Search ............ 540/500; 544/360; 546/187; 514/221, 252.13, 316, 514/318, 319, 320, 321, 322

See application file for complete search history.

(56) References Cited

U.S. PATENT DOCUMENTS

2004/0063735 A1   4/2004   Chaturvedula et al.
2004/0076587 A1   4/2004   Kruss et al.
2004/0192729 A1   9/2004   Rudolf et al.
2004/0204397 A1   10/2004  Chaturvedula et al.

FOREIGN PATENT DOCUMENTS

WO   WO 03/104236 A1   12/2003
WO   WO 2004/000289 A2  12/2003
WO   WO 2004/063171 A1   7/2004

OTHER PUBLICATIONS

CAS abstract of US 2004/0204397 and US 2004/0063735. 2004.*
Mallee et al.; Receptor Activity-Modifying Protein 1 Determines the Species Selectivity of Non-peptide CGRP Receptor Antagonists; The Journal of Biological Chemistry; vol. 227, No. 16, Apr. 19, 2002, pp. 14294-14298; The American Society of Biochemistry and Molecular Biology, Inc.

* cited by examiner

*Primary Examiner*—Bruck Kifle
(74) *Attorney, Agent, or Firm*—Michael P. Morris; Mary-Ellen M. Devlin; Alan R. Stempel

(57) ABSTRACT

The present invention relates to substituted piperidines of general formula

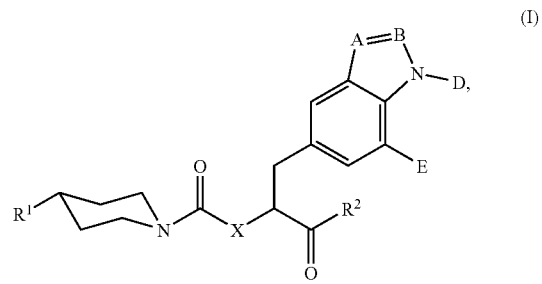

wherein A, B, D, E, X, $R^1$ and $R^2$ are defined as in claim 1, the tautomers, the diastereomers, the enantiomers, the hydrates thereof, the mixtures thereof and the salts thereof and the hydrates of the salts, particularly the physiologically acceptable salts thereof with inorganic or organic acids, pharmaceutical compositions containing these compounds, the use thereof and processes for the preparation thereof.

5 Claims, No Drawings

SELECTED CGRP-ANTAGONISTS PROCESS FOR PREPARING THEM AND THEIR USE AS PHARMACEUTICAL COMPOSITIONS

FIELD OF THE INVENTION

The present invention relates to selected CGRP-antagonists of general formula (I)

wherein A, B, D, E, X, $R^1$ and $R^2$ are defined as in claim 1, the tautomers, diastereomers, enantiomers, hydrates, mixtures thereof and the salts thereof as well as the hydrates of the salts, particularly the physiologically acceptable salts thereof with inorganic or organic acids, pharmaceutical compositions containing these compounds, the use thereof and processes for the preparation thereof.

In the above general formula in a first embodiment
A denotes a nitrogen atom or a CH group,
B denotes a nitrogen atom or a CH group,
D denotes a hydrogen atom or a methyl group,
E denotes a hydrogen, fluorine, chlorine or bromine atom, a methyl, ethyl or trifluoromethyl group,
X denotes a methylene or NH group,
$R^1$ denotes a group of formula and
$R^2$ denotes a group of formula A second embodiment of the present invention comprises those compounds of general formula I wherein the combination of A, B, D and E denotes a group of formula -continued

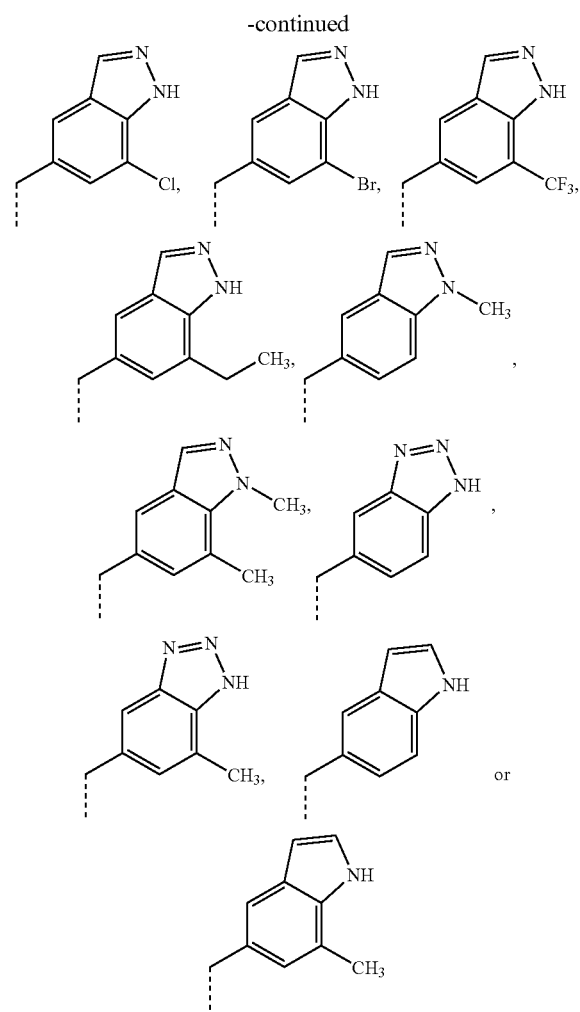

R¹ denotes a group of formula

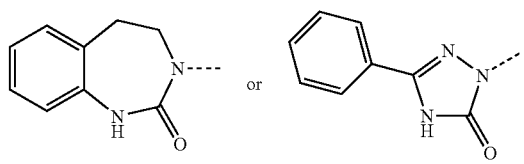

and
R² denotes a group of formula

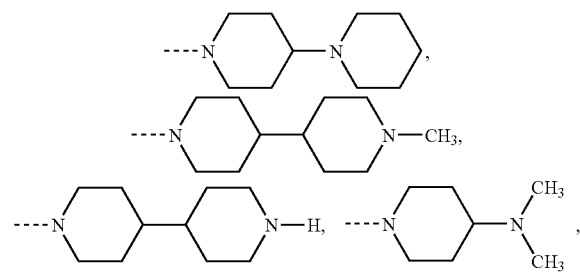

-continued

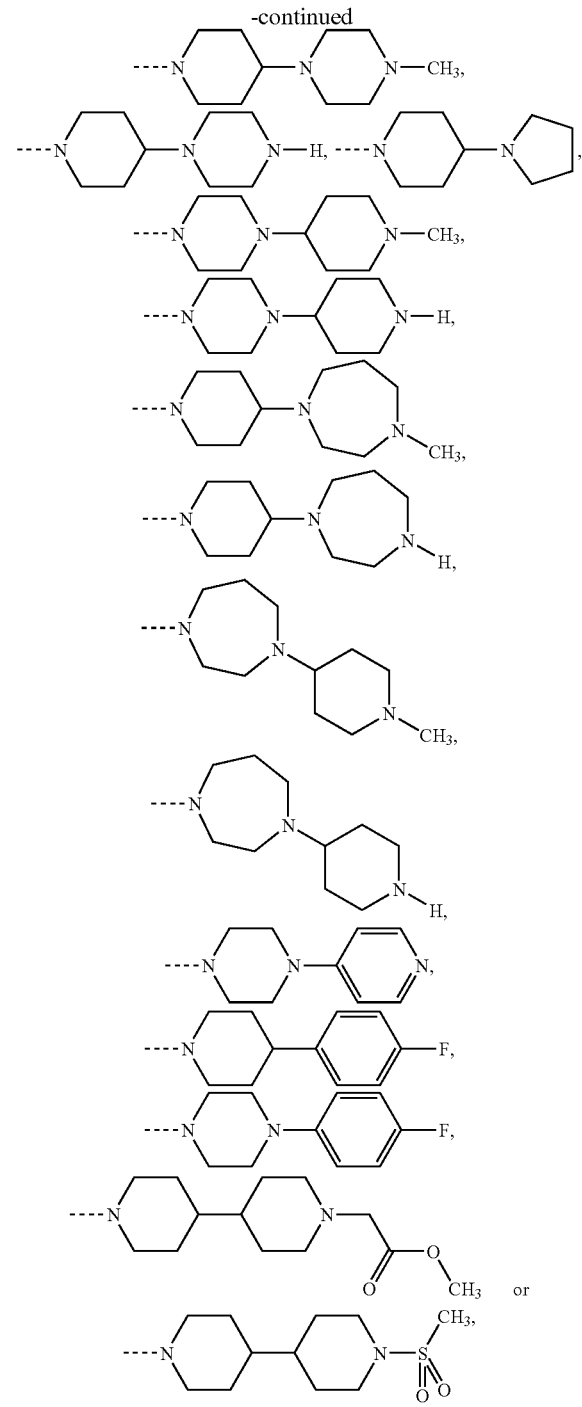

the tautomers, the diastereomers, the enantiomers, the hydrates thereof, the mixtures thereof and the salts thereof and the hydrates of the salts.

The following preferred compounds of general formula I will now be mentioned by way of example:

(1) 1-(1,4'-bipiperidinyl-1'-yl)-2-(1H-indazol-5-ylmethyl)-4-[4-(2-oxo-1,2,4,5,-tetrahydro-1,3-benzodiazepin-3-yl)-piperidin-1-yl]-butane-1,4-dione, (2) 2-(1H-indazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione, (3) 1-(4,4'-bipiperidinyl-1-yl)-2-(1H-indazol-5-ylmethyl)-4-[4-(2-oxo-1,2,4,5-tetrahydro-1,3-benzodiazepin-3-yl)-piperidin-1-yl]-butane-1,4-dione, (4) 1-(4-dimethylamino-piperidin-1-yl)-2-(1H-indazol-5-ylmethyl)-4-[4-(2-oxo-1,2,4,5-tetrahydro-1,3-benzodiazepin-3-yl)-piperidin-1-yl]-butane-1,4-dione, (5) (S)-2-(1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (6) 2-(1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (7) 2-(1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (8) 2-(1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (9) 2-(1H-indazol-5-ylmethyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butane-1,4-dione,

(10) 2-(1H-indazol-5-ylmethyl)-4-[4-(2-oxo-1,2,4,5-tetrahydro-1,3-benzodiazepin-3-yl)-piperidin-1-yl]-1-(4-perhydro-1,4-diazepin-1-yl-piperidin-1-yl)-butane-1,4-dione,

(11) 2-(1H-indazol-5-ylmethyl)-1-[4-(1-methyl-piperidin-4-yl)-perhydro-1,4-diazepin-1-yl]-4-[4-(2-oxo-1,2,4,5-tetrahydro-1,3-benzodiazepin-3-yl)-piperidin-1-yl]-butane-1,4-dione,

(12) 2-(1H-indazol-5-ylmethyl)-4-[4-(2-oxo-1,2,4,5-tetrahydro-1,3-benzodiazepin-3-yl)-piperidin-1-yl]-1-(4-piperidin-4-yl-perhydro-1,4-diazepin-1-yl)-butane-1,4-dione,

(13) 1-[4-(4-fluoro-phenyl)-piperazin-1-yl]-2-(1H-indazol-5-ylmethyl)-4-[4-(2-oxo-1,2,4,5-tetrahydro-1,3-benzodiazepin-3-yl)-piperidin-1-yl]-butane-1,4-dione,

(14) 1-[4-(4-fluoro-phenyl)-piperidin-1-yl]-2-(1H-indazol-5-ylmethyl)-4-[4-(2-oxo-1,2,4,5-tetrahydro-1,3-benzodiazepin-3-yl)-piperidin-1-yl]-butane-1,4-dione,

(15) 2-(1H-indazol-5-ylmethyl)-4-[4-(2-oxo-1,2,4,5-tetrahydro-1,3-benzodiazepin-3-yl)-piperidin-1-yl]-1-(4-pyridin-4-yl-piperazin-1-yl)-butane-1,4-dione,

(16) methyl (1'-{2-(1H-indazol-5-ylmethyl)-4-oxo-4-[4-(2-oxo-1,2,4,5-tetrahydro-1,3-benzodiazepin-3-yl)-piperidin-1-yl]-butyryl}-4,4'-bipiperidinyl-1-yl)-acetate,

(17) 2-(1H-indazol-5-ylmethyl)-1-(1'-methanesulfonyl-4,4'-bipiperidinyl-1-yl)-4-[4-(2-oxo-1,2,4,5-tetrahydro-1,3-benzodiazepin-3-yl)-piperidin-1-yl]-butane-1,4-dione,

(18) 4-(2-oxo-1,2,4,5-tetrahydro-1,3-benzodiazepin-3-yl)-piperidine-1-carboxylic acid [2-(1,4'-bipiperidinyl-1'-yl)-1-(1H-indazol-5-ylmethyl)-2-oxo-ethyl]-amide,

(19) 4-(2-oxo-1,2,4,5-tetrahydro-1,3-benzodiazepin-3-yl)-piperidine-1-carboxylic acid [1-(1H-indazol-5-ylmethyl)-2-(1'-methyl-4,4'-bipiperidinyl-1-yl)-2-oxo-ethyl]-amide,

(20) 4-(2-oxo-1,2,4,5-tetrahydro-1,3-benzodiazepin-3-yl)-piperidine-1-carboxylic acid [2-(4,4'-bipiperidinyl-1-yl)-1-(1H-indazol-5-ylmethyl)-2-oxo-ethyl]-amide,

(21) 4-(2-oxo-1,2,4,5-tetrahydro-1,3-benzodiazepin-3-yl)-piperidine-1-carboxylic acid [2-(4-dimethylamino-piperidin-1-yl)-1-(1H-indazol-5-ylmethyl)-2-oxo-ethyl]-amide,

(22) 4-(2-oxo-1,2,4,5-tetrahydro-1,3-benzodiazepin-3-yl)-piperidine-1-carboxylic acid {1-(1H-indazol-5-ylmethyl)-2-[4-(4-methyl-piperazin-1-yl)-piperidin-1-yl]-2-oxo-ethyl}-amide,

(23) 4-(2-oxo-1,2,4,5-tetrahydro-1,3-benzodiazepin-3-yl)-piperidine-1-carboxylic acid [1-(1H-indazol-5-ylmethyl)-2-oxo-2-(4-piperazin-1-yl-piperidin-1-yl)-ethyl]-amide,

(24) 4-(2-oxo-1,2,4,5-tetrahydro-1,3-benzodiazepin-3-yl)-piperidine-1-carboxylic acid {1-(1H-indazol-5-ylmethyl)-2-[4-(1-methyl-piperidin-4-yl)-piperazin-1-yl]-2-oxo-ethyl}-amide,

(25) 4-(2-oxo-1,2,4,5-tetrahydro-1,3-benzodiazepin-3-yl)-piperidine-1-carboxylic acid [1-(1H-indazol-5-ylmethyl)-2-oxo-2-(4-piperidin-4-yl-piperazin-1-yl)-ethyl]-amide,

(26) 4-(2-oxo-1,2,4,5-tetrahydro-1,3-benzodiazepin-3-yl)-piperidine-1-carboxylic acid {1-(1H-indazol-5-ylmethyl)-2-[4-(4-methyl-perhydro-1,4-diazepin-1-yl)-piperidin-1-yl]-2-oxo-ethyl}-amide,

(27) 4-(2-oxo-1,2,4,5-tetrahydro-1,3-benzodiazepin-3-yl)-piperidine-1-carboxylic acid [1-(1H-indazol-5-ylmethyl)-2-oxo-2-(4-perhydro-1,4-diazepin-1-yl-piperidin-1-yl)-ethyl]-amide,

(28) 4-(2-oxo-1,2,4,5-tetrahydro-1,3-benzodiazepin-3-yl)-piperidine-1-carboxylic acid {1-(1H-indazol-5-ylmethyl)-2-[4-(1-methyl-piperidin-4-yl)-perhydro-1,4-diazepin-1-yl]-2-oxo-ethyl}-amide,

(29) 4-(2-oxo-1,2,4,5-tetrahydro-1,3-benzodiazepin-3-yl)-piperidine-1-carboxylic acid [1-(1H-indazol-5-ylmethyl)-2-oxo-2-(4-piperidin-4-yl-perhydro-1,4-diazepin-1-yl)-ethyl]-amide,

(30) 4-(2-oxo-1,2,4,5-tetrahydro-1,3-benzodiazepin-3-yl)-piperidine-1-carboxylic acid [2-[4-(4-fluoro-phenyl)-piperazin-1-yl]-1-(1H-indazol-5-ylmethyl)-2-oxo-ethyl]-amide,

(31) 4-(2-oxo-1,2,4,5-tetrahydro-1,3-benzodiazepin-3-yl)-piperidine-1-carboxylic acid [2-[4-(4-fluoro-phenyl)-piperidin-1-yl]-1-(1H-indazol-5-ylmethyl)-2-oxo-ethyl]-amide,

(32) 4-(2-oxo-1,2,4,5-tetrahydro-1,3-benzodiazepin-3-yl)-piperidine-1-carboxylic acid [1-(1H-indazol-5-ylmethyl)-2-oxo-2-(4-pyridin-4-yl-piperazin-1-yl)-ethyl]-amide,

(33) methyl [1'-(3-(1H-indazol-5-yl)-2-{[4-(2-oxo-1,2,4,5-tetrahydro-1,3-benzodiazepin-3-yl)-piperidine-1-carbonyl]-amino}-propionyl)-4,4'-bipiperidinyl-1-yl]-acetate,

(34) 4-(2-oxo-1,2,4,5-tetrahydro-1,3-benzodiazepin-3-yl)-piperidine-1-carboxylic acid [1-(1H-indazol-5-ylmethyl)-2-(1'-methanesulphonyl-4,4'-bipiperidinyl-1-yl)-2-oxo-ethyl]-amide,

(35) 1-(1,4'-bipiperidinyl-1'-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(36) 1-(1'-methyl-4,4'-bipiperidinyl-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(37) 1-(4,4'-bipiperidinyl-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(38) 1-(4-dimethylamino-piperidin-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(39) 2-(7-methyl-1H-indazol-5-ylmethyl)-1-[4-(4-methyl-piperazin-1-yl)-piperidin-1-yl]-4-[4-(2-oxo-12,2,4,5-tetrahydro-1,3-benzodiazepin-3-yl)-piperidin-1-yl]butane-1,4-dione,

(40) 2-(7-methyl-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione,

(41) 2-(7-methyl-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione,

(42) 2-(7-methyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione,

(43) 2-(7-methyl-1H-indazol-5-ylmethyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butane-1,4-dione,

(44) 2-(7-methyl-1H-indazol-5-ylmethyl)-4-[4-(2-oxo-1,2,4,5-tetrahydro-1,3-benzodiazepin-3-yl)-piperidin-1-yl]-1-(4-perhydro-1,4-diazepin-1-yl-piperidin-1-yl)-butane-1,4-dione,

(45) 2-(7-methyl-1H-indazol-5-ylmethyl)-1-[4-(1-methyl-piperidin-4-yl)-perhydro-1,4-diazepin-1-yl]-4-[4-(2-oxo-1,2,4,5-tetrahydro-1,3-benzodiazepin-3-yl)-piperidin-1-yl]-butane-1,4-dione,

(46) 2-(7-methyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-perhydro-1,4-diazepin-1-yl)-butane-1,4-dione,

(47) 1-[4-(4-fluoro-phenyl)-piperazin-1-yl]-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(48) 1-[4-(4-fluoro-phenyl)-piperidin-1-yl]-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(49) 2-(7-methyl-1H-indazol-5-ylmethyl)-4-[4-(2-oxo-1,2,4,5-tetrahydro-1,3-benzodiazepin-3-yl)-piperidin-1-yl]-1-(4-pyridin-4-yl-piperazin-1-yl)-butane-1,4-dione,

(50) methyl (1'-{2-(7-methyl-1H-indazol-5-ylmethyl)-4-oxo-4-[4-(2-oxo-1,2,4,5-tetrahydro-1,3-benzodiazepin-3-yl)-piperidin-1-yl]-butyryl}-4,4'-bipiperidinyl-1-yl)-acetate,

(51) 1-(1'-methanesulphonyl-4,4'-bipiperidinyl-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(52) 4-(2-oxo-1,2,4,5-tetrahydro-1,3-benzodiazepin-3-yl)-piperidine-1-carboxylic acid [2-(1,4'-bipiperidinyl-1'-yl)-1-(7-methyl-1H-indazol-5-ylmethyl)-2-oxo-ethyl]-amide,

(53) 4-(2-oxo-1,2,4,5-tetrahydro-1,3-benzodiazepin-3-yl)-piperidine-1-carboxylic acid [2-(1'-methyl-4,4'-bipiperidinyl-1-yl)-1-(7-methyl-1H-indazol-5-ylmethyl)-2-oxo-ethyl]-amide,

(54) 4-(2-oxo-1,2,4,5-tetrahydro-1,3-benzodiazepin-3-yl)-piperidine-1-carboxylic acid [2-(4,4'-bipiperidinyl-1-yl)-1-(7-methyl-1H-indazol-5-ylmethyl)-2-oxo-ethyl]-amide,

(55) 4-(2-oxo-1,2,4,5-tetrahydro-1,3-benzodiazepin-3-yl)-piperidine-1-carboxylic acid [2-(4-dimethylamino-piperidin-1-yl)-1-(7-methyl-1H-indazol-5-ylmethyl)-2-oxo-ethyl]-amide,

(56) 4-(2-oxo-1,2,4,5-tetrahydro-1,3-benzodiazepin-3-yl)-piperidine-1-carboxylic acid {1-(7-methyl-1H-indazol-5-ylmethyl)-2-[4-(4-methyl-piperazin-1-yl)-piperidin-1-yl]-2-oxo-ethyl}-amide,

(57) 4-(2-oxo-1,2,4,5-tetrahydro-1,3-benzodiazepin-3-yl)-piperidine-1-carboxylic acid [1-(7-methyl-1H-indazol-5-ylmethyl)-2-oxo-2-(4-piperazin-1-yl-piperidin-1-yl)-ethyl]-amide,

(58) 4-(2-oxo-1,2,4,5-tetrahydro-1,3-benzodiazepin-3-yl)-piperidine-1-carboxylic acid {1-(7-methyl-1H-indazol-5-ylmethyl)-2-[4-(1-methyl-piperidin-4-yl)-piperazin-1-yl]-2-oxo-ethyl}-amide,

(59) 4-(2-oxo-1,2,4,5-tetrahydro-1,3-benzodiazepin-3-yl)-piperidine-1-carboxylic acid [1-(7-methyl-1H-indazol-5-ylmethyl)-2-oxo-2-(4-piperidin-4-yl-piperazin-1-yl)-ethyl]-amide,

(60) 4-(2-oxo-1,2,4,5-tetrahydro-1,3-benzodiazepin-3-yl)-piperidine-1-carboxylic acid {1-(7-methyl-1H-indazol-5-ylmethyl)-2-[4-(4-methyl-perhydro-1,4-diazepin-1-yl)-piperidin-1-yl]-2-oxo-ethyl}-amide,

(61) 4-(2-oxo-1,2,4,5-tetrahydro-1,3-benzodiazepin-3-yl)-piperidine-1-carboxylic acid [1-(7-methyl-1H-indazol-5-ylmethyl)-2-oxo-2-(4-perhydro-1,4-diazepin-1-yl-piperidin-1-yl)-ethyl]-amide,

(62) 4-(2-oxo-1,2,4,5-tetrahydro-1,3-benzodiazepin-3-yl)-piperidine-1-carboxylic acid {1-(7-methyl-1H-indazol-5-ylmethyl)-2-[4-(1-methyl-piperidin-4-yl)-perhydro-1,4-diazepin-1-yl]-2-oxo-ethyl}-amide,

(63) 4-(2-oxo-1,2,4,5-tetrahydro-1,3-benzodiazepin-3-yl)-piperidine-1-carboxylic acid [1-(7-methyl-1H-indazol-5-ylmethyl)-2-oxo-2-(4-piperidin-4-yl-perhydro-1,4-diazepin-1-yl)-ethyl]-amide,

(64) 4-(2-oxo-1,2,4,5-tetrahydro-1,3-benzodiazepin-3-yl)-piperidine-1-carboxylic acid [2-[4-(4-fluoro-phenyl)-piperazin-1-yl]-1-(7-methyl-1H-indazol-5-ylmethyl)-2-oxo-ethyl]-amide,

(65) 4-(2-oxo-1,2,4,5-tetrahydro-1,3-benzodiazepin-3-yl)-piperidine-1-carboxylic acid [2-[4-(4-fluoro-phenyl)-piperidin-1-yl]-1-(7-methyl-1H-indazol-5-ylmethyl)-2-oxo-ethyl]-amide,

(66) 4-(2-oxo-1,2,4,5-tetrahydro-1,3-benzodiazepin-3-yl)-piperidine-1-carboxylic acid [1-(7-methyl-1H-indazol-5-ylmethyl)-2-oxo-2-(4-pyridin-4-yl-piperazin-1-yl)-ethyl]-amide,

(67) methyl [1'-(3-(7-methyl-1H-indazol-5-yl)-2-{[4-(2-oxo-1,2,4,5-tetrahydro-1,3-benzodiazepin-3-yl)-piperidine-1-carbonyl]-amino}-propionyl)-4,4'-bipiperidinyl-1-yl]-acetate,

(68) 4-(2-oxo-1,2,4,5-tetrahydro-1,3-benzodiazepin-3-yl)-piperidine-1-carboxylic acid [2-(1'-methanesulphonyl-4,4'-bipiperidinyl-1-yl)-1-(7-methyl-1H-indazol-5-ylmethyl)-2-oxo-ethyl]-amide,

(69) 2-(1H-indazol-5-ylmethyl)-1-(1'-methyl-4,4'-bipiperidinyl-1-yl)-4-[4-(5-oxo-3-phenyl-4,5-dihydro-1,2,4-triazol-1-yl)-piperidin-1-yl]-butane-1,4-dione,

(70) 1-(4,4'-bipiperidinyl-1-yl)-2-(1H-indazol-5-ylmethyl)-4-[4-(5-oxo-3-phenyl-4,5-dihydro-1,2,4-triazol-1-yl)-piperidin-1-yl]-butane-1,4-dione,

(71) 2-(1H-indazol-5-ylmethyl)-1-[4-(4-methyl-piperazin-1-yl)-piperidin-1-yl]-4-[4-(5-oxo-3-phenyl-4,5-dihydro-1,2,4-triazol-1-yl)-piperidin-1-yl]-butane-1,4-dione,

(72) 2-(1H-indazol-5-ylmethyl)-4-[4-(5-oxo-3-phenyl-4,5-dihydro-1,2,4-triazol-1-yl) -piperidin1-yl]-1-(4-piperazin-1-yl-piperidin-1-yl)-butane-1,4-dione,

(73) 2-(1H-indazol-5-ylmethyl)-1-[4-(1-methyl-piperidin-4-yl)-piperazin-1-yl]-4-[4-(5-oxo-3-phenyl-4,5-dihydro-1,2,4-triazol-1-yl)-piperidin-1-yl]-butane-1,4-dione,

(74) 2-(1H-indazol-5-ylmethyl)-4-[4-(5-oxo-3-phenyl-4,5-dihydro-1,2,4-triazol-1-yl)-piperidin-1-yl ]-1-(4-piperidin-4-yl-piperazin-1-yl)-butane-1,4-dione,

(75) 1-(1,4'-bipiperidinyl-1'-yl)-2-(1H-indazol-5-ylmethyl)-4-[4-(5-oxo-3-phenyl-4,5-dihydro-1,2,4-triazol-1-yl)-piperidin-1-yl]-butane-1,4-dione,

(76) 1-(4-dimethylamino-piperidin-1-yl)-2-(1H-indazol-5-ylmethyl)-4-[4-(5-oxo-3-phenyl-4,5-dihydro-1,2,4-triazol-1-yl)-piperidin-1-yl]-butane-1,4-dione,

(77) 4-(5-oxo-3-phenyl-4,5-dihydro-1,2,4-triazol-1-yl)-piperidine-1-carboxylic acid [1-(1H-indazol-5-ylmethyl)-2-(1'-methyl-4,4'-bipiperidinyl-1-yl)-2-oxo-ethyl]-amide,

(78) 4-(5-oxo-3-phenyl-4,5-dihydro-1,2,4-triazol-1-yl)-piperidine-1-carboxylic acid [2-(4,4'-bipiperidinyl-1-yl)-1-(1H-indazol-5-ylmethyl)-2-oxo-ethyl]-amide,

(79) 4-(5-oxo-3-phenyl-4,5-dihydro-1,2,4-triazol-1-yl)-piperidine-1-carboxylic acid {1-(1H-indazol-5-ylmethyl)-2-[4-(4-methyl-piperazin-1-yl)-piperidin-1-yl]-2-oxo-ethyl}-amide,

(80) 4-(5-oxo-3-phenyl-4,5-dihydro-1,2,4-triazol-1-yl)-piperidine-1-carboxylic acid [1-(1H-indazol-5-ylmethyl)-2-oxo-2-(4-piperazin-1-yl-piperidin-1-yl)-ethyl]-amide,

(81) 4-(5-oxo-3-phenyl-4,5-dihydro-1,2,4-triazol-1-yl)-piperidine-1-carboxylic acid {1-(1H-indazol-5-ylmethyl)-2-[4-(1-methyl-piperidin-4-yl)-piperazin-1-yl]-2-oxo-ethyl}-amide,

(82) 4-(5-oxo-3-phenyl-4,5-dihydro-1,2,4-triazol-1-yl)-piperidine-1-carboxylic acid [1-(1H-indazol-5-ylmethyl)-2-oxo-2-(4-piperidin-4-yl-piperazin-1-yl)-ethyl]-amide,

(83) 4-(5-oxo-3-phenyl-4,5-dihydro-1,2,4-triazol-1-yl)-piperidine-1-carboxylic acid [2-(1,4'-bipiperidinyl-1'-yl)-1-(1H-indazol-5-ylmethyl)-2-oxo-ethyl]-amide,

(84) 4-(5-oxo-3-phenyl-4,5-dihydro-1,2,4-triazol-1-yl)-piperidine-1-carboxylic acid [2-(4-dimethylamino-piperidin-1-yl)-1-(1H-indazol-5-ylmethyl)-2-oxo-ethyl]-amide,

(85) 2-(7-ethyl-1H-indazol-5-ylmethyl)-1-(1'-methyl-4,4'-bipiperidinyl-1-yl)-4-[4-( 2-oxo-1,2,4,5-tetrahydro-1,3-benzodiazepin-3-yl)-piperidin-1-yl]-butane-1,4-dione,

(86) 1-(4,4'-bipiperidinyl-1-yl)-2-(7-ethyl-1H-indazol-5-ylmethyl)-4-[4-(2-oxo-1,2,4,5-tetrahydro-1,3-benzodiazepin-3-yl)-piperidin-1-yl]-butane-1,4-dione,

(87) 2-(7-ethyl-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione,

(88) 2-(7-ethyl-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione,

(89) 2-(7-ethyl-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione,

(90) 2-(7-ethyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione,

(91) 2-(7-chloro-1H-indazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione,

(92) 1-(4,4'-bipiperidinyl-1-yl)-2-(7-chloro-1H-indazol-5-ylmethyl)-4-[4-(2-oxo-1,2,4,5-tetrahydro-1,3-benzodiazepin-3-yl)-piperidin-1-yl]-butane-1,4-dione,

(93) 2-(7-chloro-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione,

(94) 2-(7-chloro-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione,

(95) 2-(7-chloro-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione,

(96) 2-(7-chloro-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione,

(97) 2-(7-bromo-1H-indazol-5-ylmethyl)-1-(1'-methyl-4,4'-bipiperidinyl-1-yl)-4-[4(2-oxo-1,2,4,5-tetrahydro-1,3-benzodiazepin-3-yl)-piperidin-1-yl]-butane-1,4-dione,

(98) 1-(4,4'-bipiperidinyl-1-yl)-2-(7-bromo-1H-indazol-5-ylmethyl)-4-[4-(2-oxo-1,2,4,5-tetrahydro-1,3-benzodiazepin-3-yl)-piperidin-1-yl]-butane-1,4-dione,

(99) 2-(7-bromo-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (100) 2-(7-bromo-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (101) 2-(7-bromo-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (102) 2-(7-bromo-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (103) 1-(1'-methyl-4,4'-bipiperidinyl-1-yl)-4-[4-(2-oxo-1,2,4,5-tetrahydro-1,3-benzodiazepin-3-yl)-piperidin-1-yl]-2-(7-trifluoromethyl-1H-indazol-5-ylmethyl)-butane-1,4-dione, (104) 1-(4,4'-bipiperidinyl-1-yl)-4-[4-(2-oxo-1,2,4,5-tetrahydro-1,3-benzodiazepin-3-yl)-piperidin-1-yl]-2-(7-trifluoromethyl-1H-indazol-5-ylmethyl)-butane-1,4-dione, (105) 2-(7-methyl-1H-indazol-5-ylmethyl)-1-[4-(4-methyl-piperazin-1-yl)-piperidin -1-yl]-4-[4-(2-oxo-1,2,4,5-tetrahydro-1,3-benzodiazepin-3-yl)-piperidin-1-yl]-butane-1,4-dione, (106) 4-[4-(2-oxo-1,2,4,5-tetrahydro-1,3-benzodiazepin-3-yl)-piperidin-1-yl]-1-(4-piperazin-1-yl-piperidin-1-yl)-2-(7-trifluoromethyl-1H-indazol-5-ylmethyl)-butane-1,4-dione, (107) 1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-2-(7-trifluoromethyl-1H-indazol-5-ylmethyl)-butane-1,4-dione, (108) 4-[4-(2-oxo-1,2,4,5-tetrahydro-1,3-benzodiazepin-3-yl)-piperidin-1-yl]-1-(4-piperidin-4-yl-piperazin-1-yl)-2-(7-trifluoromethyl-1H-indazol-5-ylmethyl)-butane-1,4-dione, (109) 1-(1'-methyl-4,4'-bipiperidinyl-1-yl)-2-(1-methyl-1H-indazol-5-ylmethyl) -4[4-(2-oxo-1,2,4,5-tetrahydro-1,3-benzodiazepin-3-yl)-piperidin-1-yl]-butane-1,4-dione, (110) 1-(4,4'-bipiperidinyl-1-yl)-2-(1-methyl-1H-indazol-5-ylmethyl)-4-[4-(2-oxo-1,2,4,5-tetrahydro-1,3-benzodiazepin-3-yl)-piperidin-1-yl]-butane-1,4-dione, (111) 2-(1-methyl-1H-indazol-5-ylmethyl)-1-[4-(4-methyl-piperazin-1-yl)-piperidin -1-yl]-4-[4-(2-oxo-1,2,4,5-tetrahydro-1,3-benzodiazepin-3-yl)-piperidin-1-yl]-butane-1,4-dione, (112) 2-(1-methyl-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (113) 2-(1-methyl-1H-indazol-5-ylmethyl)-1-[4-(1-methyl-piperidin-4-yl)-piperazin -1-yl]-4-[4-(2-oxo-1,2,4,5-tetrahydro-1,3-benzodiazepin-3-yl)-piperidin-1-yl]-butane-1,4-dione, (114) 2-(1-methyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (115) 2-(1,7-dimethyl-1H-indazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione, (116) 1-(4,4'-bipiperidinyl-1-yl)-2-(1,7-dimethyl-1H-indazol-5-ylmethyl)-4-[4-(2-oxo-1,2,4,5-tetrahydro-1,3-benzodiazepin-3-yl)-piperidin-1-yl]-butane-1,4-dione, (117) 2-(1,7-dimethyl-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (118) 2-(1,7-dimethyl-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (119) 2-(1,7-dimethyl-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (120) 2-(1,7-dimethyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (121) 2-(1H-benzotriazol-5-yl methyl)-1-(1'-methyl-4,4'-bipiperidinyl-1-yl)-4 [4(2-oxo-1,2,4,5-tetrahydro-1,3-benzodiazepin-3-yl)-piperidin-1-yl]-butane-1,4-dione, (122) 2-(1H-benzotriazol-5-ylmethyl)-1-(4,4'-bipiperidinyl-1-yl)-4-[4-(2-oxo-1,2,4,5-tetrahydro-1,3-benzodiazepin-3-yl)-piperidin-1-yl]-butane-1,4-dione, (123) 2-(1H-benzotriazol-5-yl methyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (124) 2-(1H-benzotriazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (125) 2-(1H-benzotriazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (126) 2-(1H-benzotriazol-5-yl methyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (127) 2-(7-methyl-1H-benzotriazol-5-ylmethyl)-1-(1'-methyl-4,4'-bipiperidinyl-1-[4-(2-oxo-1,2,4,5-tetrahydro-1,3-benzodiazepin-3-yl)-piperidin-1-yl]-butane-1,4-dione, (128) 1-(4,4'-bipiperidinyl-1-yl)-2-(7-methyl-1H-benzotriazol-5-ylmethyl)-4-[1,2,4,5-tetrahydro-1,3-benzodiazepin-3-yl)-piperidin-1-yl]-butane-1,4-dione, (129) 2-(7-methyl-1H-benzotriazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (130) 2-(7-methyl-1H-benzotriazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (131) 2-(7-methyl-1H-benzotriazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (132) 2-(7-methyl-1H-benzotriazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (133) 2-(1H-indol-5-ylmethyl)-1-(1'-methyl-4,4'-bipiperidinyl-1-yl)-4-[4(2-oxo-1,2,4,5-tetrahydro-1,3-benzodiazepin-3-yl)-piperidin-1-yl]-butane-1,4-dione, (134) 1-(4,4'-bipiperidinyl-1-yl)-2-(1H-indol-5-ylmethyl)-4-[4-(2-oxo-1,2,4,5-tetrahydro-1,3-benzodiazepin-3-yl)-piperidin-1-yl]-butane-1,4-dione, (135) 2-(1H-indol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (136) 2-(1H-indol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (137) 2-(1H-indol-5-ylmethyl)-1-[4-(1-methyl-piperidin-4-yl)-piperazin-1-yl]-4-[4(2-oxo-1,2,4,5-tetrahydro-1,3-benzodiazepin-3-yl)-piperidin-1-yl]-butane-1,4-dione, (138) 2-(1H-indol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (139) 1-(1'-methyl-4,4'-bipiperidinyl-1-yl)-2-(7-methyl-1H-indol-5-ylmethyl)-4-[4(2-oxo-1,2,4,5-tetrahydro-1,3-benzodiazepin-3-yl)-piperidin-1-yl]-butane-1,4-dione, (140) 1-(4,4'-bipiperidinyl-1-yl)-2-(7-methyl-1H-indol-5-ylmethyl)-4-[4-(2oxo-1,2,4,5-tetrahydro-1,3-benzodiazepin-3-yl)-piperidin-1-yl]-butane-1,4-dione, (141) 2-(7-methyl-1H-indol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (142) 2-(7-methyl-1H-indol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (143) 2-(7-methyl-1H-indol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (144) 2-(7-methyl-1H-indol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (145) 4-(2-oxo-1,2,4,5-tetrahydro-1,3-benzodiazepin-3-yl)-piperidine-1-carboxylic acid [1-(7-ethyl-1H-indazol-5-ylmethyl)-2-(1'-methyl-4,4'-bipiperidinyl-1-yl)-2-oxo-ethyl]-amide, (146) 4-(2-oxo-1,2,4,5-tetrahydro-1,3-benzodiazepin-3-yl)-piperidine-1-carboxylic acid [2-(4,4'-bipiperidinyl-1-yl)-1-(7-ethyl-1H-indazol-5-ylmethyl)-2-oxo-ethyl]-amide, (147) 4-(2-oxo-1,2,4,5-tetrahydro-1,3-benzodiazepin-3-yl)-piperidine-1-carboxylic acid {1-(7-ethyl-1H-indazol-5-ylmethyl)-2-[4-(4-methyl-piperazin-1-yl)-piperidin-1-yl]-2-oxo-ethyl}-amide, (148) 4-(2-oxo-1,2,4,5-tetrahydro-1,3-benzodiazepin-3-yl)-piperidine-1-carboxylic acid [1-(7-ethyl-1H-indazol-5-ylmethyl)-2-oxo-2-(4-piperazin-1-yl-piperidin-1-yl)-ethyl]-amide, (149) 4-(2-oxo-1,2,4,5-tetrahydro-1,3-benzodiazepin-3-yl)-piperidine-1-carboxylic acid {1-(7-ethyl-1H-indazol-5-ylmethyl)-2-[4-(1-methyl-piperidin-4-yl)-piperazin-1-yl]-2-oxo-ethyl}-amide, (150) 4-(2-oxo-1,2,4,5-tetrahydro-1,3-benzodiazepin-3-yl)-piperidine-1-carboxylic acid [1-(7-ethyl-1H-indazol-5-ylmethyl)-2-oxo-2-(4-piperidin-4-yl-piperazin-1-yl)-ethyl]-amide, (151) 4-(2-oxo-1,2,4,5-tetrahydro-1,3-benzodiazepin-3-yl)-piperidine-1-carboxylic acid [1-(7-chloro-1H-indazol-5-ylmethyl)-2-(1'-methyl-4,4'-bipiperidinyl-1-yl)-2-oxo-ethyl]-amide, (152) 4-(2-oxo-1,2,4,5-tetrahydro-1,3-benzodiazepin-3-yl)-piperidine-1-carboxylic acid [2-(4,4'-bipiperidinyl-1-yl)-1-(7-chloro-1H-indazol-5-ylmethyl)-2-oxo-ethyl]-amide, (153) 4-(2-oxo-1,2,4,5-tetrahydro-1,3-benzodiazepin-3-yl)-piperidine-1-carboxylic acid {1-(7-chloro-1H-indazol-5-ylmethyl)-2-[4-(4-methyl-piperazin-1-yl)-piperidin-1-yl]-2-oxo-ethyl}-amide, (154) 4-(2-oxo-1,2,4,5-tetrahydro-1,3-benzodiazepin-3-yl)-piperidine-1-carboxylic acid [1-(7-chloro-1H-indazol-5-ylmethyl)-2-oxo-2-(4-piperazin-1-yl-piperidin-1-yl)-ethyl]-amide, (155) 4-(2-oxo-1,2,4,5-tetrahydro-1,3-benzodiazepin-3-yl)-piperidine-1-carboxylic acid {1-(7-chloro-1H-indazol-5-ylmethyl)-2-[4-(1-methyl-piperidin-4-yl)-piperazin-1-yl]-2-oxo-ethyl}-amide, (156) 4-(2-oxo-1,2,4,5-tetrahydro-1,3-benzodiazepin-3-yl)-piperidine-1-carboxylic acid [1-(7-chloro-1H-indazol-5-ylmethyl)-2-oxo-2-(4-piperidin-4-yl-piperazin-1-yl)-ethyl]-amide, (157) 4-(2-oxo-1,2,4,5-tetrahydro-1,3-benzodiazepin-3-yl)-piperidine-1-carboxylic acid [1-(7-bromo-1H-indazol-5-ylmethyl)-2-(1'-methyl-4,4'-bipiperidinyl-1-yl)-2-oxo-ethyl]-amide, (158) 4-(2-oxo-1,2,4,5-tetrahydro-1,3-benzodiazepin-3-yl)-piperidine-1-carboxylic acid [2-(4,4'-bipiperidinyl-1-yl)-1-(7-bromo-1H-indazol-5-ylmethyl)-2-oxo-ethyl]-amide, (159) 4-(2-oxo-1,2,4,5-tetrahydro-1,3-benzodiazepin-3-yl)-piperidine-1-carboxylic acid {1-(7-bromo-1H-indazol-5-ylmethyl)-2-[4-(4-methyl-piperazin-1-yl)-piperidin-1-yl]-2-oxo-ethyl}-amide, (160) 4-(2-oxo-1,2,4,5-tetrahydro-1,3-benzodiazepin-3-yl)-piperidine-1-carboxylic acid [1-(7-bromo-1H-indazol-5-ylmethyl)-2-oxo-2-(4-piperazin-1-yl-piperidin-1-yl)-ethyl]-amide, (161) 4-(2-oxo-1,2,4,5-tetrahydro-1,3-benzodiazepin-3-yl)-piperidine-1-carboxylic acid {1-(7-bromo-1H-indazol-5-ylmethyl)-2-[4-(1-methyl-piperidin-4-yl)-piperazin-1-yl]-2-oxo-ethyl}-amide, (162) 4-(2-oxo-1,2,4,5-tetrahydro-1,3-benzodiazepin-3-yl)-piperidine-1-carboxylic acid [1-(7-bromo-1H-indazol-5-ylmethyl)-2-oxo-2-(4-piperidin-4-yl-piperazin-1-yl)-ethyl]-amide, (163) 4-(2-oxo-1,2,4,5-tetrahydro-1,3-benzodiazepin-3-yl)-piperidine-1-carboxylic acid [2-(1'-methyl-4,4'-bipiperidinyl-1-yl)-2-oxo-1-(7-trifluoromethyl-1H-indazol-5-ylmethyl)-ethyl]-amide, (164) 4-(2-oxo-1,2,4,5-tetrahydro-1,3-benzodiazepin-3-yl)-piperidine-1-carboxylic acid [2-(4,4'-bipiperidinyl-1-yl)-2-oxo-1-(7-trifluoromethyl-1H-indazol-5-ylmethyl)-ethyl]-amide, (165) 4-(2-oxo-1,2,4,5-tetrahydro-1,3-benzodiazepin-3-yl)-piperidine-1-carboxylic acid [2-[4-(4-methyl-piperazin-1-yl)-piperidin-1-yl]-2-oxo-1-(7-trifluoromethyl-1H-indazol-5-ylmethyl)-ethyl]-amide, (166) 4-(2-oxo-1,2,4,5-tetrahydro-1,3-benzodiazepin-3-yl)-piperidine-1-carboxylic acid [2-oxo-2-(4-piperazin-1-yl-piperidin-1-yl)-1-(7-trifluoromethyl-1H-indazol-5-ylmethyl)-ethyl]-amide, (167) 4-(2-oxo-1,2,4,5-tetrahydro-1,3-benzodiazepin-3-yl)-piperidine-1-carboxylic acid [2-[4-(1-methyl-piperidin-4-yl)-piperazin-1-yl]-2-oxo-1-(7-trifluoromethyl-1H-indazol-5-ylmethyl)-ethyl]-amide, (168) 4-(2-oxo-1,2,4,5-tetrahydro-1,3-benzodiazepin-3-yl)-piperidine-1-carboxylic acid [2-oxo-2-(4-piperidin-4-yl-piperazin-1-yl)-1-(7-trifluoromethyl-1H-indazol-5-ylmethyl)-ethyl]-amide, (169) 4-(2-oxo-1,2,4,5-tetrahydro-1,3-benzodiazepin-3-yl)-piperidine-1-carboxylic acid [2-(1'-methyl-4,4'-bipiperidinyl-1-yl)-1-(1-methyl-1H-indazol-5-ylmethyl)-2-oxo-ethyl]-amide, (170) 4-(2-oxo-1,2,4,5-tetrahydro-1,3-benzodiazepin-3-yl)-piperidine-1-carboxylic acid [2-(4,4'-bipiperidinyl-1-yl)-1-(1-methyl-1H-indazol-5-ylmethyl)-2-oxo-ethyl]-amide, (171) 4-(2-oxo-1,2,4,5-tetrahydro-1,3-benzodiazepin-3-yl)-piperidine-1-carboxylic acid {1-(1-methyl-1H-indazol-5-ylmethyl)-2-[4-(4-methyl-piperazin-1-yl)-piperidin-1-yl]-2-oxo-ethyl}-amide, (172) 4-(2-oxo-1,2,4,5-tetrahydro-1,3-benzodiazepin-3-yl)-piperidine-1-carboxylic acid [1-(1-methyl-1H-indazol-5-ylmethyl)-2-oxo-2-(4-piperazin-1-yl-piperidin-1-yl)-ethyl]-amide, (173) 4-(2-oxo-1,2,4,5-tetrahydro-1,3-benzodiazepin-3-yl)-piperidine-1-carboxylic acid {1-(1-methyl-1H-indazol-5-ylmethyl)-2-[4-(1-methyl-piperidin-4-yl)-piperazin-1-yl]-2-oxo-ethyl}-amide, (174) 4-(2-oxo-1,2,4,5-tetrahydro-1,3-benzodiazepin-3-yl)-piperidine-1-carboxylic acid [1-(1-methyl-1H-indazol-5-ylmethyl)-2-oxo-2-(4-piperidin-4-yl-piperazin-1-yl)-ethyl]-amide, (175) 4-(2-oxo-1,2,4,5-tetrahydro-1,3-benzodiazepin-3-yl)-piperidine-1-carboxylic acid [1-(1,7-dimethyl-1H-indazol-5-ylmethyl)-2-(1'-methyl-4,4'-bipiperidinyl-1-yl)-2-oxo-ethyl]-amide, (176) 4-(2-oxo-1,2,4,5-tetrahydro-1,3-benzodiazepin-3-yl)-piperidine-1-carboxylic acid [2-(4,4'-bipiperidinyl-1-yl)-1-(1,7-dimethyl-1H-indazol-5-ylmethyl)-2-oxo-ethyl]-amide, (177) 4-(2-oxo-1,2,4,5-tetrahydro-1,3-benzodiazepin-3-yl)-piperidine-1-carboxylic acid {1-(1,7-dimethyl-1H-indazol-5-ylmethyl)-2-[4-(4-methyl-piperazin-1-yl)-piperidin-1-yl]-2-oxo-ethyl}-amide, (178) 4-(2-oxo-1,2,4,5-tetrahydro-1,3-benzodiazepin-3-yl)-piperidine-1-carboxylic acid [1-(1,7-dimethyl-1H-indazol-5-ylmethyl)-2-oxo-2-(4-piperazin-1-yl-piperidin-1-yl)-ethyl]-amide, (179) 4-(2-oxo-1,2,4,5-tetrahydro-1,3-benzodiazepin-3-yl)-piperidine-1-carboxylic acid {1-(1,7-dimethyl-1H-indazol-5-ylmethyl)-2-[4-(1-methyl-piperidin-4-yl)-piperazin-1-yl]-2-oxo-ethyl}-amide, (180) 4-(2-oxo-1,2,4,5-tetrahydro-1,3-benzodiazepin-3-yl)-piperidine-1-carboxylic acid [1-(1,7-dimethyl-1H-indazol-5-ylmethyl)-2-oxo-2-(4-piperidin-4-yl-piperazin-1-yl)-ethyl]-amide, (181) 4-(2-oxo-1,2,4,5-tetrahydro-1,3-benzodiazepin-3-yl)-piperidine-1-carboxylic acid [1-(1H-benzotriazol-5-ylmethyl)-2-(1'-methyl-4,4'-bipiperidinyl-1-yl)-2-oxo-ethyl]-amide, (182) 4-(2-oxo-1,2,4,5-tetrahydro-1,3-benzodiazepin-3-yl)-piperidine-1-carboxylic acid [1-(1H-benzotriazol-5-ylmethyl)-2-(4,4'-bipiperidinyl-1-yl)-2-oxo-ethyl]-amide, (183) 4-(2-oxo-1,2,4,5-tetrahydro-1,3-benzodiazepin-3-yl)-piperidine-1-carboxylic acid {1-(1H-benzotriazol-5-ylmethyl)-2-[4-(4-methyl-piperazin-1-yl)-piperidin-1-yl]-2-oxo-ethyl}-amide, (184) 4-(2-oxo-1,2,4,5-tetrahydro-1,3-benzodiazepin-3-yl)-piperidine-1-carboxylic acid [1-(1H-benzotriazol-5-ylmethyl)-2-oxo-2-(4-piperazin-1-yl-piperidin-1-yl)-ethyl]-amide, (185) 4-(2-oxo-1,2,4,5-tetrahydro-1,3-benzodiazepin-3-yl)-piperidine-1-carboxylic acid {1-(1H-benzotriazol-5-ylmethyl)-2-[4-(1-methyl-piperidin-4-yl)-piperazin-1-yl]-2-oxo-ethyl}-amide, (186) 4-(2-oxo-1,2,4,5-tetrahydro-1,3-benzodiazepin-3-yl)-piperidine-1-carboxylic acid [1-(1H-benzotriazol-5-ylmethyl)-2-oxo-2-(4-piperidin-4-yl-piperazin-1-yl)-ethyl]-amide, (187) 4-(2-oxo-1,2,4,5-tetrahydro-1,3-benzodiazepin-3-yl)-piperidine-1-carboxylic acid [1-(7-methyl-1H-benzotriazol-5-ylmethyl)-2-(1'-methyl-4,4'-bipiperidinyl-1-yl)-2-oxo-ethyl]-amide, (188) 4-(2-oxo-1,2,4,5-tetrahydro-1,3-benzodiazepin-3-yl)-piperidine-1-carboxylic acid [2-(4,4'-bipiperidinyl-1-yl)-1-(7-methyl-1H-benzotriazol-5-ylmethyl)-2-oxo-ethyl]-amide, (189) 4-(2-oxo-1,2,4,5-tetrahydro-1,3-benzodiazepin-3-yl)-piperidine-1-carboxylic acid {1-(7-methyl-1H-benzotriazol-5-ylmethyl)-2-[4-(4-methyl-piperazin-1-yl)-piperidin-1-yl]-2-oxo-ethyl}-amide,
(190) 4-(2-oxo-1,2,4,5-tetrahydro-1,3-benzodiazepin-3-yl)-piperidine-1-carboxylic acid [1-(7-methyl-1H-benzotriazol-5-ylmethyl)-2-oxo-2-(4-piperazin-1-yl-piperidin-1-yl)-ethyl]-amide,
(191) 4-(2-oxo-1,2,4,5-tetrahydro-1,3-benzodiazepin-3-yl)-piperidine-1-carboxylic acid {1-(7-methyl-1H-benzotriazol-5-ylmethyl)-2-[4-(1-methyl-piperidin-4-yl)-piperazin-1-yl]-2-oxo-ethyl}-amide,
(192) 4-(2-oxo-1,2,4,5-tetrahydro-1,3-benzodiazepin-3-yl)-piperidine-1-carboxylic acid [1-(7-methyl-1H-benzotriazol-5-ylmethyl)-2-oxo-2-(4-piperidin-4-yl-piperazin-1-yl)-ethyl]-amide,
(193) 4-(2-oxo-1,2,4,5-tetrahydro-1,3-benzodiazepin-3-yl)-piperidine-1-carboxylic acid [1-(1H-indol-5-ylmethyl)-2-(1'-methyl-4,4'-bipiperidinyl-1-yl)-2-oxo-ethyl]-amide,
(194) 4-(2-oxo-1,2,4,5-tetrahydro-1,3-benzodiazepin-3-yl)-piperidine-1-carboxylic acid [2-(4,4'-bipiperidinyl-1-yl)-1-(1H-indol-5-ylmethyl)-2-oxo-ethyl]-amide,
(195) 4-(2-oxo-1,2,4,5-tetrahydro-1,3-benzodiazepin-3-yl)-piperidine-1-carboxylic acid {1-(1H-indol-5-ylmethyl)-2-[4-(4-methyl-piperazin-1-yl)-piperidin-1-yl]-2-oxo-ethyl}-amide,
(196) 4-(2-oxo-1,2,4,5-tetrahydro-1,3-benzodiazepin-3-yl)-piperidine-1-carboxylic acid [1-(1H-indol-5-ylmethyl)-2-oxo-2-(4-piperazin-1-yl-piperidin-1-yl)-ethyl]-amide,
(197) 4-(2-oxo-1,2,4,5-tetrahydro-1,3-benzodiazepin-3-yl)-piperidine-1-carboxylic acid {1-(1H-indol-5-ylmethyl)-2-[4-(1-methyl-piperidin-4-yl)-piperazin-1-yl]-2-oxo-ethyl}-amide,
(198) 4-(2-oxo-1,2,4,5-tetrahydro-1,3-benzodiazepin-3-yl)-piperidine-1-carboxylic acid [1-(1H-indol-5-ylmethyl)-2-oxo-2-(4-piperidin-4-yl-piperazin-1-yl)-ethyl]-amide,
(199) 4-(2-oxo-1,2,4,5-tetrahydro-1,3-benzodiazepin-3-yl)-piperidine-1-carboxylic acid [2-(1'-methyl-4,4'-bipiperidinyl-1-yl)-1-(7-methyl-1H-indol-5-ylmethyl)-2-oxo-ethyl]-amide,
(200) 4-(2-oxo-1,2,4,5-tetrahydro-1,3-benzodiazepin-3-yl)-piperidine-1-carboxylic acid [2-(4,4'-bipiperidinyl-1-yl)-1-(7-methyl-1H-indol-5-ylmethyl)-2-oxo-ethyl]-amide,
(201) 4-(2-oxo-1,2,4,5-tetrahydro-1,3-benzodiazepin-3-yl)-piperidine-1-carboxylic acid {1-(7-methyl-1H-indol-5-ylmethyl)-2-[4-(4-methyl-piperazin-1-yl)-piperidin-1-yl]-2-oxo-ethyl}-amide,
(202) 4-(2-oxo-1,2,4,5-tetrahydro-1,3-benzodiazepin-3-yl)-piperidine-1-carboxylic acid [1-(7-methyl-1H-indol-5-ylmethyl)-2-oxo-2-(4-piperazin-1-yl-piperidin-1-yl)-ethyl]-amide,
(203) 4-(2-oxo-1,2,4,5-tetrahydro-1,3-benzodiazepin-3-yl)-piperidine-1-carboxylic acid {1-(7-methyl-1H-indol-5-ylmethyl)-2-[4-(1-methyl-piperidin-4-yl)-piperazin-1-yl]-2-oxo-ethyl}-amide,
(204) 4-(2-oxo-1,2,4,5-tetrahydro-1,3-benzodiazepin-3-yl)-piperidine-1-carboxylic acid [1-(7-methyl-1H-indol-5-ylmethyl)-2-oxo-2-(4-piperidin-4-yl-piperazin-1-yl)-ethyl]-amide, the tautomers, the diastereomers, the enantiomers, the hydrates thereof, the mixtures thereof and the salts thereof and the hydrates of the salts.

The compounds of general formula (I) are prepared by methods known in principle. The following methods have proved particularly satisfactory for preparing the compounds of general formula (I) according to the invention:

(a) In order to prepare compounds of general formula (I) wherein X denotes the NH group and A, B, D, E, $R^1$ and $R^2$ are as hereinbefore defined:

reacting piperidines of general formula

(III)

wherein $R^1$ is as hereinbefore defined, with carbonic acid derivatives of general formula

(IV)

wherein G denotes a nucleofugic group, preferably the phenoxy, 1H-imidazol-1-yl, 1H-1,2,4-triazol-1-yl, trichloromethoxy or the 2,5-dioxopyrrolidin-1-yloxy group, and with primary amines of general formula

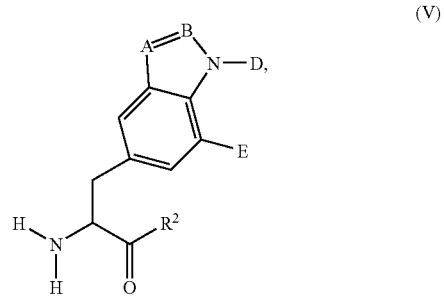

(V)

wherein $R^2$ is as hereinbefore defined, with the proviso that these groups do not contain any other free primary or secondary aliphatic amino function.

The fundamentally two-step reactions are normally carried out as one-pot processes, in which, preferably, in the first step, one of the two components (III) or (V) is reacted with equimolar amounts of the carbonic acid derivative of general formula (IV) in a suitable solvent at lower temperature, then at least equimolar amounts of the other component (III) or (V) are added and the reaction is completed at a higher temperature. The reactions with bis-(trichloromethyl)-carbonate are preferably carried out in the presence of at least 2 equivalents (based on bis-(trichloromethyl)-carbonate) of a tertiary base, for example triethylamine, N-ethyldiisopropylamine, pyridine, 1,5-diaza-bicyclo-[4,3,0]-non-5-ene, 1,4-diazabicyclo[2,2,2]octane or 1,8-diazabicyclo-[5,4,0]-undec-7-ene. The solvents used, which should be anhydrous, may be for example tetrahydrofuran, dioxane, dimethylformamide, dimethylacetamide, N-methyl-2-pyrrolidone, 1,3-dimethyl-2-imidazolidinone or acetonitrile, while if bis-(trichloromethyl)-carbonate is used as the carbonyl component anhydrous chlorohydrocarbons, for example dichloromethane, 1,2-dichloroethane or trichloroethylene are preferred. The reaction temperatures for the first reaction step are between −30° C. and +25° C., preferably −5° C. and +10° C., for the second reaction step between +15° C. and the boiling temperature of the solvent used, preferably between +20° C. and +70° C. (cf. also: H. A. Staab and W. Rohr, "Synthesen mit heterocyclischen Amiden (Azoliden)", Neuere Methoden der Präparativen Organischen Chemie, Volume V, p. 53–93, Verlag Chemie, Weinheim/Bergstr., 1967; P. Majer and R. S. Randad, J. Org. Chem. 59, p. 1937–1938 (1994); K. Takeda, Y. Akagi, A. Saiki, T. Sukahara and H. Ogura, Tetrahedron Letters 24 (42), 4569–4572 (1983)).

(b) In order to prepare compounds of general formula (I) wherein X denotes the methylene group and A, B, D, E, $R^1$ and $R^2$ are as hereinbefore defined, with the proviso that these groups do not contain any other free primary or secondary aliphatic amino function:

Coupling a carboxylic acid of general formula

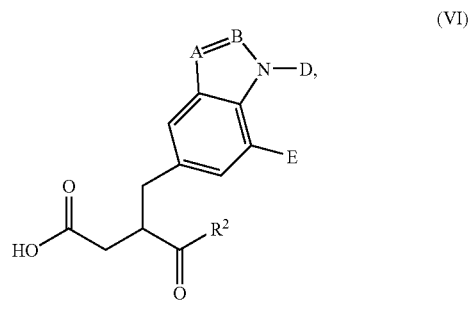

(VI)

wherein A, B, D, E and $R^2$ are as hereinbefore defined, with a piperidine of general formula

(III)

wherein $R^1$ is as hereinbefore defined.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N-N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between –30 and +30° C., preferably –20 and +25° C. If necessary, N-ethyl-diisopropylamine (DIEA) (Hünig base) is preferably used as an additional auxiliary base.

The so-called anhydride process is used as a further coupling method for synthesising compounds of general formula (I) (cf. also: M. Bodanszky, "Peptide Chemistry", Springer-Verlag 1988, p. 58–59; M. Bodanszky, "Principles of Peptide Synthesis", Springer-Verlag 1984, p. 21–27). The Vaughan variant of the mixed anhydride process is preferred (J. R. Vaughan Jr., J. Amer. Chem. Soc. 73, 3547 (1951)), in which the mixed anhydride of the carboxylic acid of general formula (VI) which is to be coupled and monoisobutyl carbonate is obtained, using isobutyl chlorocarbonate in the presence of bases such as 4-methyl-morpholine or 4-ethyl-morpholine. The preparation of this mixed anhydride and the coupling with amines are carried out in a one-pot process, using the above-mentioned solvents and at temperatures between –20 and +25° C., preferably 0° C. and +25° C.

(c) In order to prepare compounds of general formula (I) wherein X denotes the methylene group and A, B, D, E, $R^1$ and $R^2$ are as hereinbefore defined, with the proviso that these groups do not contain any free primary or secondary amine:

coupling a compound of general formula

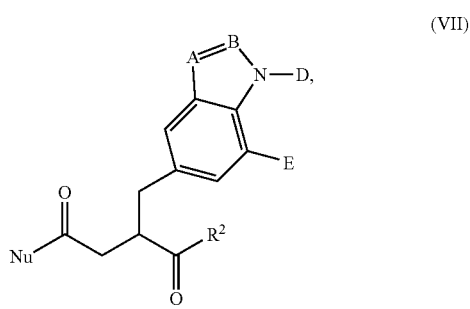

(VII)

wherein A, B, D, E and $R^2$ are as hereinbefore defined, with the proviso that $R^2$ does not contain any primary or secondary amine, and Nu denotes a leaving group, for example a halogen atom, such as the chlorine, bromine or iodine atom, an alkyl-sulphonyloxy group with 1 to 10 carbon atoms in the alkyl moiety, a phenylsulphonyloxy or naphthylsulphonyloxy group optionally mono-, di- or trisubstituted by chlorine or bromine atoms or by methyl or nitro groups, while the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yl-oxy, 2,5-dioxopyrrolidin-1-yloxy, phthalimidyloxy, 1H-benzo-triazol-1-yloxy or azide group, with a piperidine of general formula

(III)

wherein $R^1$ is as hereinbefore defined.

The reaction is carried out under Schotten-Baumann or Einhorn conditions, i.e. the components are reacted in the presence of at least one equivalent of an auxiliary base at temperatures between –50° C. and +120° C., preferably –10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

(d) In order to prepare compounds of general formula (I) wherein A, B, D, E, $R^1$ and X are as hereinbefore defined:

coupling a carboxylic acid of general formula

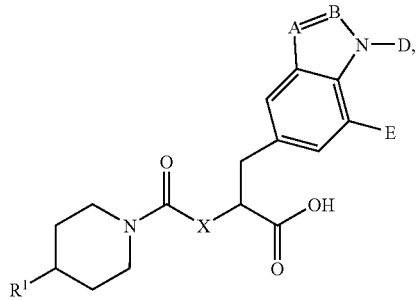

(VIII)

wherein A, B, D, E, $R^1$ and X are as hereinbefore defined, with an amine $R^2$ with the proviso that no other free primary or secondary aliphatic amino function is present.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N-N',N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30 and +30° C., preferably −20 and +25° C. If necessary, N-ethyl-diisopropylamine (DIEA) (Hünig base) is preferably used as an additional auxiliary base.

The so-called anhydride process is used as a further coupling method for synthesising compounds of general formula (I) (cf. also: M. Bodanszky, "Peptide Chemistry", Springer-Verlag 1988, p. 58–59; M. Bodanszky, "Principles of Peptide Synthesis", Springer-Verlag 1984, p. 21–27). The Vaughan variant of the mixed anhydride process is preferred (J. R. Vaughan Jr., J. Amer. Chem. Soc. 73, 3547 (1951)), in which the mixed anhydride of the carboxylic acid of general formula (VIII) which is to be coupled and monoisobutyl carbonate is obtained, using isobutyl chlorocarbonate in the presence of bases such as 4-methyl-morpholine or 4-ethyl-morpholine. The preparation of this mixed anhydride and the coupling with amines $R^2$ are carried out in a one-pot process, using the above-mentioned solvents and at temperatures between −20 and +25° C., preferably 0° C. and +25° C.

(e) In order to prepare compounds of general formula (I) wherein $R^1$ is as hereinbefore defined:

coupling a compound of general formula

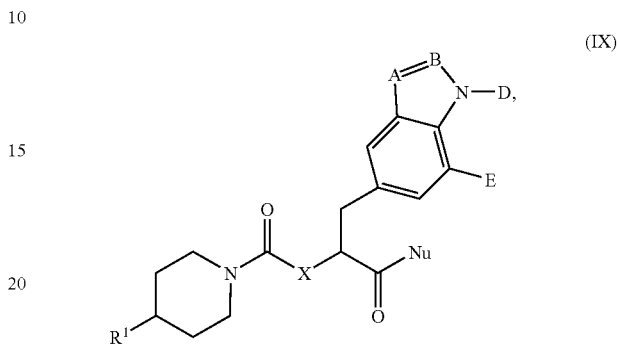

(IX)

wherein A, B, D, E, $R^1$ and X are as hereinbefore defined and Nu denotes a leaving group, for example a halogen atom, such as the chlorine, bromine or iodine atom, an alkylsulphonyloxy group with 1 to 10 carbon atoms in the alkyl moiety, a phenylsulphonyloxy or naphthylsulphonyloxy group optionally mono-, di- or trisubstituted by chlorine or bromine atoms or by methyl or nitro groups, while the substituents may be identical or different, a 1H-imidazol-1-yl, a 1H-pyrazol-1-yl optionally substituted by one or two methyl groups in the carbon skeleton, a 1H-1,2,4-triazol-1-yl, 1H-1,2,3-triazol-1-yl, 1H-1,2,3,4-tetrazol-1-yl, a vinyl, propargyl, p-nitrophenyl, 2,4-dinitrophenyl, trichlorophenyl, pentachlorophenyl, pentafluorophenyl, pyranyl or pyridinyl, a dimethylaminyloxy, 2(1H)-oxopyridin-1-yloxy, 2,5-dioxopyrrolidin-1-yloxy, phthalimidyloxy, 1H-benzo-triazol-1-yloxy or azide group, with an amine $R^2$, with the proviso that no other free primary or secondary aliphatic amino function is present.

The reaction is carried out under Schotten-Baumann or Einhorn conditions, i.e. the components are reacted in the presence of at least one equivalent of an auxiliary base at temperatures between −50° C. and +120° C., preferably −10° C. and +30° C., and optionally in the presence of solvents. The auxiliary bases used are preferably alkali metal and alkaline earth metal hydroxides, e.g. sodium hydroxide, potassium hydroxide or barium hydroxide, alkali metal carbonates, e.g. sodium carbonate, potassium carbonate or caesium carbonate, alkali metal acetates, e.g. sodium or potassium acetate, as well as tertiary amines, e.g. pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, the solvents used may be, for example, dichloromethane, tetrahydrofuran, 1,4-dioxane, acetonitrile, dimethyl formamide, dimethyl acetamide, N-methyl-pyrrolidone or mixtures thereof; if alkali metal or alkaline earth metal hydroxides, alkali metal carbonates or acetates are used as the auxiliary bases, water may also be added to the reaction mixture as cosolvent.

The new compounds of general formula (I) according to the invention contain one or more chiral centres. If for example there are two chiral centres the compounds may occur in the form of two pairs of diastereomeric antipodes. The invention covers the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula (I) may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+)-camphorsulphonic acid, or an optically active base, for example with (R)-(+)-1-phenyl-ethylamine, (S)-(−)-1-phenylethylamine or (S)-brucine.

According to a conventional method of separating isomers, the racemate of a compound of general formula (I) is reacted with one of the above-mentioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The starting compounds of general formula (III) may be obtained, if they are not known from the literature or even commercially available, according to the processes described in WO 98/11128 and DE 199 52 146. The starting compounds of general formula (IV) are commercially available. Compounds of general formula (V) may be obtained by methods familiar to the peptide chemist from protected phenylalanines and amines of general formula $R^2$. The starting compounds of general formula (VI) are obtained for example by reacting amines of general formula $R^2$ with 2-(alkoxycarbonylmethyl)-3-aryl-propanoic acids and subsequently cleaving the alkyl group by hydrolysis. The 2-(alkoxycarbonylmethyl)-3-aryl-propanoic acids required may be prepared analogously to methods known from the literature (David A. Evans, Leester D. Wu, John J. M. Wiener, Jeffrey S. Johnson, David H. B. Ripin and Jason S. Tedrow, J. Org. Chem 64, 6411–6417 [1999]; Saul G. Cohen and Aleksander Milovanovic, J. Am. Chem. Soc. 90, 3495–3502 [1968]; Hiroyuki Kawano, Youichi Ishii, Takao Ikariya, Masahiko Saburi, Sadao Yoshikawa, Yasuzo Uchida and Hidenori Kumobayashi, Tetrahedron Letters 28, 1905–1908 [1987]). Carboxylic acids of general formula (VIII) may be prepared using the methods described in WO 98/11128 from generally obtainable starting materials.

The compounds of general formula I obtained may, if they contain suitable basic functions, be converted, particularly for pharmaceutical use, into their physiologically acceptable salts with inorganic or organic acids. Suitable acids include for example hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

Moreover, the new compounds of formula (I), if they contain a carboxylic acid function, may if desired be converted into the addition salts thereof with inorganic or organic bases, particularly for pharmaceutical use into the physiologically acceptable addition salts thereof. Suitable bases for this include, for example, sodium hydroxide, potassium hydroxide, ammonia, cyclohexylamine, dicyclohexylamine, ethanolamine, diethanolamine and triethanolamine.

The present invention relates to racemates if the compounds of general formula (I) have only one chiral element. However, the application also includes the individual diastereomeric pairs of antipodes or mixtures thereof which are obtained if there is more than one chiral element in the compounds of general formula (I), as well as the individual optically active enantiomers of which the above-mentioned racemates are made up.

Also included in the subject matter of this invention are the compounds according to the invention, including the salts thereof, in which one or more hydrogen atoms are replaced by deuterium.

The new compounds of general formula (I) and the physiologically acceptable salts thereof have valuable pharmacological properties, based on their selective CGRP-antagonistic properties. The invention further relates to pharmaceutical compositions containing these compounds, their use and the preparation thereof.

The new compounds of general formula I mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 µl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 µl. The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity in the presence of 1 µM human CGRP-alpha during incubation.

The concentration binding curves are analysed using computer-aided non-linear curve matching.

The compounds mentioned hereinbefore show $IC_{50}$ values $\leq$10000 nM in the test described.

B. CGRP Antagonism in SK-N-MC Cells

SK-N-MC cells (1 million cells) are washed twice with 250 µl incubation buffer (Hanks' HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations ($10^{-11}$ to $10^{-6}$ M), or additionally the substance in 3 to 4 different concentrations, the mixture is incubated for another 15 minutes.

Intracellular cAMP is then extracted by the addition of 20 µl of 1 M HCl and centrifugation (2000×g, 4° C., for 15 minutes). The supernatants are frozen in liquid nitrogen and stored at –20° C.

The cAMP contents of the samples are determined by radioimmunoassay (Messrs. Amersham) and the $pA_2$ values of antagonistically acting substances are determined graphically.

The compounds of general formula I exhibit CGRP-antagonistic properties in the in vitro test model described, in a dosage range between $10^{-12}$ and $10^{-5}$ M.

In view of their pharmacological properties the compounds of general formula I and the salts thereof with physiologically acceptable acids are thus suitable for the acute and prophylactic treatment of headaches, particularly migraine or cluster headaches.

Moreover, the compounds of general formula I also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, inflammatory diseases, e.g. inflammatory diseases of the joints (arthritis), neurogenic inflammation of the oral mucosa, inflammatory lung diseases, allergic rhinitis, asthma, diseases accompanied by excessive vasodilatation and resultant reduced blood supply to the tissues, e.g. shock and sepsis. In addition, the compounds according to the invention have a general pain-relieving effect. The symptoms of menopausal hot flushes caused by vasodilatation and increased blood flow in oestrogen-deficient women and hormone-treated patients with prostate carcinoma are favourably affected by the CGRP-antagonists of the present application in a preventive and acute-therapeutic capacity, this therapeutic approach being distinguished from hormone replacement by the absence of side effects.

The dosage required to achieve a corresponding effect is conveniently 0.0001 to 3 mg/kg of body weight, preferably 0.01 to 1 mg/kg of body weight, when administered intravenously or subcutaneously and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone substitution, it is advisable to reduce the doses specified above, in which case the dosage may be from 1/5 of the lower limits mentioned above up to 1/1 of the upper limits specified.

The compounds prepared according to the invention may be administered either on their own or optionally in combination with other active substances for the treatment of migraine by intravenous, subcutaneous, intramuscular, intrarectal, intranasal route, by inhalation, transdermally or orally, while aerosol formulations are particularly suitable for inhalation. The combinations may be administered either simultaneously or sequentially.

Categories of active substance which may be used in the combination include e.g. antiemetics, prokinetics, neuroleptics, antidepressants, neurokinine antagonists, anti-convulsants, histamine-H1 receptor antagonists, antimuscarinics, β-blockers, α-agonists and α-antagonists, ergot alkaloids, mild analgesics, non-steroidal antiinflammatories, corticosteroids, calcium antagonists, $5\text{-HT}_{1B/1D}$ agonists or other anti-migraine agents, which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib and celecoxib.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, topiramate, riboflavin, montelukast, lisinopril, prochloroperazine, dexamethasone, flunarizine, dextropropoxyphene, meperidine, metoprolol, propranolol, nadolol, atenolol, clonidine, indoramin, carbamazepine, phenytoin, valproate, amitryptiline, lidocaine or diltiazem and other $5\text{-HT}_{1B/1D}$-agonists such as, for example, almotriptan, avitriptan, eletriptan, frovatriptan, naratriptan, rizatriptan, sumatriptan and zolmitriptan.

The dosage of these active substances is expediently 1/5 of the lowest recommended dose to 1/1 of the normally recommended dose, i.e. for example 20 to 100 mg of sumatriptan.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Experimental Section

As a rule, IR, UV, $^1$H-NMR and/or mass spectra have been obtained for the compounds prepared. Unless otherwise stated, $R_f$ values were obtained using ready-made silica gel TLC plates 60 $F_{254}$ (E. Merck, Darmstadt, Item no. 1.05714) without chamber saturation. The $R_f$ values obtained under the name Alox were obtained using ready-made aluminium oxide 60 $F_{254}$ TLC plates (E. Merck, Darmstadt, item no. 1.05713) without chamber saturation. The ratios given for the eluants relate to units by volume of the solvent in question. For chromatographic purification, silica gel made by Millipore (MATREX™, 35–70 my) was used.

The HPLC data provided are measured using the parameters specified below: Analytical column: Zorbax column (Agilent Technologies), SB (Stable Bond)—C18; 3.5 μm; 4.6×75 mm; column temperature: 30° C.; flow: 0.8 mL/min; injection volume: 5 μL; detection at 254 nm

| time (min) | percent by volume of water (with 0.1% formic acid) | percent by volume of acetonitrile (with 0.1% formic acid) |
|---|---|---|
| 0 | 90 | 10 |
| 9 | 10 | 90 |
| 10 | 10 | 90 |
| 11 | 90 | 10 |

In preparative HPLC purifications as a rule the same gradients are used as were used to raise the analytical HPLC data.

The products are collected under mass control and the fractions containing the product are combined and freeze-dried. If no detailed information is given as to the configuration, it is not clear whether it is a pure enantiomer or whether partial or even complete racemisation has occurred.

The following abbreviations are used in the description of the experiments:
abs. absolute
Boc tert.-butoxycarbonyl
CDI N,N'-carbonyldiimidazole
CDT 1,1'-carbonyldi-(1,2,4-triazole)
DMF N,N-dimethylformamide
EtOAc ethyl acetate
EtOH ethanol
sat. saturated
semiconc. semiconcentrated
HCl hydrochloric acid
HOAc acetic acid
HOBt 1-hydroxybenzotriazole-hydrate
i. vac. in vacuo (in a vacuum)
KOH potassium hydroxide
conc. concentrated
MeOH methanol
NaCl sodium chloride
NaOH sodium hydroxide
org. organic
RT room temperature
TBTU 2-(1H-benzotriazol-1-yl)-1,1,3,3-tetramethyluronium-tetrafluoroborate
TFA trifluoroacetic acid
THF tetrahydrofuran
aqu. aqueous A) Preparation of Intermediate Products Intermediate Product 1:

1H-indazole-5-carbaldehyde

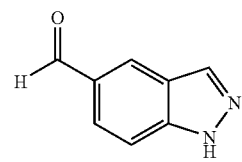

2.60 g (65.00 mmol) sodium hydride (60% in mineral oil) was added batchwise to a solution of 11.64 g (59.08 mmol) 5-bromo-1H-indazole in 150 mL THF under argon within 10 minutes and the mixture was stirred for 15 minutes at RT. The reaction mixture was cooled to −70° C. and within 30 minutes 100.00 mL (130.00 mmol) sec-butyllithium (1.3 M in cyclohexane) were added dropwise, while the temperature was kept below −60° C. The mixture was stirred for a further 2 h at −70° C. and then a solution of 20.00 mL (0.260 mol) DMF in 20 mL THF was added dropwise, while the temperature was kept below −50° C. The reaction mixture was slowly heated to RT and stirred for 16 h. Then the mixture was slowly cooled to 0° C. and slowly 180 mL of 2N aqueous HCl was added dropwise, the mixture was stirred for a further 15 minutes and the pH was adjusted to 9–10 with sat. aqueous sodium bicarbonate solution. The aqueous phase was exhaustively extracted with EtOAc, the combined org. phases were dried over magnesium sulphate and evaporated down i. vac. Column chromatography (silica gel, petroleum ether/EtOAc 1:1 v/v), trituration with hexane and drying i. vac. at 50° C. yielded the product.

Yield: 4.40 g (51% of theory)
$R_f$=0.37 (silica gel, petroleum ether/EtOAc 1/1 v/v)
ESI-MS: (M+H)$^+$=147

Intermediate Product 2:

methyl 2-[1-(1H-indazol-5-yl)-methylidene]-succinate

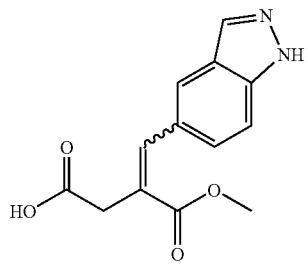

3.40 g (29.69 mmol) potassium-tert-butoxide was added to a solution of 2.00 g (13.68 mmol) 1H-indazol-5-carbaldehyde and 2.80 mL (20.97 mmol) dimethyl succinate in 100 mL tert-butanol and the mixture was stirred for 2 h at 60° C. The reaction mixture was cooled to RT, diluted with 200 mL water and the aqueous phase was washed twice with EtOAc. The aqueous phase was acidified with semiconc. aqueous HCl to pH 3–4 and exhaustively extracted with EtOAc. The combined org. phases were dried over magnesium sulphate, filtered through activated charcoal and evaporated down i. vac. The crude product was triturated with diisopropylether and a little isopropanol, filtered off and the residue was washed with diisopropylether (3.60 g, 1st stereoisomer). The mother liquor was evaporated down i. vac. and the residue was purified by column chromatography (silica gel, EtOAc/HOAc 10/0.1 v/v) and dried i. vac. (3.60 g, 2nd stereoisomer).

Yield: 7.20 g (2 stereoisomers, 74% of theory)
R$_f$=0.49 (silica gel, EtOAc/HOAc 100/1 v/v)
ESI-MS: (M+H)$^+$=261

Intermediate Product 3:

methyl 2-(1H-indazol-5-ylmethyl)-succinate

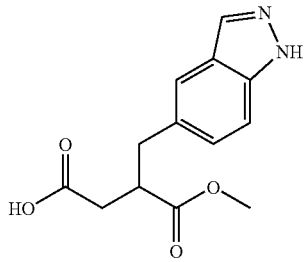

A suspension of 1.30 g (5.00 mmol) methyl 2-[1-(1H-indazol-5-yl)-methylidene]-succinate and 0.60 g Pd/C (10%) in 40 mL MeOH/EtOAc (1:1) was hydrogenated for 3 h at 50° C. and 3 bar hydrogen pressure. The catalyst was filtered off and the filtrate was evaporated down i. vac.
Yield: 1.30 g (99% of theory)
R$_f$=0.64 (silica gel, EtOAc/HOAc 100/1 v/v)
ESI-MS: (M+H)$^+$=263

Intermediate Product 4:

methyl 2-(1H-indazol-5-ylmethyl)-4-oxo-4-[4-(2-oxo-1,2,4,5-tetrahydro-1,3-benzodiazepin-3-yl)-piperidin-1-yl]-butyrate

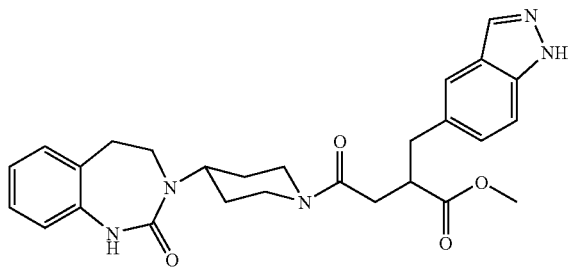

2.30 g (6.88 mmol) TBTU was added to a solution of 1.50 g (5.72 mmol) methyl 2-(1H-indazol-5-ylmethyl)-succinate and 1.30 mL (7.25 mmol) Hünig base in 50 mL THF and the mixture was stirred for 30 minutes at RT. 1.50 g (6.11 mmol) 3-piperidin-4-yl-1,3,4,5-tetrahydro-1,3-benzodiazepin-2-one was added and the mixture was stirred for another 5 h at RT. The reaction mixture was diluted with 50 mL EtOAc, the org. phase was washed twice with 15% aqueous potassium carbonate solution, dried over magnesium sulphate and evaporated down i. vac. The residue was purified by column chromatography (silica gel, dichloromethane/MeOH/sat. aqueous ammonia 50/45/5 v/v/v) and the crude product was triturated with diisopropylether.
Yield: 1.60 g (57% of theory)
R$_f$=0.51 (silica gel, dichloromethane/MeOH/sat. aqueous ammonia 50/45/5 v/v/v)
ESI-MS: (M+H)$^+$=492

Intermediate Product 5:

2-(1H-indazol-5-ylmethyl)-4-oxo-4-[4-(2-oxo-1,2,4,5-tetrahydro-1,3-benzodiazepin-3-yl)-piperidin-1-yl]-butyric acid

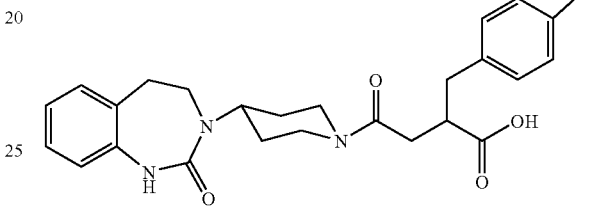

A solution of 0.20 g (8.18 mmol) lithium hydroxide in 10 mL water was added to a solution of 1.60 g (3.27 mmol) methyl 2-(1H-indazol-5-ylmethyl)-4-oxo-4-[4-(2-oxo-1,2,4,5-tetrahydro-1,3-benzodiazepin-3-yl)-piperidin-1-yl]-butyrate in 20 mL THF and the mixture was stirred for 16 h at RT. The reaction mixture was acidified with 15 mL 1N aqueous HCl and the aqueous phase was exhaustively extracted with EtOAc. The combined org. phases were dried over magnesium sulphate and evaporated down i. vac. The crude product was triturated with diisopropylether and dried i. vac.
Yield: 1.20 g (77% of theory)
R$_f$=0.05 (silica gel, dichloromethane/cyclohexane/MeOH/sat. aqueous ammonia 70/15/15/2 v/v/v/v)
ESI-MS: (M+H)$^+$=476

Intermediate Product 6:

7-methyl-1H-indazol-5-carbaldehyde

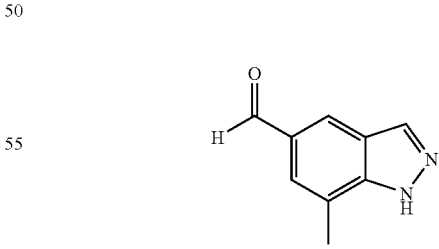

The intermediate product was obtained analogously to intermediate product 1 starting from 5-bromo-7-methyl-1H-indazole.
Yield: 7.10 g (69% of theory)
R$_f$=0.05 (silica gel, petroleum ether/EtOAc 2/1 v/v)
ESI-MS: (M)$^+$=160

Intermediate Product 7:

methyl 2-[1-(7-methyl-1H-indazol-5-yl)-meth-(E)-ylidene]-succinate

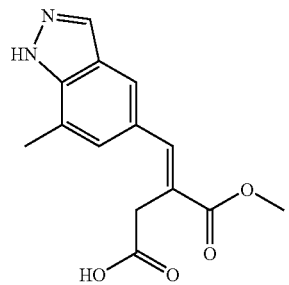

A suspension of 5.90 g (36.84 mmol) 7-methyl-1H-indazol-$\lambda^5$-carbaldehyde and 28.88 g (73.60 mmol) methyl 2-(triphenyl-$\lambda^5$-phosphanylidene)-succinate in 120 mL THF was stirred for 5 days at 40° C. 50 mL of DMSO and a further 14.0 g of methyl 2-(triphenyl-$\lambda^5$-phosphanylidene)-succinate were added and the mixture was stirred for 7 h at 95° C. The reaction mixture was poured onto 1 liter of water, the aqueous phase was washed with 500 mL EtOAc and the org. phase was extracted twice with water and 15% aqueous potassium carbonate solution. The combined aqueous phases were acidified to pH 1 with conc. aqueous HCl and the aqueous phases were exhaustively extracted with EtOAc. The combined org. phases were washed with water, dried over magnesium sulphate and evaporated down i. vac. The residue was purified by column chromatography (silica gel, gradient within 60 minutes, dichloromethane/MeOH/sat. aqueous ammonia 100/0/0→0/93/7 v/v/v).

Yield: 2.40 g (24% of theory)
$R_f$=0.40 (silica gel, dichloromethane/MeOH/sat. aqueous ammonia 85/15/1.5 v/v/v)
ESI-MS: (M+H)$^+$=275

Intermediate Product 8:

methyl 2-(7-methyl-1H-indazol-5-ylmethyl)-succinate

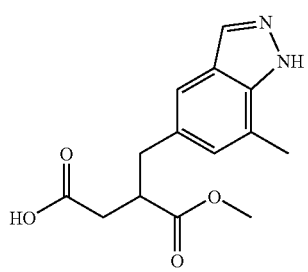

The intermediate product was obtained analogously to intermediate product 3 starting from methyl 2-[1-(7-methyl-1H-indazol-5-yl)-meth-(E)-ylidene]-succinate.

Yield: 1.10 g (45% of theory)
HPLC-MS: 5.6 minutes (Agilent Zorbax Stable Bond SB C18, 5 μm, 75×4.6 mm, gradient in 9 minutes, water/acetonitrile/formic acid 10/90/0.1→90/10/0.1 v/v/v)
ESI-MS: (M+H)$^+$=277

Intermediate Product 9:

methyl 2-(7-methyl-1H-indazol-5-ylmethyl)-4-oxo-4-[4-(2-oxo-1,2,4,5-tetrahydro-1,3-benzodiazepin-3-yl)-piperidin-1-yl]-butyrate

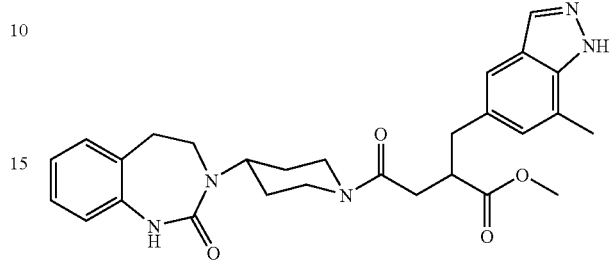

The intermediate product was obtained analogously to intermediate product 4 starting from methyl 2-(7-methyl-1H-indazol-5-ylmethyl)-succinate and 3-piperidin-4-yl-1,3,4,5-tetrahydro-1,3-benzodiazepin-2-one. The crude product was used in the next reaction step without any further purification.

Yield: 0.90 g (90% of theory)
$R_f$=0.35 (silica gel, EtOAc/MeOH 9/1 v/v)
HPLC-MS: 6.9 minutes (Agilent Zorbax Stable Bond SB C18, 5 μm, 75×4.6 mm, gradient in 9 minutes, water/acetonitrile/formic acid 10/90/0.1→90/10/0.1 v/v/v)
ESI-MS: (M+H)$^+$=504

Intermediate Product 10:

2-(7-methyl-1H-indazol-5-ylmethyl)-4-oxo-4-[4-(2-oxo-1,2,4,5-tetrahydro-1,3-benzodiazepin-3-yl)-piperidin-1-yl]-butyric acid

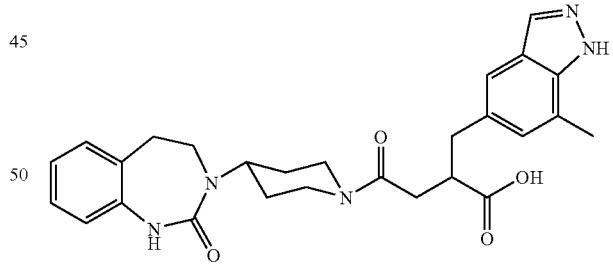

The intermediate product was obtained analogously to intermediate product 5 starting from methyl 2-(7-methyl-1H-indazol-5-ylmethyl)-4-oxo-4-[4-(2-oxo-1,2,4,5-tetrahydro-1,3-benzodiazepin-3-yl)-piperidin-1-yl]-butyrate. The crude product was used in the next reaction step without any further purification.

Yield: 0.80 g (82% of theory)
HPLC-MS: 6.2 minutes (Agilent Zorbax Stable Bond SB C18, 5 μm, 75×4.6 mm, gradient in 9 minutes, water/acetonitrile/formic acid 10/90/0.1→90/10/0.1 v/v/v)
ESI-MS: (M+H)$^+$=490

B) Preparation of End Compounds

Preparation of Example (5):

(S)-2-(1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione

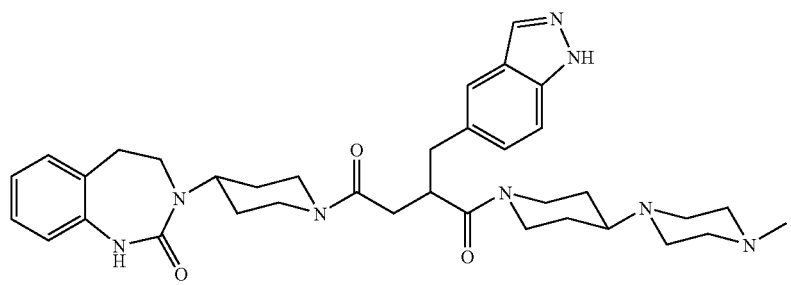

450.0 mg (1.345 mmol) TBTU and 0.270 mL (1.532 mmol) Hünig base was added at RT to a solution of 600.0 mg (1.262 mmol) 2-(1H-indazol-5-ylmethyl)-4-oxo-4-[4-(2-oxo-1,2,4,5-tetrahydro-1,3-benzodiazepin-3-yl)-piperidin-1-yl]-butyric acid in 30 mL THF and the mixture was stirred for 30 minutes. 250.0 mg (1.373 mmol) 1-methyl-4-piperidin-4-yl-piperazine was added and the mixture was stirred for another 16 h at RT. The reaction mixture was diluted with 50 mL EtOAc and the org. phase was washed twice with 15% aqueous potassium carbonate solution. The org. phase was dried over magnesium sulphate and evaporated down i. vac. The crude product was purified by column chromatography (silica gel, gradient dichloromethane/MeOH/sat. aqueous ammonia 100/0/0→80/18/2). The residue was triturated with diisopropylether and dried i. vac. at 50° C.

Yield: 520 mg (64% of theory)

$R_f$=0.37 (silica gel, dichloromethane/cyclohexane/MeOH/conc. aqueous ammonia 70/15/15/2 v/v/v/v)

ESI-MS: (M+H)$^+$=641

Preparation of Example 39:

2-(7-methyl-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione The product was obtained analogously to Example 1 from 2-(7-methyl-1H-indazol-5-ylmethyl)-4-oxo-4-[4-(2-oxo-1,2,4,5-tetrahydro-1,3-benzodiazepin-3-yl)-piperidin-1-yl]-butyric acid (intermediate product 10) and 1-methyl-4-piperidin-4-yl-piperazine. The crude product was purified by HPLC-MS (Agilent Zorbax Stable Bond SB C18, 5 µm, 75×4.6 mm, water/acetonitrile/formic acid 10/90/0.1→90/10/0.1 v/v/v).

Yield: 360 mg (34% of theory)

$R_f$=0.35 (silica gel, dichloromethane/MeOH/conc. aqueous ammonia 85/15/1.5 v/v/v)

ESI-MS: (M+H)$^+$=655

The following Examples may be prepared analogously:

(1)

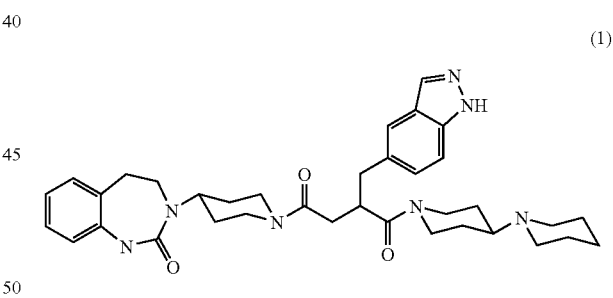

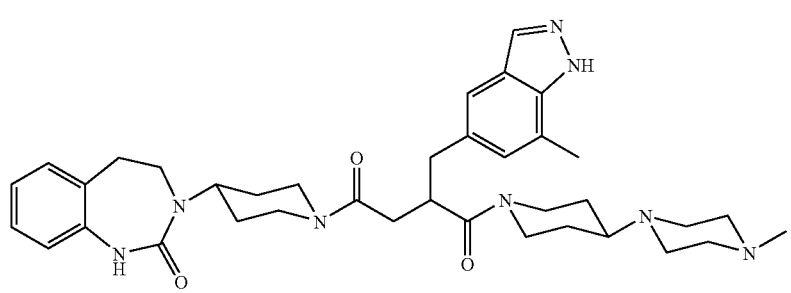

1-(1,4'-bipiperidinyl-1'-yl)-2-(1H-indazol-5-ylmethyl)-4-[4-(2-oxo-1,2,4,5-tetrahydro-1,3-benzodiazepin-3-yl)-piperidin-1-yl]-butane-1,4-dione,
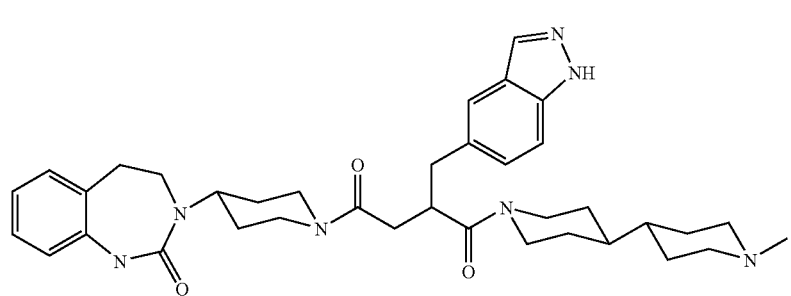
(2)
2-(1H-indazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione,
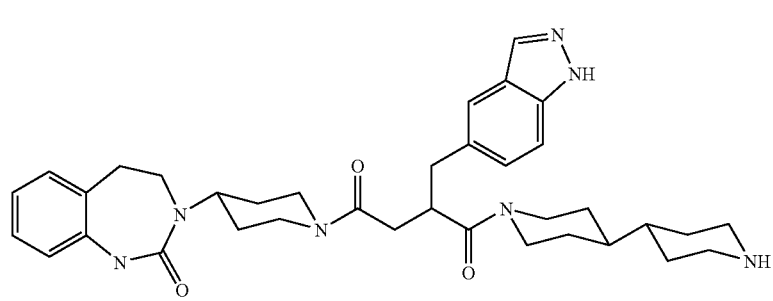
(3)
1-(4,4'-bipiperidinyl-1-yl)-2-(1H-indazol-5-ylmethyl)-4-[4-(2-oxo-1,2,4,5-tetrahydro-1,3-benzodiazepin-3-yl)-piperidin-1-yl]-butane-1,4-dione,
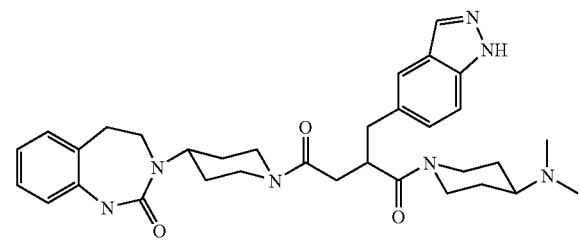
(4)

1-(4-dimethylamino-piperidin-1-yl)-2-(1H-indazol-5-ylmethyl)-4-[4-(2-oxo-1,2,4,5-tetrahydro-1,3-benzodiazepin-3-yl)-piperidin-1-yl]-butane-1,4-dione,
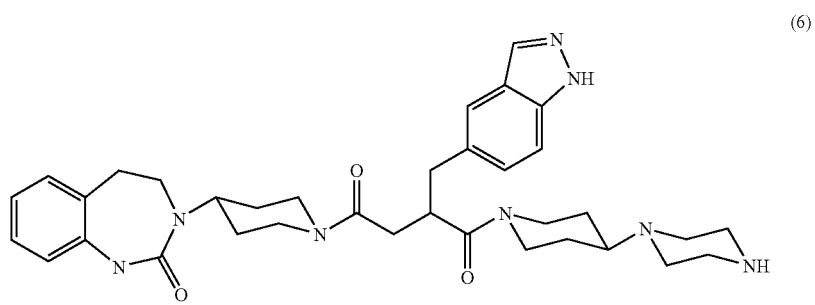
(6)
2-(1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione,
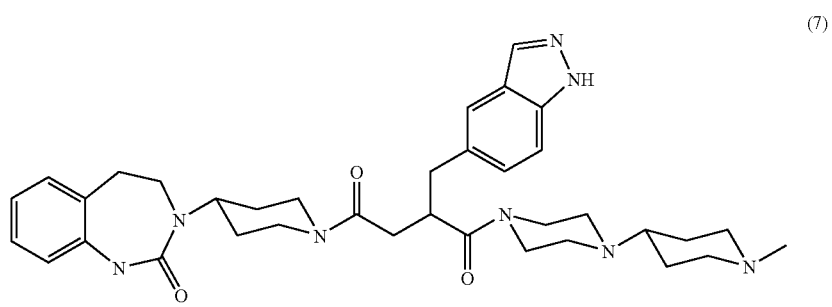
(7)
2-(1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione,
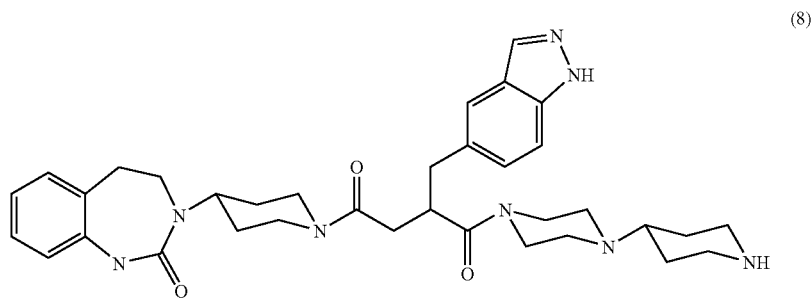
(8)

2-(1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione,
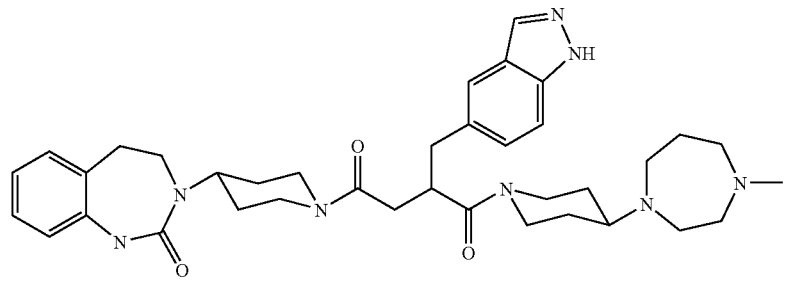
2-(1H-indazol-5-ylmethyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butane-1,4-dione,
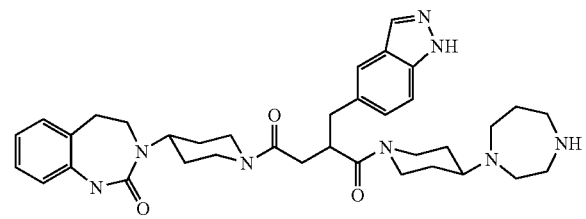
2-(1H-indazol-5-ylmethyl)-4-[4-(2-oxo-1,2,4,5-tetrahydro-1,3-benzodiazepin-3-yl)-piperidin-1-yl]-1-(4-perhydro-1,4-diazepin-1-yl-piperidin-1-yl)-butane-1,4-dione,
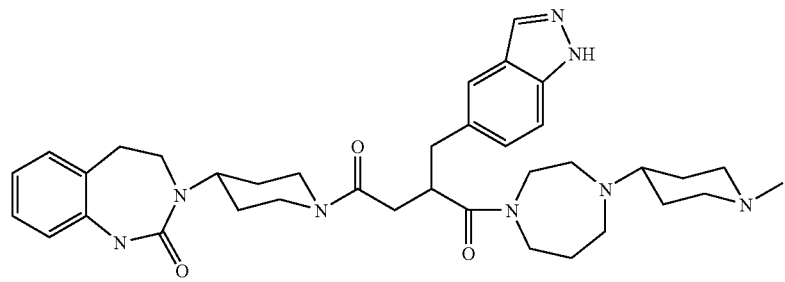

2-(1H-indazol-5-ylmethyl)-1-[4-(1-methyl-piperidin-4-yl)-perhydro-1,4-diazepin-1-yl]-4-[4-(2-oxo-1,2,4,5-tetrahydro-1,3-benzodiazepin-3-yl)-piperidin-1-yl]-butane-1,4-dione,

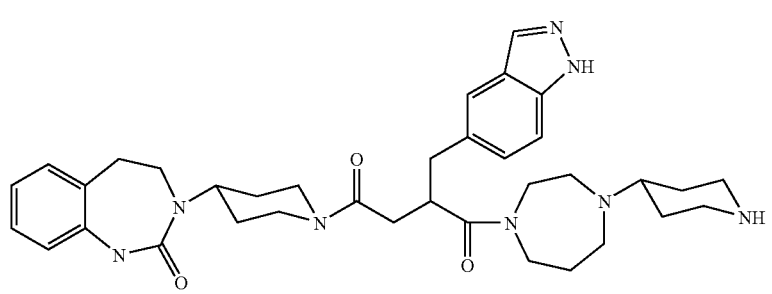
(12)

2-(1H-indazol-5-ylmethyl)-4-[4-(2-oxo-1,2,4,5-tetrahydro-1,3-benzodiazepin-3-yl)-piperidin-1-yl]-1-(4-piperidin-4-yl-perhydro-1,4-diazepin-1-yl)-butane-1,4-dione, 1-[4-(4-fluoro-phenyl)-piperidin-1-yl]-2-(1H-indazol-5-yl-methyl)-4-[4-(2-oxo-1,2,4,5-tetrahydro-1,3-benzodiazepin-3-yl)-piperidin-1-yl]-butane-1,4-dione, (13)

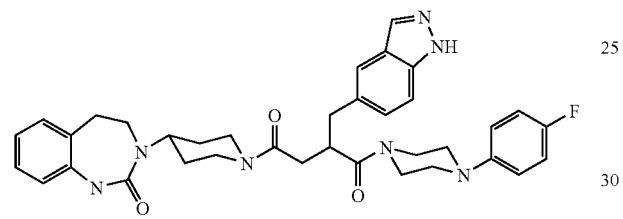

1-[4-(4-fluoro-phenyl)-piperazin-1-yl]-2-(1H-indazol-5-yl-methyl)-4-[4-(2-oxo-1,2,4,5-tetrahydro-1,3-benzodiazepin-3-yl)-piperidin-1-yl]-butane-1,4-dione, (14)

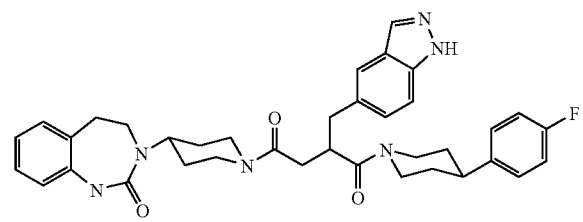

(15)

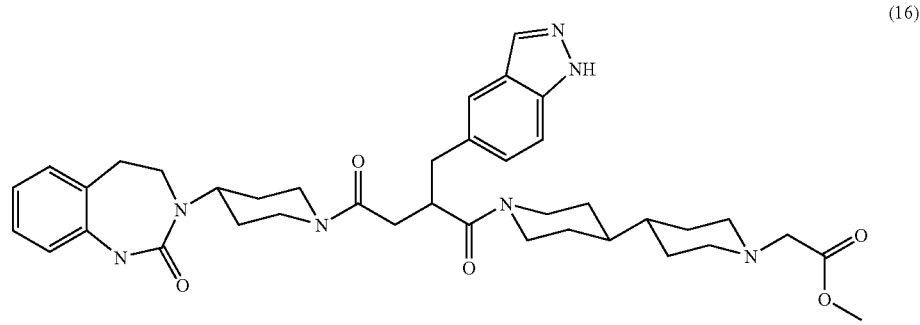

2-(1H-indazol-5-ylmethyl)-4-[4(2-oxo-1,2,4,5-tetrahydro-1,3-benzodiazepin-3-yl)-piperidin-1-yl]-1-(4-pyridin-4-yl-piperazin-1-yl)-butane-1,4-dione, (16)

methyl (1'-{2-(1H-indazol-5-ylmethyl)-4-oxo-4-[4-(2-oxo-1,2,4,5-tetrahydro-1,3-benzodiazepin-3-yl)-piperidin-1-yl]-butyryl}-4,4'-bipiperidinyl-1-yl)-acetate,

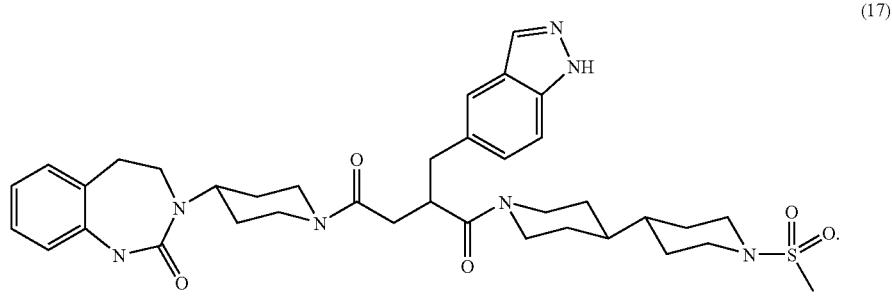

2-(1H-indazol-5-ylmethyl)-1-(1'-methanesulphonyl-4,4'-bipiperidinyl-1-yl)-4-[4-(2-oxo-1,2,4,5-tetrahydro-1,3-benzodiazepin-3-yl)-piperidin-1-yl]-butane-1,4-dione,

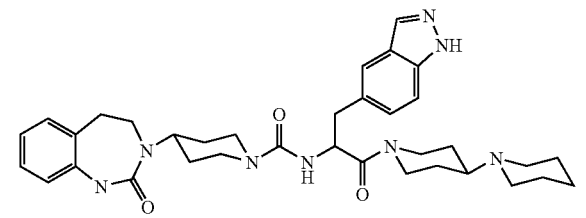

4-(2-oxo-1,2,4,5-tetrahydro-1,3-benzodiazepin-3-yl)-piperidine-1-carboxylic acid [2-(1,4'-bipiperidinyl-1'-yl)-1-(1H-indazol-5-ylmethyl)-2-oxo-ethyl]-amide,

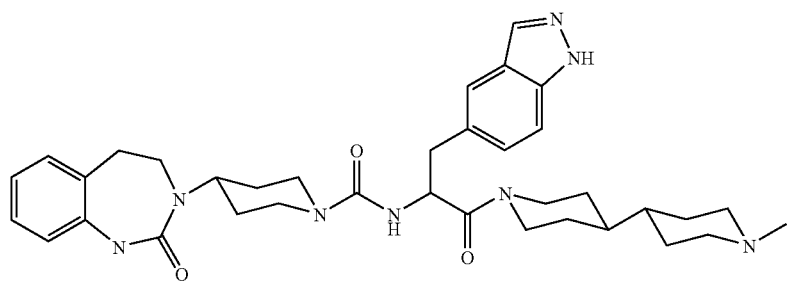

4-(2-oxo-1,2,4,5-tetrahydro-1,3-benzodiazepin-3-yl)-piperidine-1-carboxylic acid [1-(1H-indazol-5-ylmethyl)-2-(1'-methyl-4,4'-bipiperidinyl-1-yl)-2-oxo-ethyl]-amide,

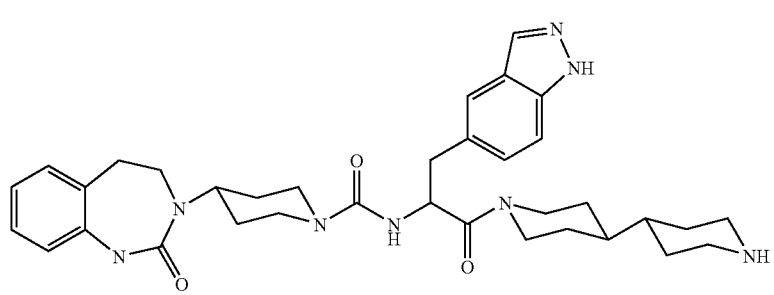

4-(2-oxo-1,2,4,5-tetrahydro-1,3-benzodiazepin-3-yl)-piperidine-1-carboxylic acid [2-(4,4'-bipiperidinyl-1-yl)-1-(1H-indazol-5-ylmethyl)-2-oxo-ethyl]-amide,

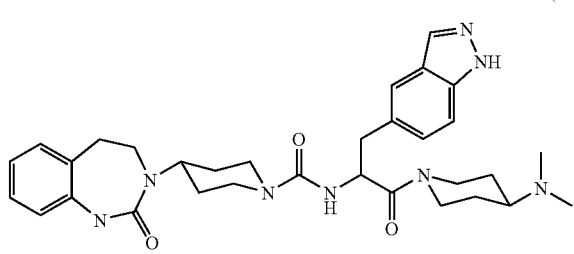

4-(2-oxo-1,2,4,5-tetrahydro-1,3-benzodiazepin-3-yl)-piperi-
dine-1-carboxylic acid [2-(4-dimethylamino-piperidin-1-
yl)-1-(1H-indazol-5-ylmethyl)-2-oxo-ethyl]-amide,

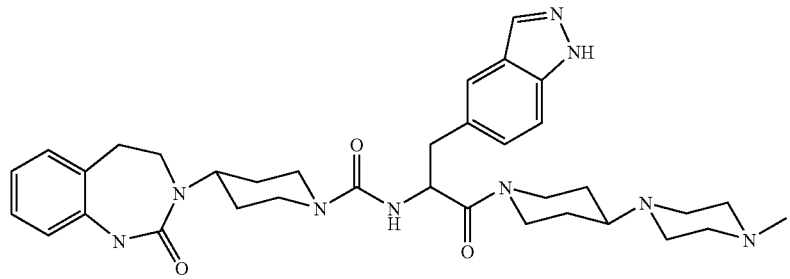

(22)

4-(2-oxo-1,2,4,5-tetrahydro-1,3-benzodiazepin-3-yl)-piperi-
dine-1-carboxylic acid {1-(1H-indazol-5-ylmethyl)-2-[4-
(4-methyl-piperazin-1-yl)-piperidin-1-yl]-2-oxo-ethyl}-
amide,

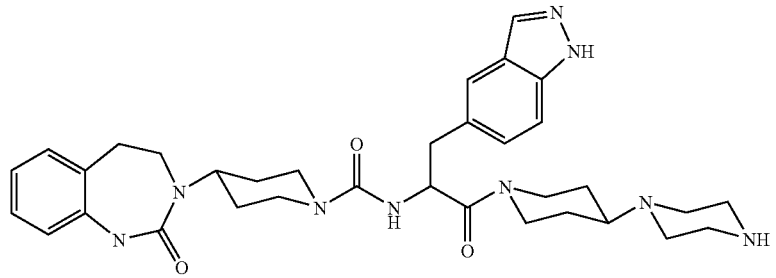

(23)

4-(2-oxo-1,2,4,5-tetrahydro-1,3-benzodiazepin-3-yl)-piperi-
dine-1-carboxylic acid [1-(1H-indazol-5-ylmethyl)-2-
oxo-2-(4-piperazin-1-yl-piperidin-1-yl)-ethyl]-amide,

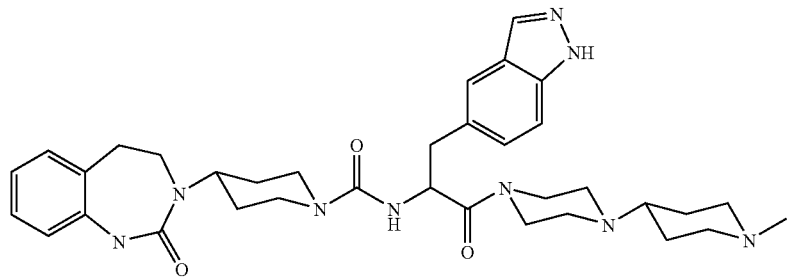

(24)

4-(2-oxo-1,2,4,5-tetrahydro-1,3-benzodiazepin-3-yl)-piperidine-1-carboxylic acid {1-(1H-indazol-5-ylmethyl)-2-[4-(1-methyl-piperidin-4-yl)-piperazin-1-yl]-2-oxo-ethyl}-amide,

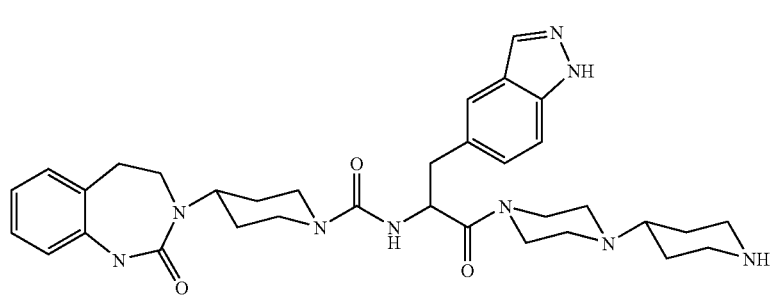

(25)

4-(2-oxo-1,2,4,5-tetrahydro-1,3-benzodiazepin-3-yl)-piperidine-1-carboxylic acid [1-(1H-indazol-5-ylmethyl)-2-oxo-2-(4-piperidin-4-yl)-ethyl]-amide,

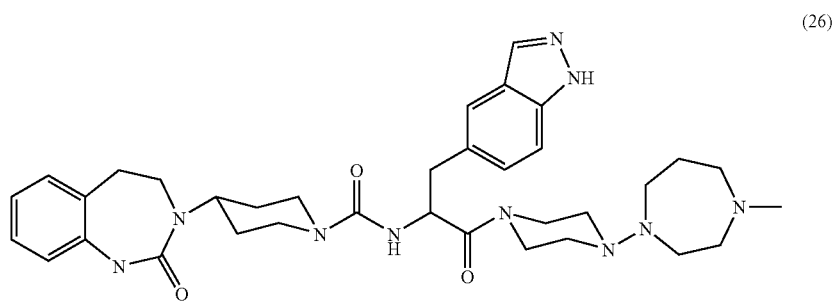

(26)

4-(2-oxo-1,2,4,5-tetrahydro-1,3-benzodiazepin-3-yl)-piperidine-1-carboxylic acid {1-(1H-indazol-5-ylmethyl)-2-[4-(4-methyl-perhydro-1,4-diazepin-1-yl)-piperidin-1-yl]-2-oxo-ethyl}-amide,

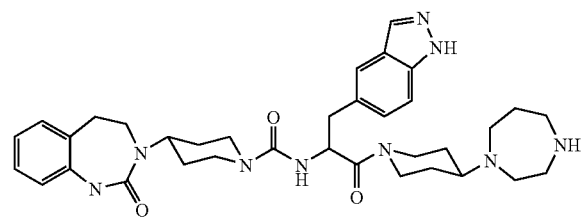

(27)

4-(2-oxo-1,2,4,5-tetrahydro-1,3-benzodiazepin-3-yl)-piperidine-1-carboxylic acid [1-(1H-indazol-5-ylmethyl)-2-oxo-2-(4-perhydro-1,4-diazepin-1-yl-piperidin-1-yl)-ethyl]-amide,

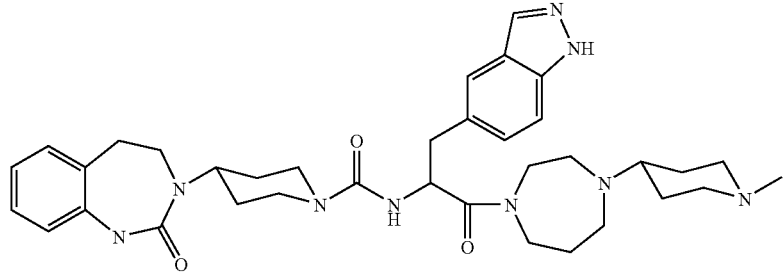

(28)

4-(2-oxo-1,2,4,5-tetrahydro-1,3-benzodiazepin-3-yl)-piperidine-1-carboxylic acid {1-(1H-indazol-5-ylmethyl)-2-[4-(1-methyl-piperidin-4-yl)-perhydro-1,4-diazepin-1-yl]-2-oxo-ethyl}-amide,

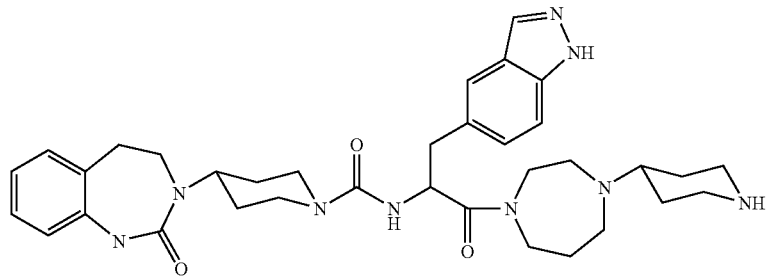

(29)

4-(2-oxo-1,2,4,5-tetrahydro-1,3-benzodiazepin-3-yl)-piperidine-1-carboxylic acid [1-(1H-indazol-5-ylmethyl)-2-oxo-2-(4-piperidin-4-yl-perhydro-1,4-diazepin-1-yl)-ethyl]-amide, 4-(2-oxo-1,2,4,5-tetrahydro-1,3-benzodiazepin-3-yl)-piperidine-1-carboxylic acid [2-[4-(4-fluoro-phenyl)-piperazin-1-yl]-1-(1H-indazol-5-ylmethyl)-2-oxo-ethyl]-amide, (30)

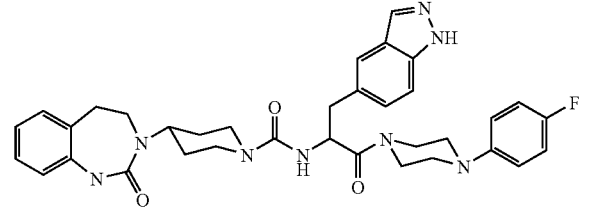

(31)

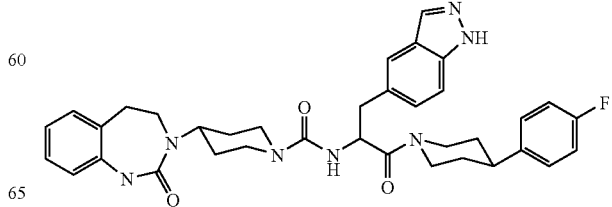

4-(2-oxo-1,2,4,5-tetrahydro-1,3-benzodiazepin-3-yl)-piperidine-1-carboxylic acid [2-[4-(4-fluoro-phenyl)-piperidin-1-yl]-1-(1H-indazol-5-ylmethyl)-2-oxo-ethyl]-amide, 4-(2-oxo-1,2,4,5-tetrahydro-1,3-benzodiazepin-3-yl)-piperidine-1-carboxylic acid [1-(1H-indazol-5-ylmethyl)-2-(1'-methanesulphonyl-4,4'-bipiperidinyl-1-yl)-2-oxo-ethyl]-amide,

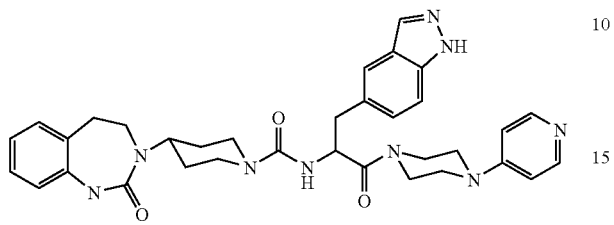
(32)

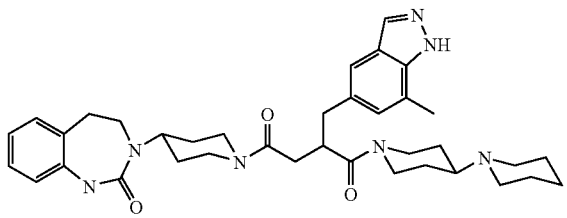
(35)

4-(2-oxo-1,2,4,5-tetrahydro-1,3-benzodiazepin-3-yl)-piperidine-1-carboxylic acid [1-(1H-indazol-5-ylmethyl)-2-oxo-2-(4-pyridin-4-yl-piperazin-1-yl)-ethyl]-amide,

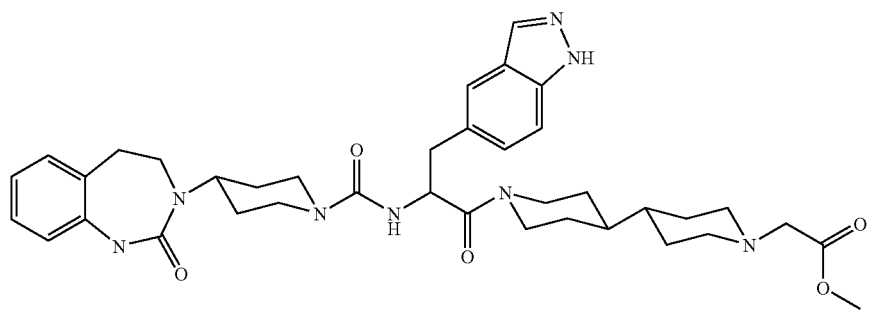
(33)

[1'-(3-(1H-indazol-5-yl)-2-{[4-(2-oxo-1,2,4,5-tetrahydro-1,3-benzodiazepin-3-yl)-piperidine-1-carbonyl]-amino}-propionyl)-4,4'-bipiperidinyl-1-yl]-acetate methyl,

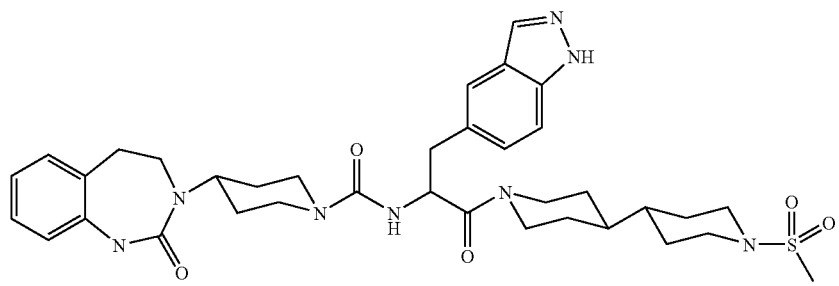
(34)

1-(1,4'-bipiperidinyl-1'-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,
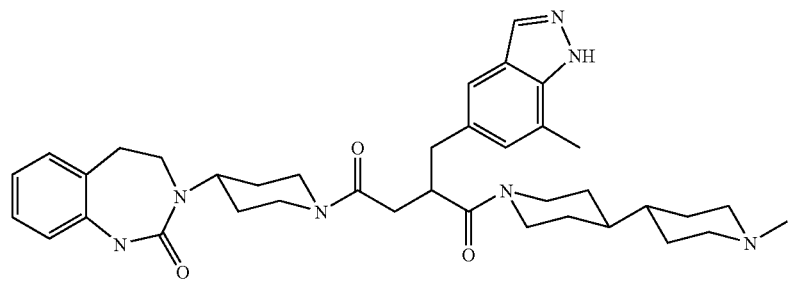
(36)
1-(1'-methyl-4,4'-bipiperidinyl-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,
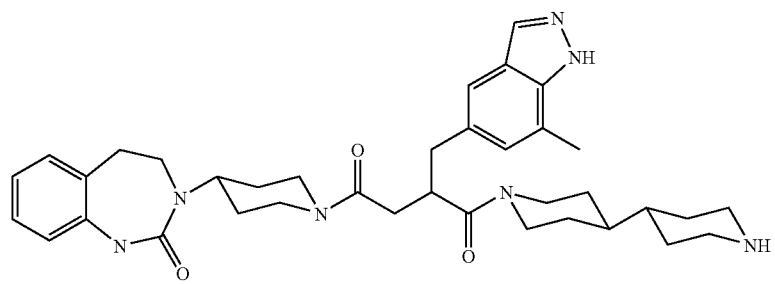
(37)
1-(4,4'-bipiperidinyl-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,
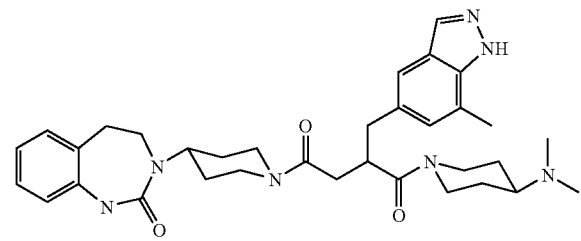
(38)

1-(4-dimethylamino-piperidin-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,
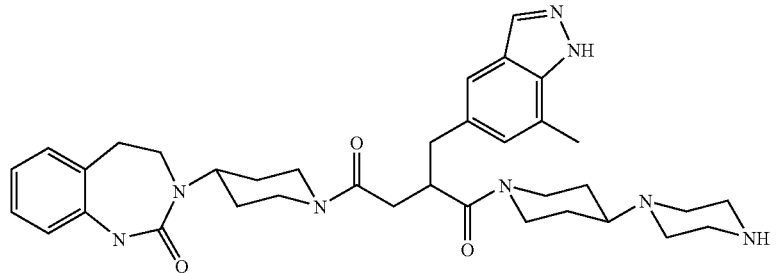
(40)
2-(7-methyl-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione,
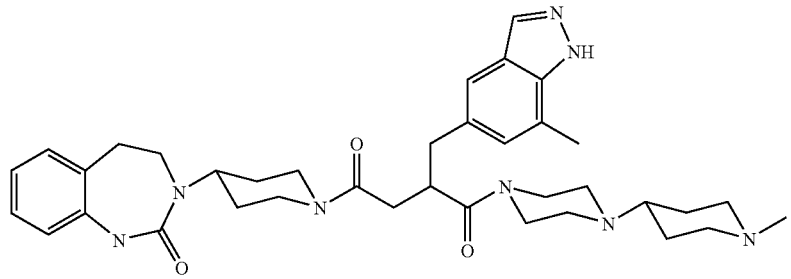
(41)
2-(7-methyl-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione,
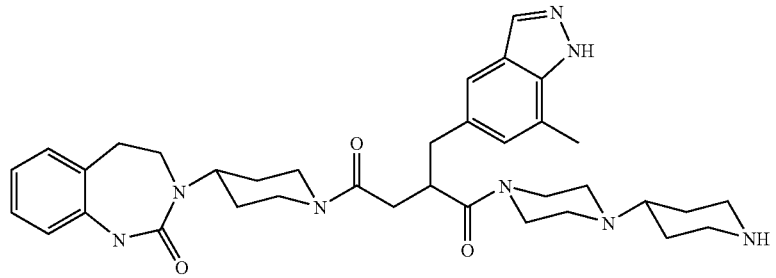
(42)

2-(7-methyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione,

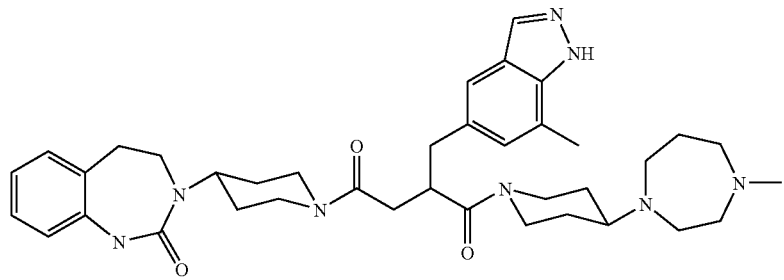

(43)

2-(7-methyl-1H-indazol-5-ylmethyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butane-1,4-dione,

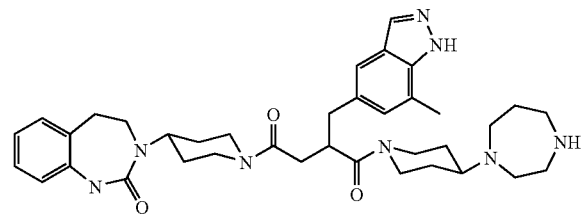

(44)

2-(7-methyl-1H-indazol-5-ylmethyl)-4-[4-(2-oxo-12,4,5-tetrahydro-1,3-benzodiazepin-3-yl)-piperidin-1-yl]-1-(4-perhydro-1,4-diazepin-1-yl-piperidin-1-yl)-butane-1,4-dione,

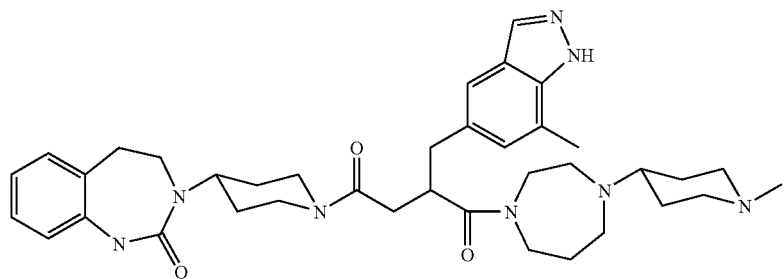

(45)

2-(7-methyl-1H-indazol-5-ylmethyl)-1-[4-(1-methyl-piperidin-4-yl)-perhydro-1,4-diazepin-1-yl]-4-[4-(2-oxo-1,2,4,5-tetrahydro-1,3-benzodiazepin-3-yl)-piperidin-1-yl]-butane-1,4-dione, (46)

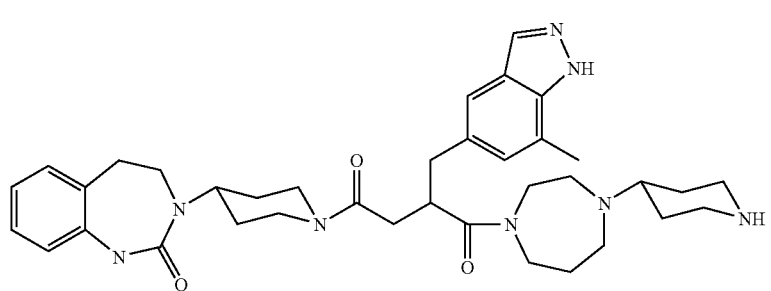

2-(7-methyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-perhydro-1,4-diazepin-1-yl)-butane-1,4-dione, (47)

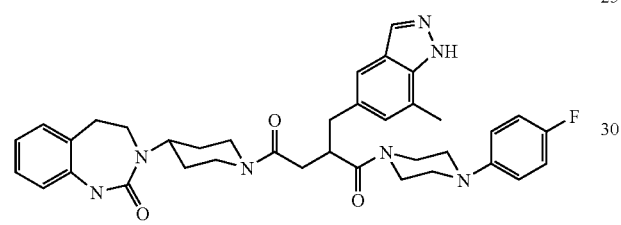

1-[4-(4-fluoro-phenyl)-piperazin-1-yl]-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione, (48)

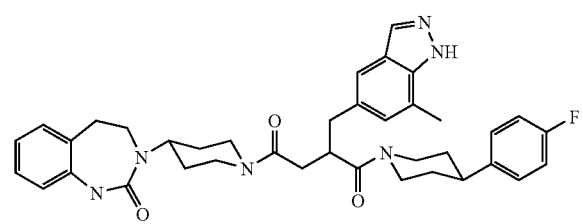

1-[4-(4-fluoro-phenyl)-piperidin-1-yl]-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione, (49)

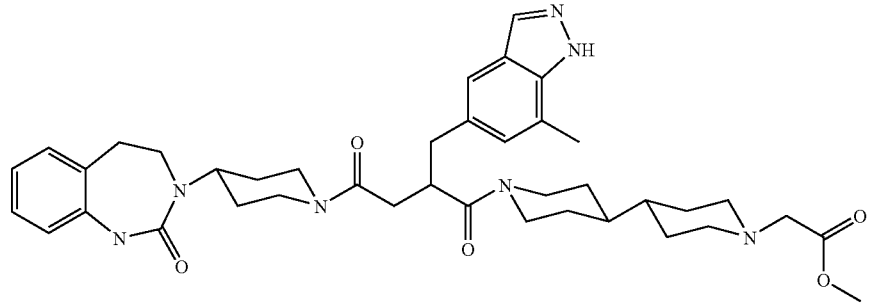

2-(7-methyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (50)

methyl (1'-{2-(7-methyl-1H-indazol-5-ylmethyl)-4-oxo-4-[4-(2-oxo-1,2,4,5-tetrahydro-1,3-benzodiazepin-3-yl)-piperidin-1-yl]-butyryl}-4,4'-bipiperidinyl-1-yl)-acetate,

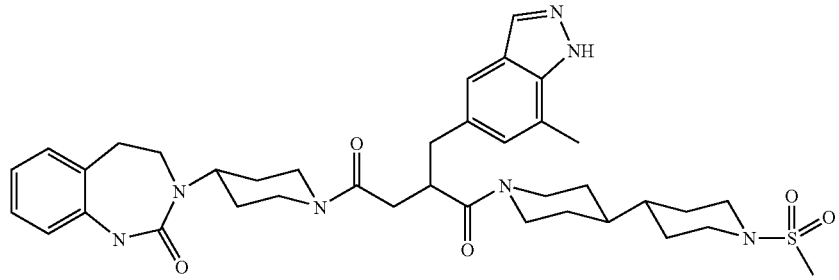

(51)

1-(1'-methanesulphonyl-4,4'-bipiperidinyl-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

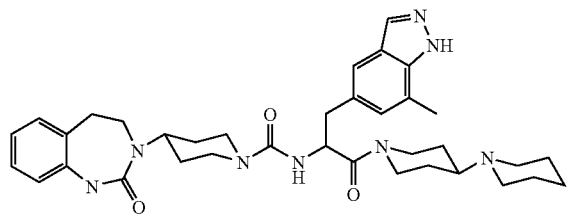

(52)

4-(2-oxo-1,2,4,5-tetrahydro-1,3-benzodiazepin-3-yl)-piperidine-1-carboxylic acid [2-(1,4'-bipiperidinyl-1'-yl)-1-(7-methyl-1H-indazol-5-ylmethyl)-2-oxo-ethyl]-amide,

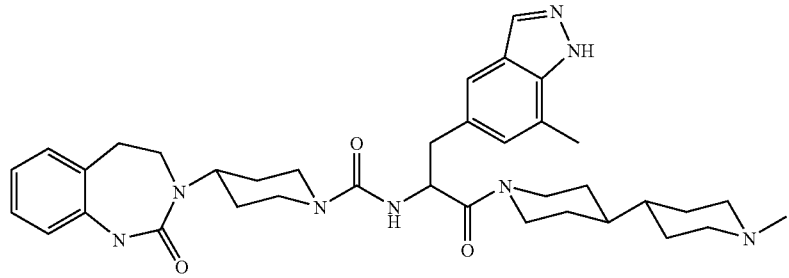

(53)

4-(2-oxo-1,2,4,5-tetrahydro-1,3-benzodiazepin-3-yl)-piperidine-1-carboxylic acid [2-(1'-methyl-4,4'-bipiperidinyl-1-yl)-1-(7-methyl-1H-indazol-5-ylmethyl)-2-oxo-ethyl]-amide,

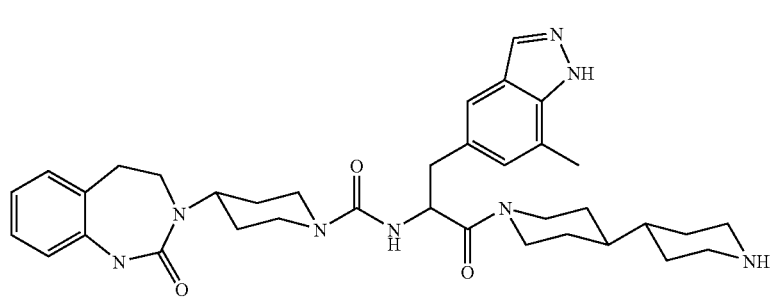

(54)

4-(2-oxo-1,2,4,5-tetrahydro-1,3-benzodiazepin-3-yl)-piperidine-1-carboxylic acid [2-(4,4'-bipiperidinyl-1-yl)-1-(7-methyl-1H-indazol-5-ylmethyl)-2-oxo-ethyl]-amide,

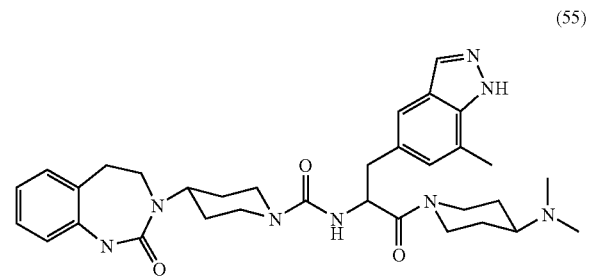

(55)

4-(2-oxo-1,2,4,5-tetrahydro-1,3-benzodiazepin-3-yl)-piperidine-1-carboxylic acid [2-(4-dimethylamino-piperidin-1-yl)-1-(7-methyl-1H-indazol-5-ylmethyl)-2-oxo-ethyl]-amide,

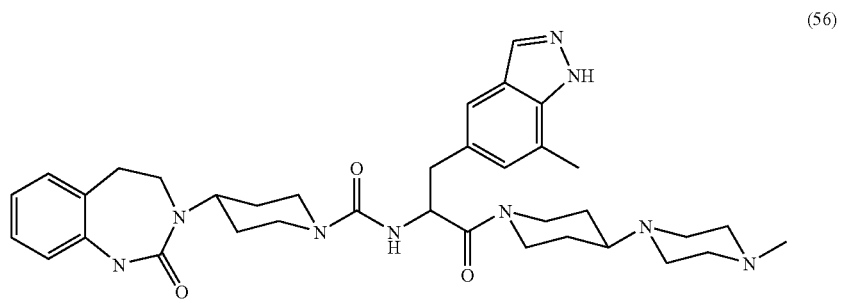

(56)

4-(2-oxo-1,2,4,5-tetrahydro-1,3-benzodiazepin-3-yl)-piperidine-1-carboxylic acid {1-(7-methyl-1H-indazol-5-ylmethyl)-2-[4-(4-methyl-piperazin-1-yl)-piperidin-1-yl]-2-oxo-ethyl}-amide,

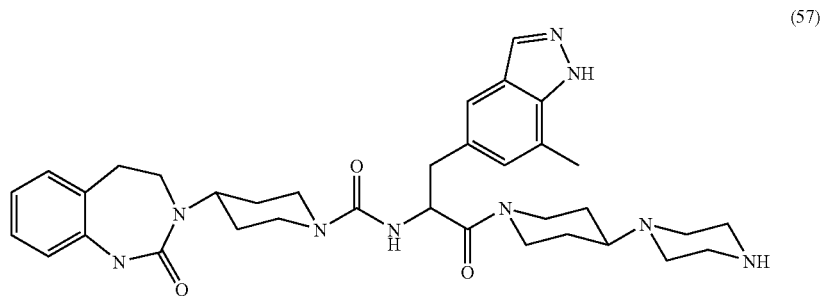

(57)

4-(2-oxo-1,2,4,5-tetrahydro-1,3-benzodiazepin-3-yl)-piperidine-1-carboxylic acid [1-(7-methyl-1H-indazol-5-ylmethyl)-2-oxo-2-(4-piperazin-1-yl)-piperidin-1-yl)-ethyl]-amide,

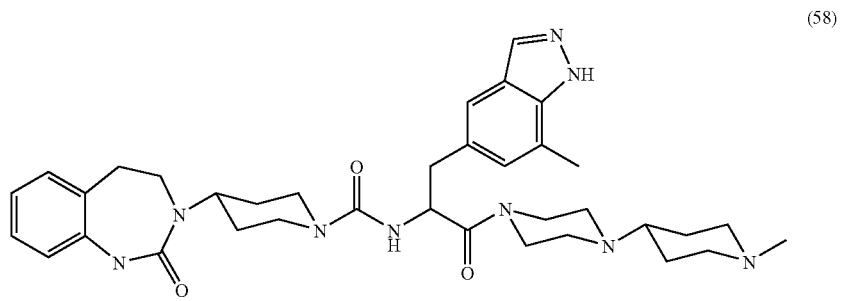

(58)

4-(2-oxo-1,2,4,5-tetrahydro-1,3-benzodiazepin-3-yl)-piperidine-1-carboxylic acid {1-(7-methyl-1H-indazol-5-ylmethyl)-2-[4-(1-methyl-piperidinn-4-yl)-piperazin-1-yl]-2-oxo-ethyl}-amide,

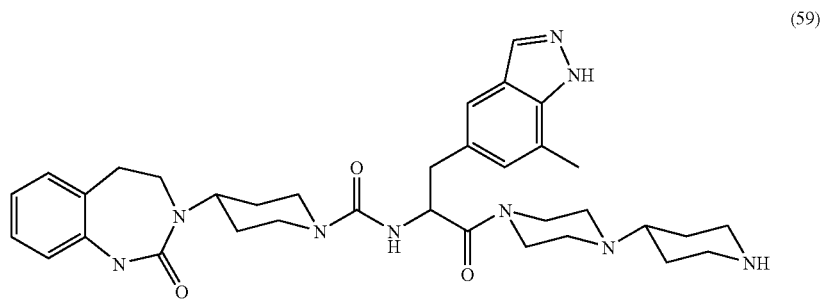

(59)

4-(2-oxo-1,2,4,5-tetrahydro-1,3-benzodiazepin-3-yl)-piperidine-1-carboxylic acid [1-(7-methyl-1H-indazol-5-ylmethyl)-2-oxo-2-(4-piperidin-4-yl)-piperazin-1-yl)-ethyl]-amide,

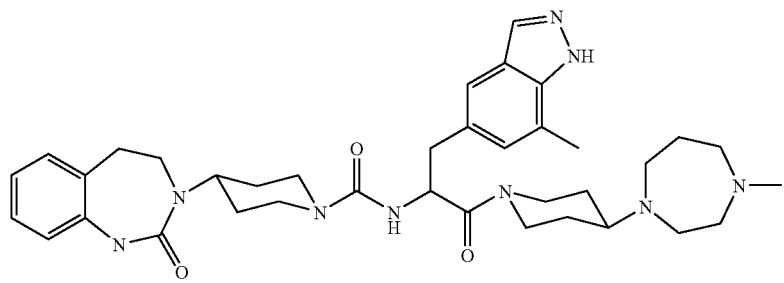
(60)

4-(2-oxo-1,2,4,5-tetrahydro-1,3-benzodiazepin-3-yl)-piperidine-1-carboxylic acid {1-(7-methyl-1H-indazol-5-ylmethyl)-2-[4-(4-methyl-perhydro-1,4-diazepin-1-yl)-piperidin-1-yl]-2-oxo-ethyl}-amide,

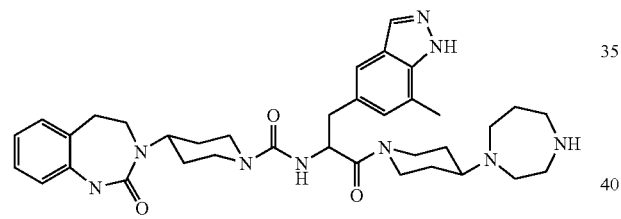
(61)

4-(2-oxo-1,2,4,5-tetrahydro-1,3-benzodiazepin-3-yl)-piperidine-1-carboxylic acid [1-(7-methyl-1H-indazol-5-ylmethyl)-2-oxo-2(4-perhydro-1,4-diazepin-1-yl-piperidin-1-yl)-ethyl]-amide,

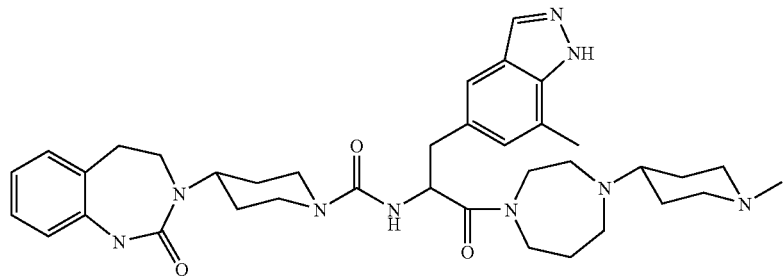
(62)

4-(2-oxo-1,2,4,5-tetrahydro-1,3-benzodiazepin-3-yl)-piperi-
dine-1-carboxylic acid {1-(7-methyl-1H-indazol-5-ylm-
ethyl)-2[4-(methyl-piperidin-4-yl)-perhydro-1,4-diaz-
epin-1yl]-2-oxo-ethyl}-amide, 4-(2-oxo-1,2,4,5-tetrahydro-1,3-benzodiazepin-3-yl)-piperi-
dine-1-carboxylic acid [2-[4-(4-fluoro-phenyl)-piperzin-
1-yl]-1-(7-methyl-1H-indazol-5-ylmethyl)-2-oxo-ethyl]-
amide,

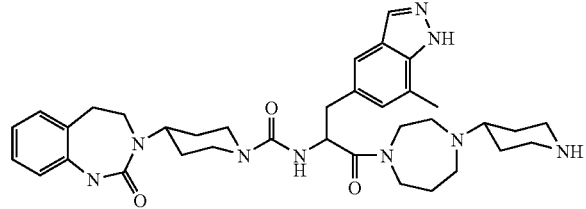

(63)

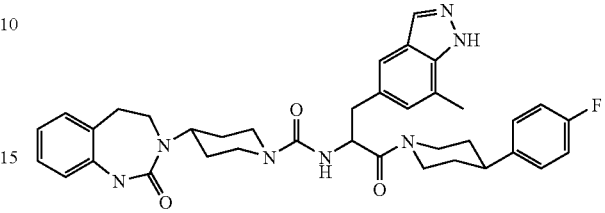

(65)

4-(2-oxo-1,2,4,5-tetrahydro-1,3-benzodiazepin-3-yl)-piperi-
dine-1-carboxylic acid [1-(7-methyl-1H-indazol-5-ylm-
ethyl)-2-oxo-2(4-piperidin-4-perhydro-1,4-diazepin-1-
yl)-ethyl]-amide, 4-(2-oxo-1,2,4,5-tetrahydro-1,3-benzodiazepin-3-yl)-piperi-
dine-1-carboxylic acid [2-[4-(4-fluoro-phenyl)-piperidin-
1-yl]-1-(7-methyl-1H-indazol-5-ylmethyl)-2-oxo-ethyl]-
amide,

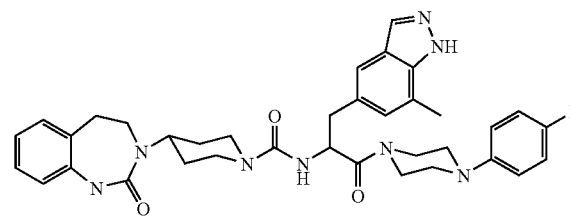

(64)

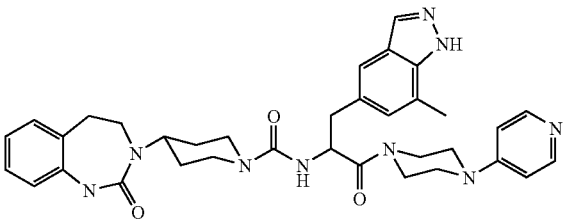

(66)

4-(2-oxo-1,2,4,5-tetrahydro-1,3-benzodiazepin-3-yl)-piperi-
dine-1-carboxylic acid [1-(7-methyl-1H-indazol-5-ylm-
ethyl)-2-oxo-2-(4-pyridin-4yl-piperazin-1-yl)-ethyl]-
amide,

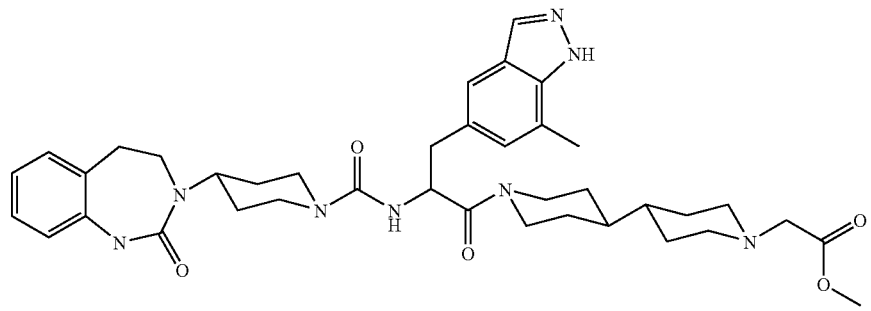

(67)

methyl [1'-(3-(7-methyl-1H-indazol-5-yl)-2-{[4-(2-oxo-1,2,4,5-tetrahydro-1,3-benzodiazepin-3-yl)-piperidine-1-carbonyl]-amino}-propionyl)-4,4'-bipiperidinyl-1-yl]-acetate,

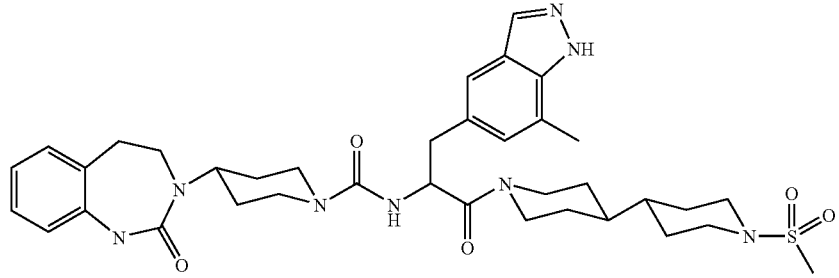
(68)

4-(2-oxo-1,2,4,5-tetrahydro-1,3-benzodiazepin-3-yl)-piperidine-1-carboxylic acid [2-(1'-methanesulphonyl-4,4'-bipiperidinyl-1-yl)-1-(7-methyl-1H-indazol-5-ylmethyl)-2-oxo-ethyl]-amide,

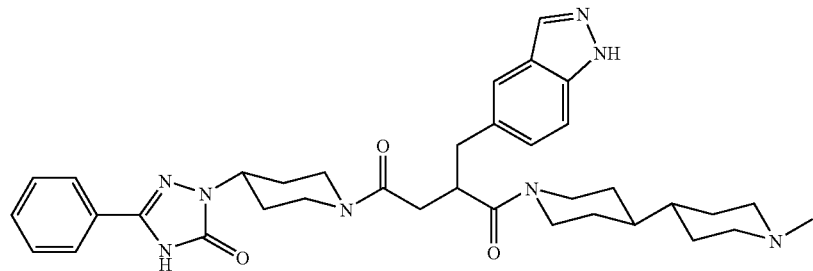
(69)

2-(1H-indazol-5-ylmethyl)-1-(1'-methyl-4,4'-bipiperidinyl-1-yl)-4-[4-(5-oxo-3phenyl-4,5-dihydro-1,2,4-triazol-1-yl)-piperidin-1-yl]-butane-1,4-dione,

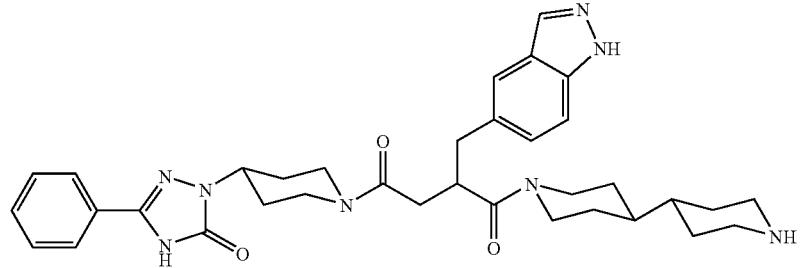
(70)

1-(4,4'-bipiperidinyl-1-yl)-2-(1H-indazol-5-ylmethyl)-4-[4-(5-oxo-3-phenyl-4,5- dihydro-1,2,4-triazol-1-yl)-piperidin-1-yl]-butane-1,4-dione,
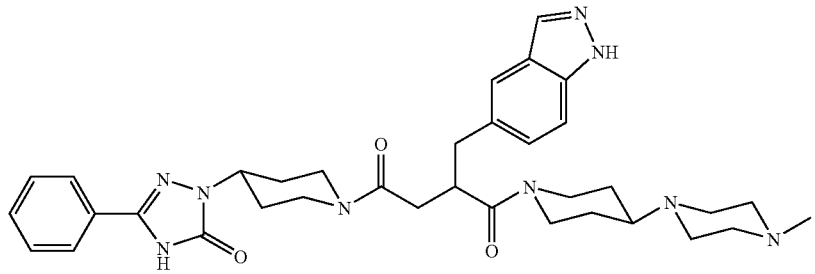
(71)
2-(1H-indazol-5-ylmethyl)-1-[4-(4-methyl-piperazin-1-yl)-piperidin-1-yl]-4-[4- (5-oxo-3-phenyl-4,5-dihydro-1,2,4-triazol-1-yl)-piperidin-1-yl]-butane-1,4-dione,
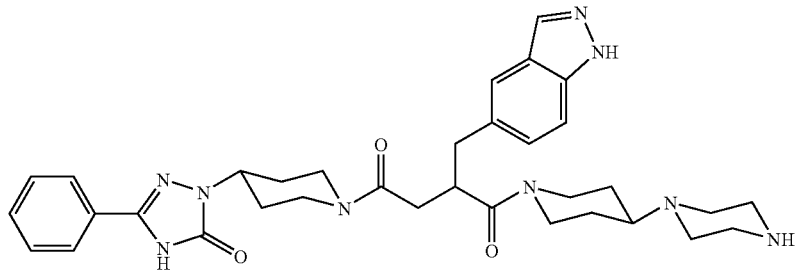
(72)
2-(1H-indazol-5-ylmethyl)-4-[4-(5-oxo-3-phenyl-4,5-dihydro-1,2,4-triazol-1-yl)- piperidin-1-yl]-1(4-piperazin-1yl-piperidin-1-yl)butane-1,4-dione,
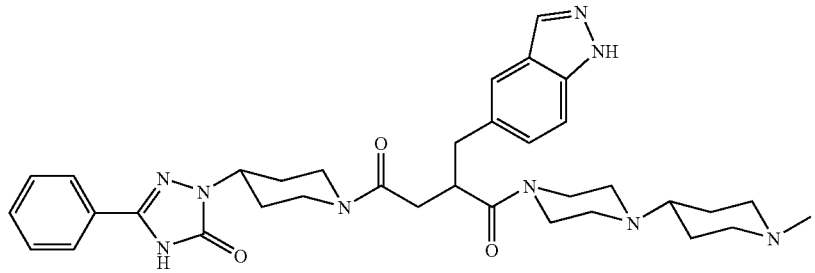
(73)

2-(1H-indazol-5-ylmethyl)-1-[4-(1-methyl-piperidin-4-yl)-piperazin-1-yl]-4-[4- (5-oxo-3-phenyl-4,5-dihydro-1,2,4-triazol-1-yl)-piperidin-1-yl]-butane-1,4-dione,
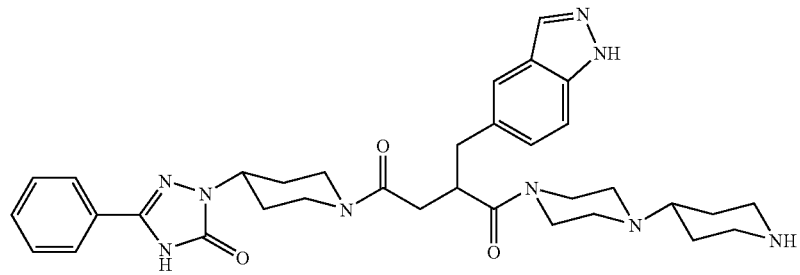
(74)
2-(1H-indazol-5-ylmethyl)-4-[4-(5-oxo-3-phenyl-4,5-dihydro-1,2,4-triazol-1-yl)- piperidin-1-yl]-1(4-piperidin-4yl-piperazin-1-yl)butane-1,4-dione,
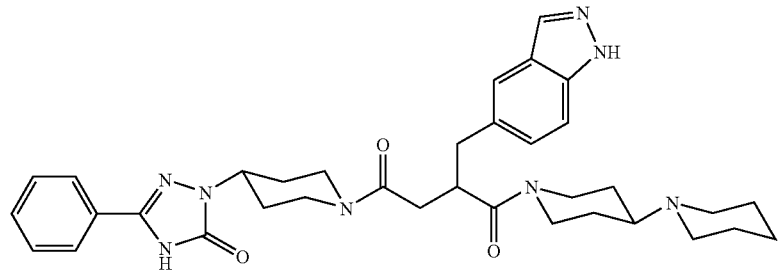
(75)
1-(1,4'-bipiperidinyl-1'-yl)-2-(1H-indazol-5-ylmethyl)-4-[4-(5-oxo-3-phenyl-4,5- dihydro-1,2,4-triazol-1-yl)-piperidin-1-yl]-butane-1,4-dione,
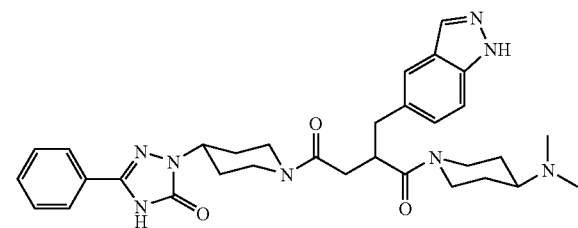
(76)

1-(4-dimethylamino-piperidin-1-yl)-2-(1H-indazol-5-ylm-ethyl)-4-[4-(5-oxo-3- phenyl-4,5-dihydro-1,2,4-triazol-1-yl)-piperidin-1-yl]-butane-1,4-dione,
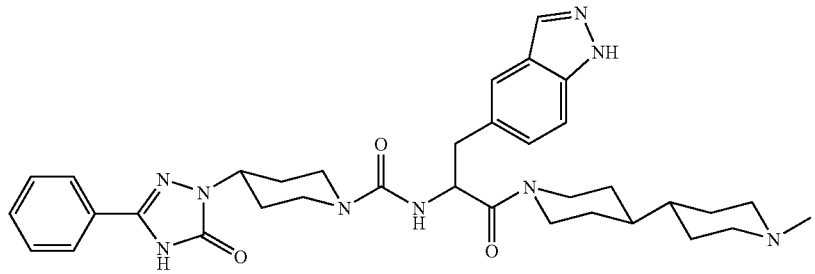
(77)
4-(5-oxo-3-phenyl-4,5-dihydro-1,2,4-triazol-1yl)-piperidine-1-carboxylic acid [1-(1H-indazol-5-ylmethyl)-2-(1'-methyl-4,4'-bipiperidinyl-1-yl)-2-oxo-ethyl]-amide,
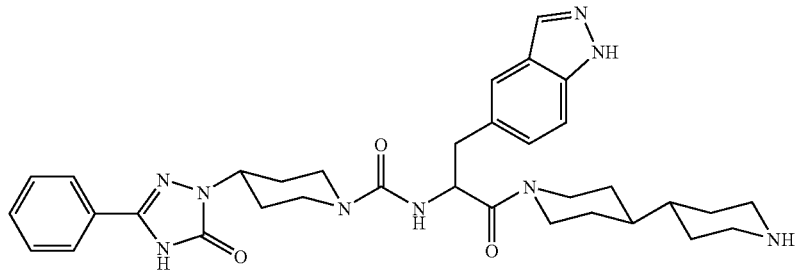
(78)
4-(5-oxo-3-phenyl-4,5-dihydro-1,2,4-triazol-1yl)-piperidine-1-carboxylic acid [2-(4,4'-bipiperidinyl-1-yl)-1-(1H-indazol-5-ylmethyl)_2-oxo-ethyl]-amide,
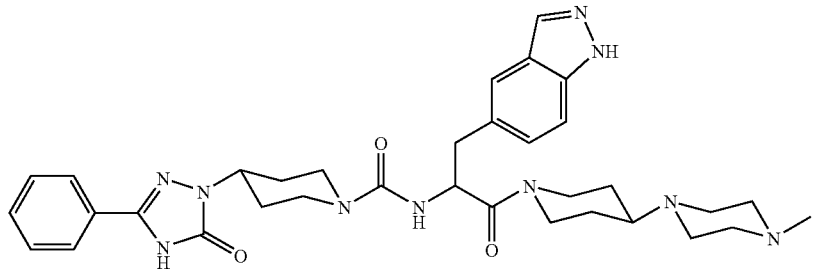
(79)

4-(5-oxo-3-phenyl-4,5-dihydro-1,2,4-triazol-1yl)-piperidine-1-carboxylic acid {1-(1H-indazol-5-ylmethyl)-2-[(4-(4-methyl-piperazin-1-yl)-piperidin-1-yl]-2-oxo-ethyl}-amide,

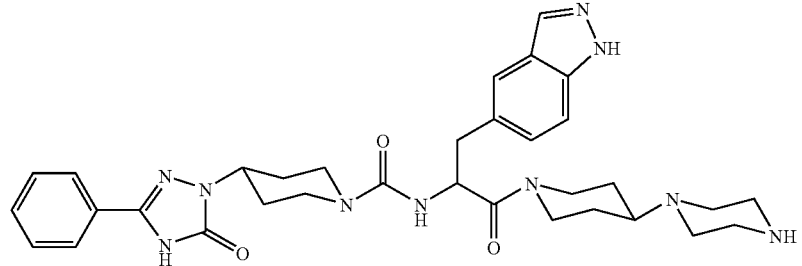
(80)

4-(5-oxo-3-phenyl-4,5-dihydro-1,2,4-triazol-1yl)-piperidine-1-carboxylic acid [1-(1H-indazol-5-ylmethyl)-2-oxo-2-(4-piperazin-1-yl-piperidin-1yl)-ethyl]-amide,

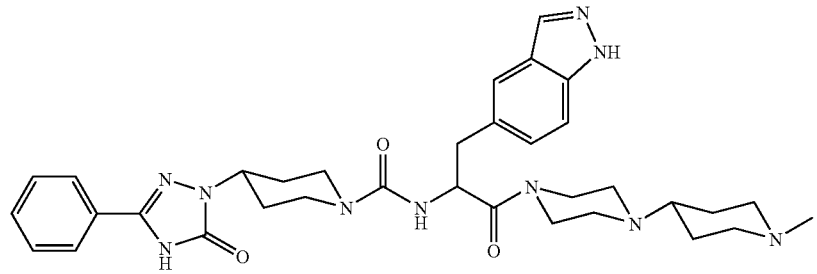
(81)

4-(5-oxo-3-phenyl-4,5-dihydro-1,2,4-triazol-1yl)-piperidine-1-carboxylic acid {1-(1H-indazol-5-ylmethyl)-2-[4-(1-methyl-piperidin-4-yl)-piperazin-1-yl]-2-oxo-ethyl}-amide,

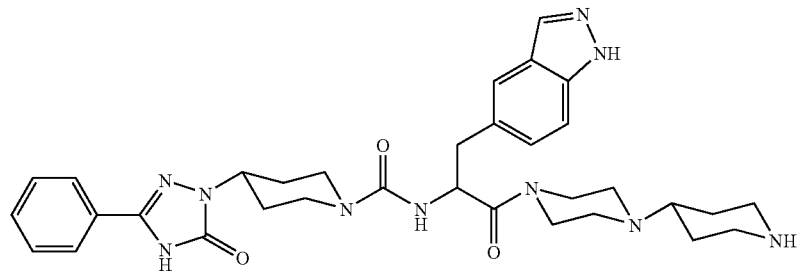
(82)

4-(5-oxo-3-phenyl-4,5-dihydro-1,2,4-triazol-1yl)-piperidine-1-carboxylic acid [1-(1H-indazol-5-ylmethyl)-2-oxo-2-(4-piperidin-4-yl)-piperazin-1-yl)-ethyl}-amide,
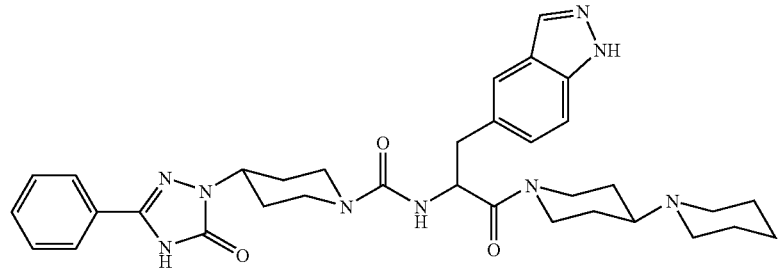
(83)
4-(5-oxo-3-phenyl-4,5-dihydro-1,2,4-triazol-1yl)-piperidine-1-carboxylic acid [2-(1,4'-bipiperidinyl-1'-yl)-1-(1H-indazol-5-ylmethyl)-2-oxo-ethyl]-amide,
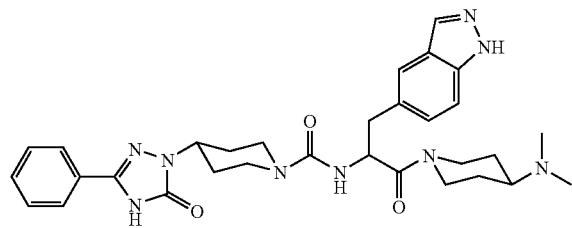
(84)
4-(5-oxo-3-phenyl-4,5-dihydro-1,2,4-triazol-1yl)-piperidine-1-carboxylic acid [2-(4-dimethylamino-piperidin-1yl)-1-(1H-indazol-5-ylmethyl)-2-oxo-ethyl]-amide,
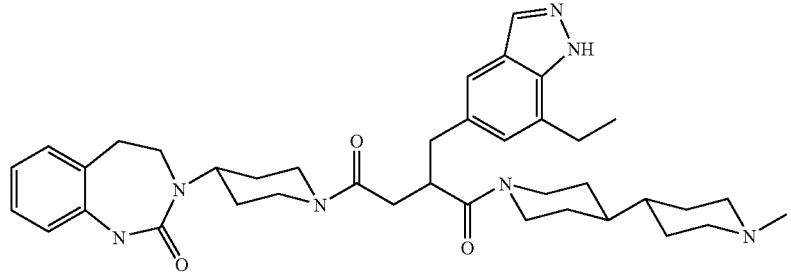
(85)

2-(7-ethyl-1H-indazol-5-ylmethyl)-1-(1'-methyl-4,4'-bipiperidinyl-1-yl)-4-[4-(2- oxo-1,2,4,5-tetrahydro-1,3-benzodiazepin-3-yl)-piperidin-1-yl]-butane-1,4-dione,
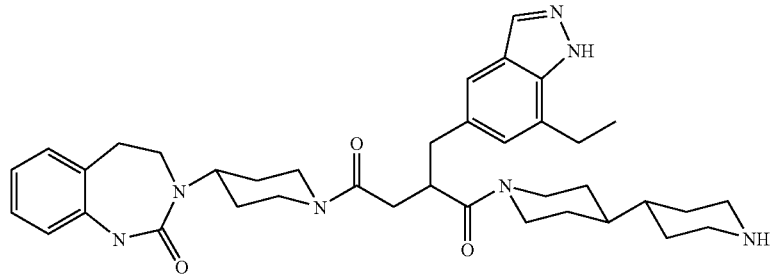
(86)
1-(4,4'-bipiperidinyl-1-yl)-2-(7-ethyl-1H-indazol-5-ylmethyl)-4-[4-(2-oxo- 1,2,4,5-tetrahydro-1,3-benzodiazepin-3-yl)-piperidin-1-yl]-butane-1,4-dione,
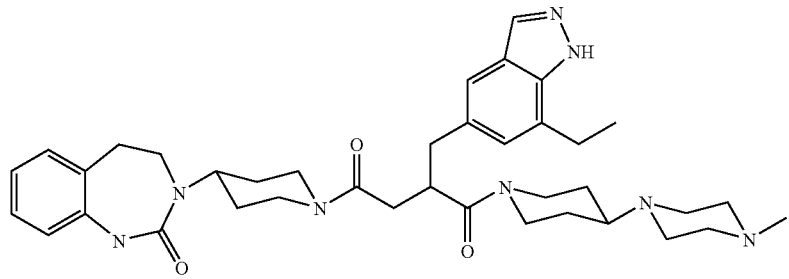
(87)
2-(7-ethyl-1H-indazol-5-ylmethyl)-1-[4-(4-methyl-piperazin-1-yl)piperidin-1- yl]-4-[4-(2-oxo-1,2,4,5-tetrahydro-1,3-benzodiazepin-3-yl)-piperidin-1-yl]-butane-1,4-dione,
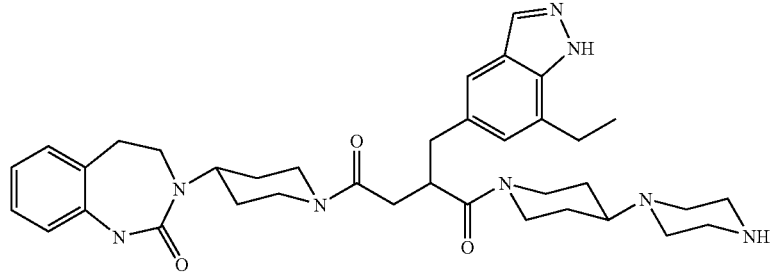
(88)

2-(7-ethyl-1H-indazol-5-ylmethyl)-4-[4-(2-oxo-1,2,4,5-tetrahydro-1,3- benzodiazepin-3-yl)-piperidin-1-yl]-1-(4-piperazin-1yl-piperidin-1-yl)-butane-1,4-dione,
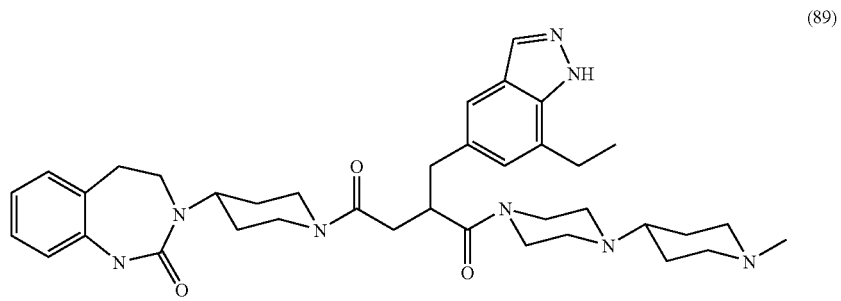
(89)
2-(7-ethyl-1H-indazol-5-ylmethyl)-1-[4-(1-methyl-piperidin-4-yl)piperazin-1- yl]-4-[4-(2-oxo-1,2,4,5-tetrahydro-1,3-benzodiazepin-3-yl)-piperidin-1-yl]-butane-1,4-dione,
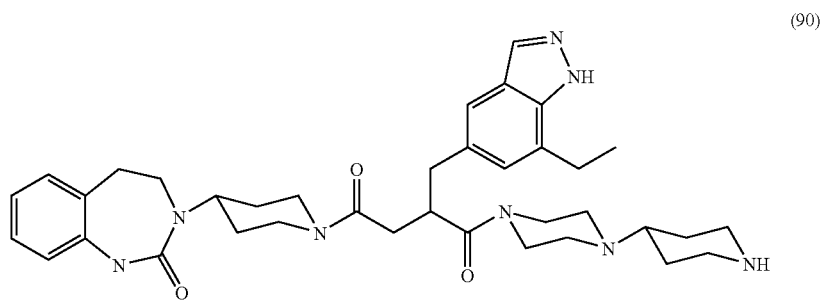
(90)
2-(7-ethyl-1H-indazol-5-ylmethyl)-4-[4-(2-oxo-1,2,4,5-tetrahydro-1,3- benzodiazepin-3-yl)-piperidin-1-yl]-1-(4-piperidin-4yl-piperazin-1-yl)-butane-1,4-dione,
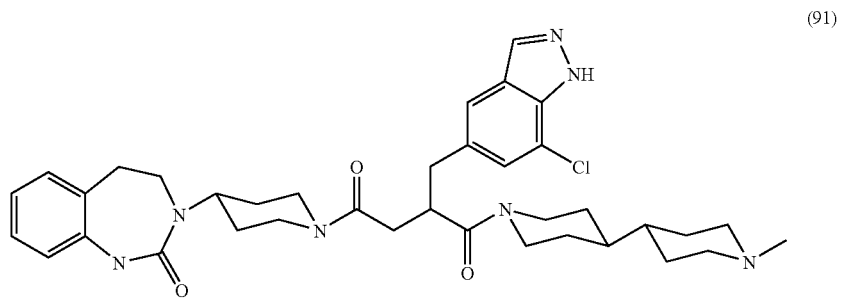
(91)

2-(7-chloro-1H-indazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione,
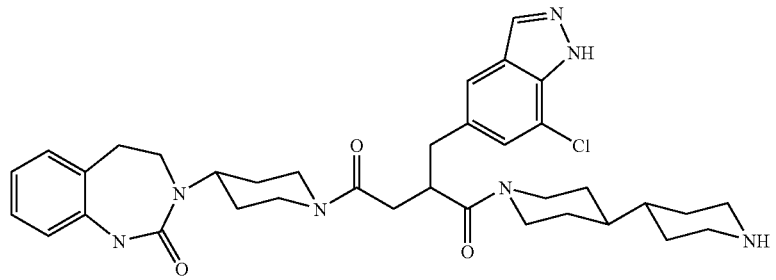
(92)
1-(4,4'-bipiperidinyl-1-yl)-2-(7-chloro-1H-indazol-5-ylmethyl)-4-[4-(2-oxo- 1,2,4,5-tetrahydro-1,3-benzodiazepin-3-yl)-piperidin-1-yl]-butane-1,4-dione,
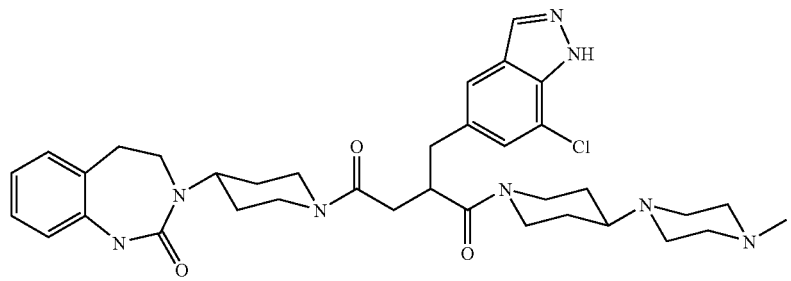
(93)
2-(7-chloro-1H-indazol-5-ylmethyl)-1-[4(4-methyl-piperazin-1-yl)-piperidin-1- yl]-4-[4-(2-oxo-1,2,4,5-tetrahydro-1,3-benzodiazepin-3-yl)-piperidin-1-yl]-butane-1,4-dione,
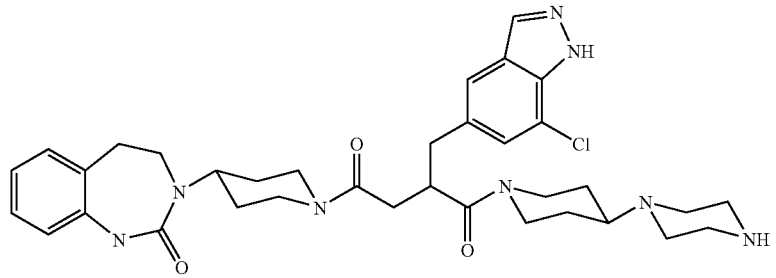
(94)

2-(7-chloro-1H-indazol-5-ylmethyl)-4-[4(2-oxo-1,2,4,5-tet-rahydro-1,3- benzodiazepin-3-yl)-piperidin-1-yl]-1-(4-piperazin-1-yl-piperidin-1-yl)-butane-1,4-dione,
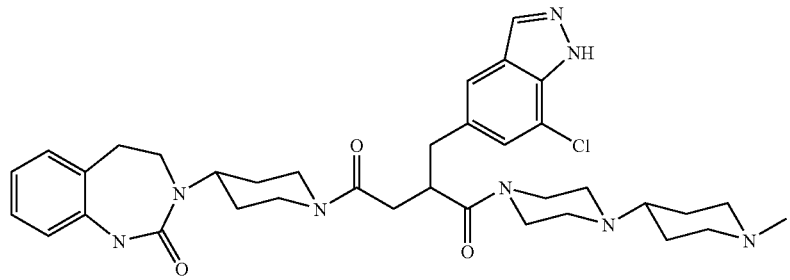
(95)
2-(7-chloro-1H-indazol-5-ylmethyl)-1-[4-(1-methyl-piperidin-4-yl)-piperazin-1- yl]-4-[4-(2-oxo-1,2,4,5-tetrahydro-1,3-benzodiazepin-3-yl)-piperidin-1-yl]-butane-1,4-dione,
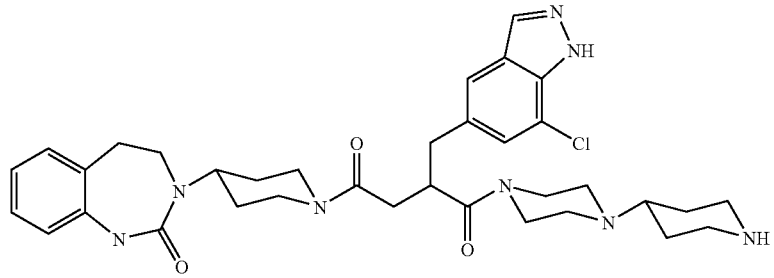
(96)
2-(7-chloro-1H-indazol-5-ylmethyl)-4-[4(2-oxo-1,2,4,5-tet-rahydro-1,3- benzodiazepin-3-yl)-piperidin-1-yl]-1-(4-piperidin-4-yl-piperazin-1-yl)-butane-1,4-dione,
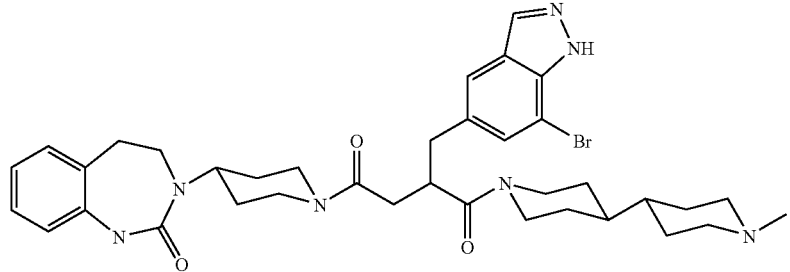
(97)

2-(7-bromo-1H-indazol-5-ylmethyl)-1-(1'-methyl-4,4'-bipi-
peridinyl-1yl)-4-[4-(2- oxo-1,2,4,5-tetrahydro-1,3-benzo-
diazepin-3-yl)-piperidin-1-yl]-butane-1,4-dione,
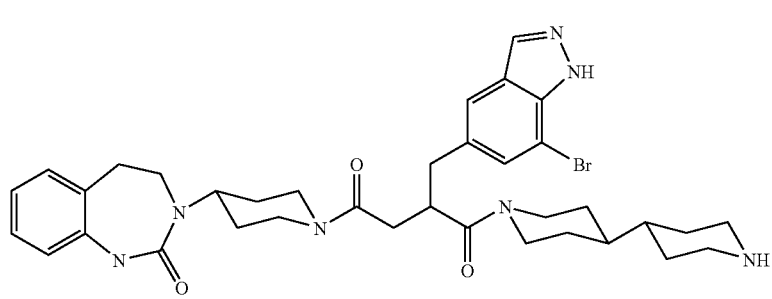
(98)
1-(4,4'-bipiperidinyl-1-yl)-2-(7-bromo-1H-indazol-5-ylm-
ethyl)-4-[4-(2-oxo- 1,2,4,5-tetrahydro-1,3-benzodiaz-
epin-3-yl)-piperidin-1-yl]-butane-1,4-dione,
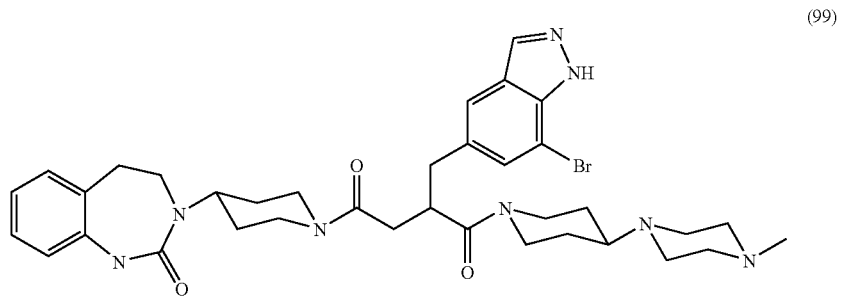
(99)
2-(7-bromo-1H-indazol-5-ylmethyl)-1-(4-methyl-piperazin-
1yl)-piperidin-1-yl]- 4,-[4-(2-oxo-1,2,4,5-tetrahydro-1,3-
benzodiazepin-3-yl)-piperidin-1-yl]-butane-1,4-dione,
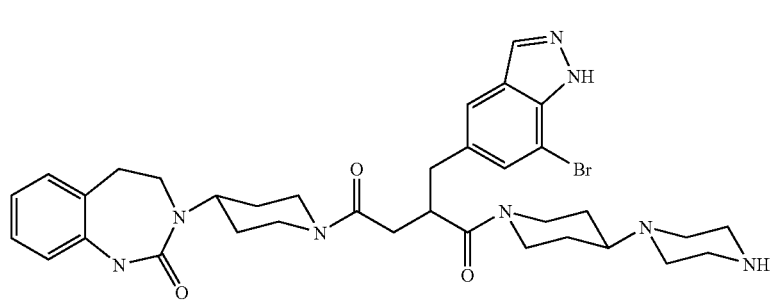
(100)

2-(7-bromo-1H-indazol-5-ylmethyl)-4-[4-oxo-1,2,4,5-tetrahydro-1,3- benzodiazepin-3-yl)-piperidin-1-yl]-1-(4-piperazin-1yl-piperidin-1-yl)-butane-1,4-dione,
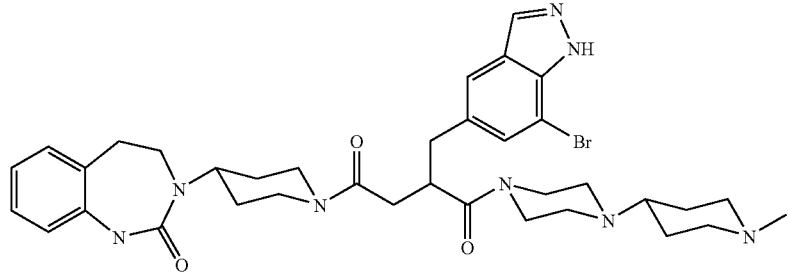
(101)
2-(7-bromo-1H-indazol-5-ylmethyl)-1-[4-methyl-piperidin-4yl)-piperazin-1-yl]- 4,-[4-(2-oxo-1,2,4,5-tetrahydro-1,3-benzodiazepin-3-yl)-piperidin-1-yl]-butane-1,4-dione,
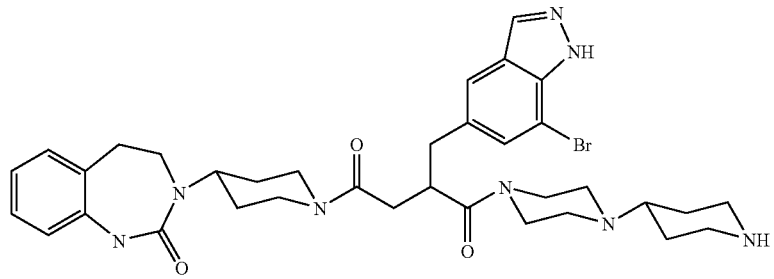
(102)
2-(7-bromo-1H-indazol-5-ylmethyl)-4-[4-(2-oxo-1,2,4,5-tetrahydro-1,3- benzodiazepin-3-yl)-piperidin-1-yl]-1-(4-piperidin-4yl-piperazin-1-yl)-butane-1,4-dione,
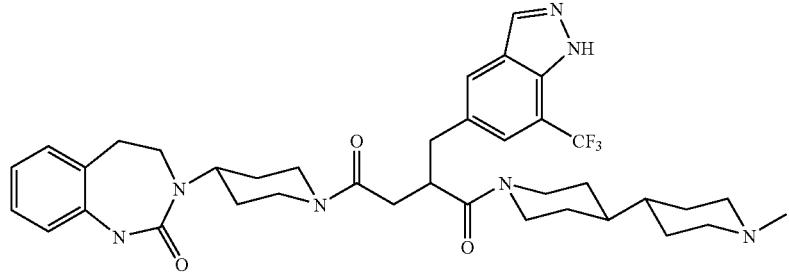
(103)

1-(1'-methyl-4,4'-bipiperidinyl-1-yl)-4[4(2-oxo-1,2,4,5-tetrahydro-1,3-benzodiazepin-3-yl)-piperidin-1yl]-2-(7-trifluoromethyl-1H-indazol-5-ylmethyl)-butane-1,4-dione,

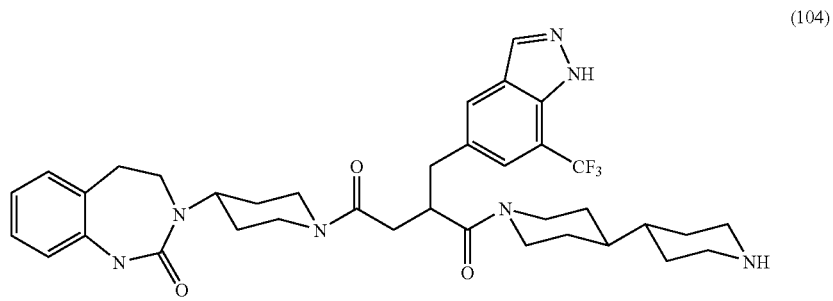

(104)

1-(4,4'-bipiperidynyl-1-yl)-4-[4-(2-oxo-1,2,4,5-tetrahydro-1,3-benzodiazepin-3-yl)-piperidin-1-yl]-2-(7-trifluoromethyl-1H-indazol-5-ylmethyl)-butane-1,4-dione,

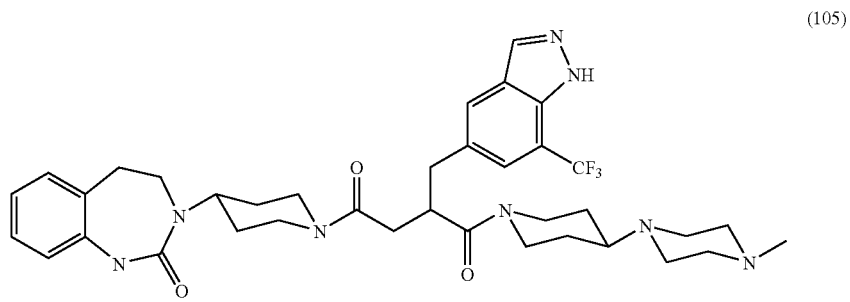

(105)

2-(7-methyl-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione,

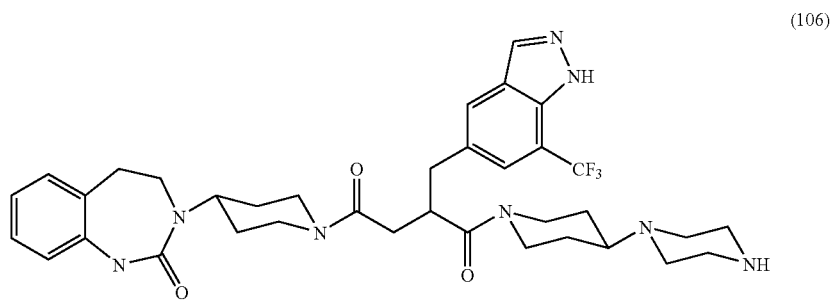

(106)

4-[4(2-oxo-1,2,4,5-tetrahydro-1,3-benzodiazepin-3-yl)-piperidin-1-yl]-1-(4- piperazin-1-yl-piperidin-1yl)-2-(7-trifluoromethyl-1H-indazol-5-ylmethyl)-butane-1,4-dione,

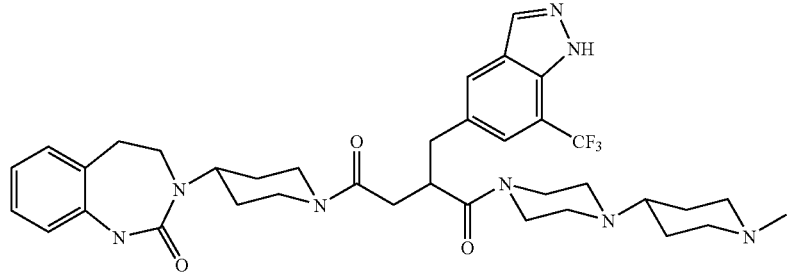

(107)

1-[4-(methyl-piperidin-4-yl)-piperazin-1yl]-4-[4-(2-oxo-1,2,4,5-tetrahydro-1,3- benzodiazepin-3-yl)-piperidin-1yl]-2-(7-trifluoromethyl-1H-indazol-5-ylmethyl)-butane-1,4-dione,

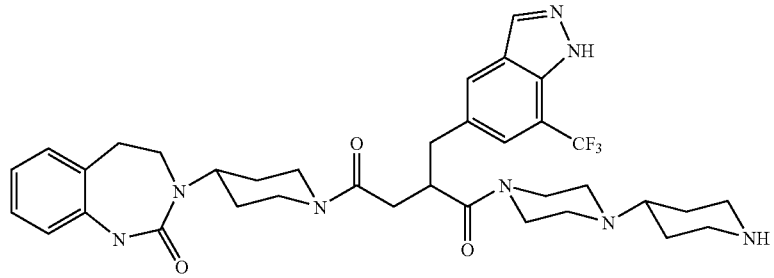

(108)

4-[4(2-oxo-1,2,4,5-tetrahydro-1,3-benzodiazepin-3-yl)-piperidin-1-yl]-1-(4- piperidin-4-yl-piperazin-1yl)-2-(7-trifluoromethyl-1H-indazol-5-ylmethyl)-butane-1,4-dione,

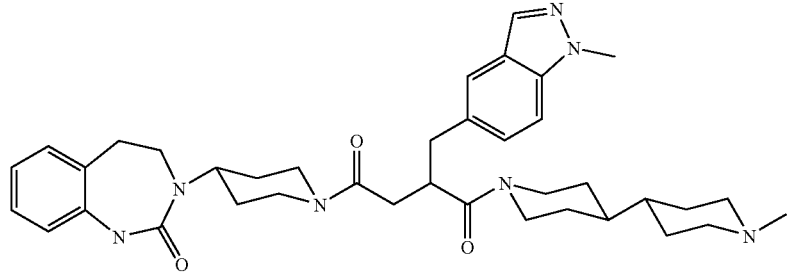

(109)

1-(1'-methyl-4,4'-bipiperidinyl-1-yl)-2-(1-methyl-1H-indazol-5-ylmethyl)-4-[4- (2-oxo-1,2,4,5-tetrahydro-1,3-benzodiazepin-3-yl)-piperidin-1yl]-butane-1,4-dione,
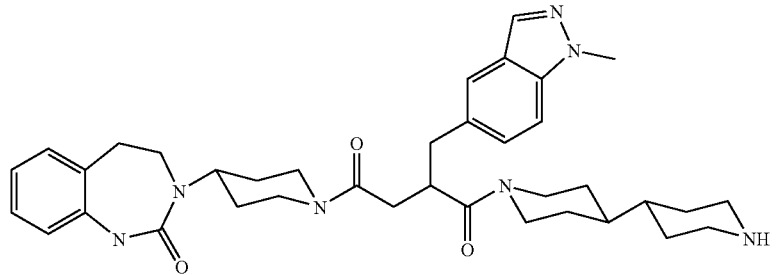
(110)
1-(4,4'-bipiperidinyl-1-yl)-2-(1-methyl-1H-indazol-5-ylmethyl)-4-[4- (2-oxo-1,2,4,5-tetrahydro-1,3-benzodiazepin-3-yl)-piperidin-1yl]-butane-1,4-dione,
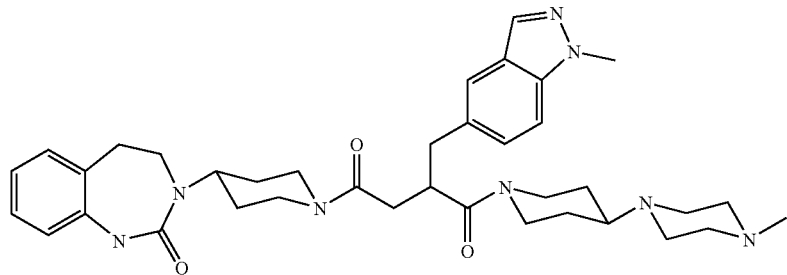
(111)
2-(1-methyl-1H-indazol-5-ylmethyl)-1-[4-(4-methyl-piperazin-1-yl)-piperidin-1- yl]-4-[4-(2-oxo-1,2,4,5-tetrahydro-1,3-benzodiazepin-3-yl)-piperidin-1-yl]-butane-1,4-dione,
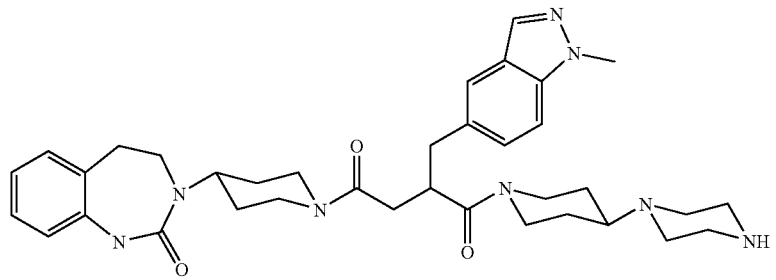
(112)

2-(1-methyl-1H-indazol-5-ylmethyl)-4-[4-(2-oxo-1,2,4,5-tetrahydro-1,3- benzodiazepin-3-yl)-piperidin-1-yl]-1-(4-piperazin-1yl-piperidin-1-yl)-butane-1,4-dione,
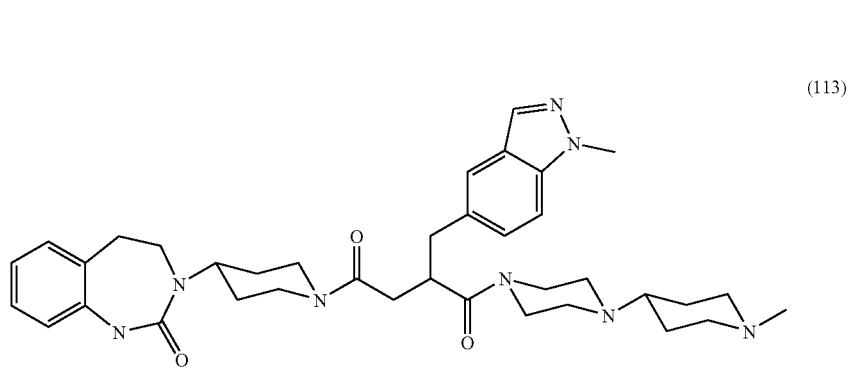
(113)
2-(1-methyl-1H-indazol-5-ylmethyl)-1-[4-(1-methyl-piperidin-4-yl)-piperazin-1- yl]-4-[4-(2-oxo-1,2,4,5-tetrahydro-1,3-benzodiazepin-3-yl)-piperidin-1-yl]-butane-1,4-dione,
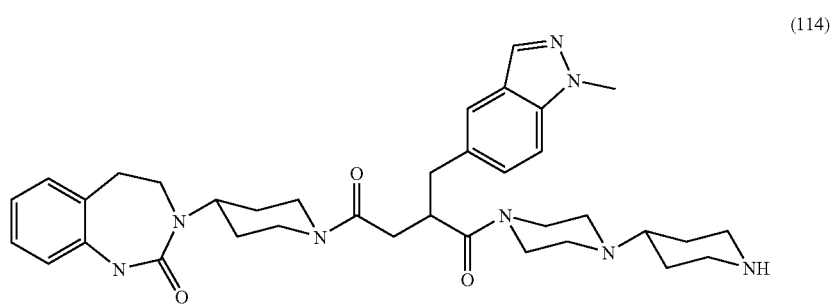
(114)
2-(1-methyl-1H-indazol-5-ylmethyl)-4-[4-(2-oxo-1,2,4,5-tetrahydro-1,3- benzodiazepin-3-yl)-piperidin-1-yl]-1-(4-piperidin-4yl-piperazin-1-yl)-butane-1,4-dione,
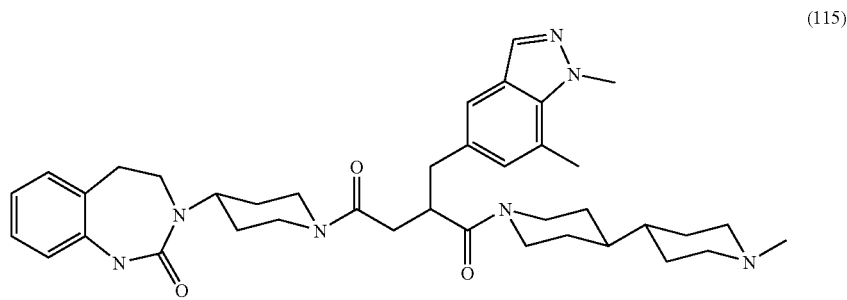
(115)

2-(1,7-dimethyl-1H-indazol-5-ylmethyl)-1-(1'-methyl-4,4'-bipiperidinyl-1-yl)-4- [4-(2-oxo-1,2,4,5-tetrahydro-1,3-benzodiazepin-3-yl)-piperidin-1-yl]-butane-1,4-dione,
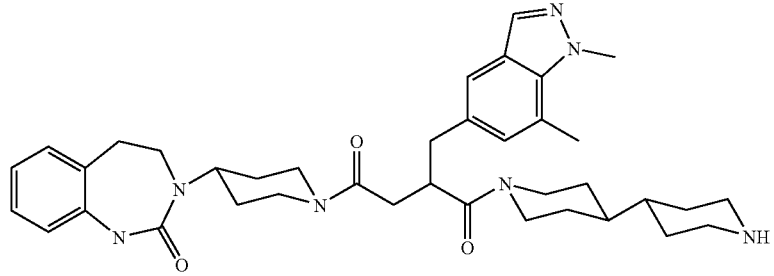
(116)
1-(4,4'-bipiperidinyl-1-yl)-2-(1,7-dimethyl-1H-indazol-5-ylmethyl)-4-[4- (2-oxo-1,2,4,5-tetrahydro-1,3-benzodiazepin-3-yl)-piperidin-1-yl]-butane-1,4-dione,
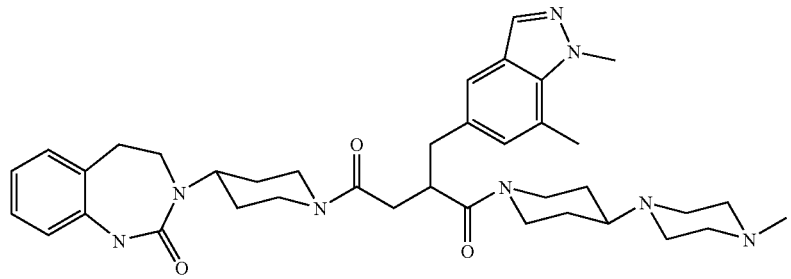
(117)
2-(1,7-dimethyl-1H-indazol-5-ylmethyl)-1-[4-(4-methyl-piperazin-1yl)- piperidin-1-yl]-4[4-(2-oxo-1,2,4,5-tetrahydro-1,3-benzodiazepin-3-yl)-piperidin-1yl]-butane-1,4-dione,
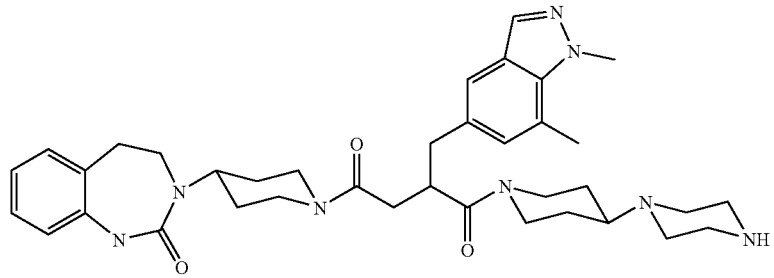
(118)

2-(1,7-dimethyl-1H-indazol-5-ylmethyl)-4-[4-(2-oxo-1,2,4,
5-tetrahydro-1,3- benzodiazepin-3-yl)-piperidin-1-yl]-1-
(4-piperazin-1yl-piperidin-1-yl)-butane-1,4-dione,
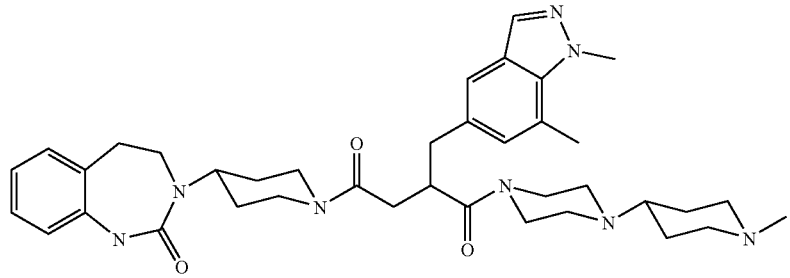
(119)
2-(1,7-dimethyl-1H-indazol-5-ylmethyl)-1-[4-(1-methyl-pi-
peridin-4-yl)- piperazin-1-yl]-4-[4-(2-oxo-1,2,4,5-tet-
rahydro-1,3-benzodiazepin-3-yl)-piperidin-1-yl]-butane-
1,4-dione,
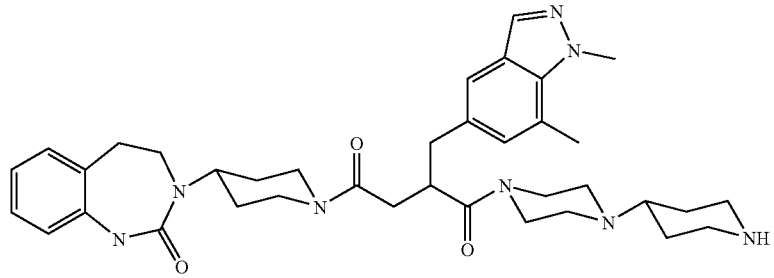
(120)
2-(1,7-dimethyl-1H-indazol-5-ylmethyl)-4-[4-(2-oxo-1,2,4,
5-tetrahydro-1,3- benzodiazepin-3-yl)-piperidin-1-yl]-1-
(4-piperidin-4yl-piperazin-1-yl)-butane-1,4-dione,
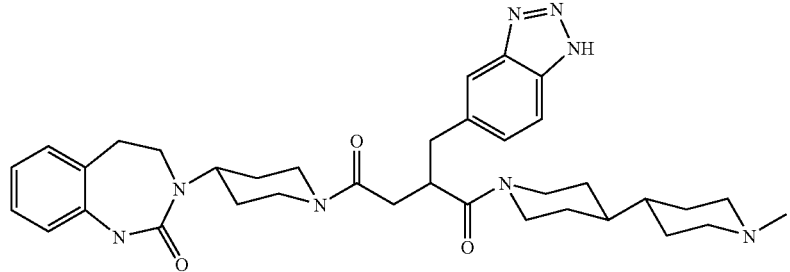
(121)

2-(1H-benzotriazol-5-ylmethyl)-1-(1'-methyl-4,4'-bipip- eridinyl-1-yl)-4-[4-(2- oxo-1,2,4,5-tetrahydro-1,3-benzo- diazepin-3-yl)-piperidin-1-yl]-butane-1,4-dione,
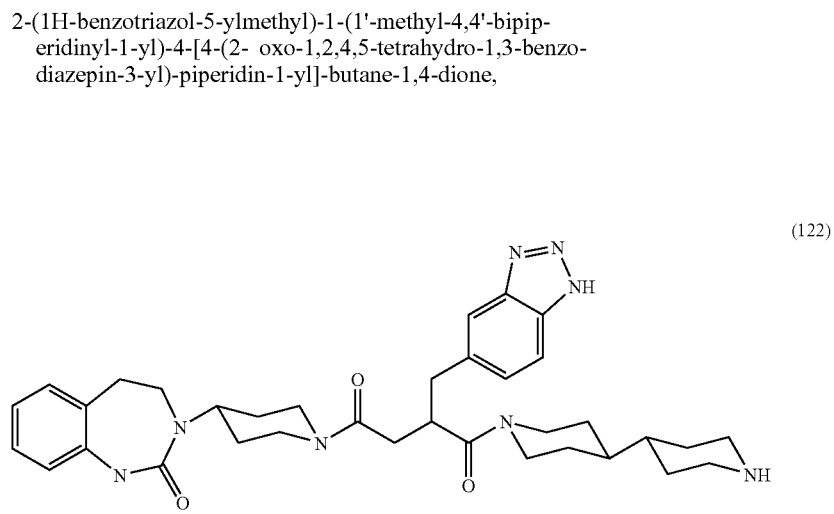
(122)
2-(1H-benzotriazol-5-ylmethyl)-1-(4,4'-bipiperidinyl-1-yl)- 4-[4-(2- oxo-1,2,4,5-tetrahydro-1,3-benzodiazepin-3-yl)- piperidin-1-yl]-butane-1,4-dione,
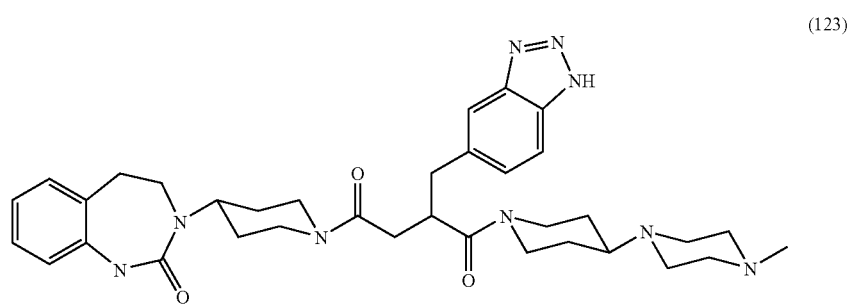
(123)
2-(1H-benzotriazol-5-ylmethyl)-1-[4-(4-methyl-piperazin- 1yl)-piperidin-1-yl]-4- [4-(2-oxo-1,2,4,5-tetrahydro-1,3- benzodiazepin-3-yl)-piperidin-1-yl]-butane-1,4-dione,
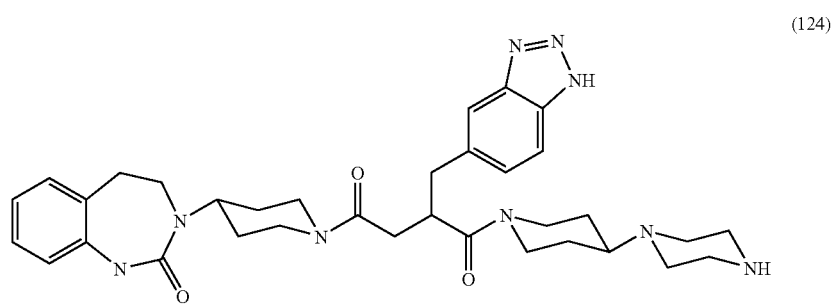
(124)

2-(1H-benzotriazol-5-ylmethyl)-4-[4-(2-oxo-1,2,4,5-tetrahydro-1,3-benzodiazepin-3-yl)-piperidin-1-yl]-1-(4piperazin-1yl-piperidin-1-yl)-butane-1,4-dione,
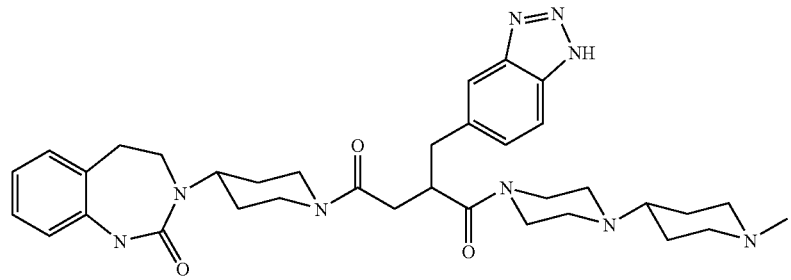
(125)
2-(1H-benzotriazol-5-ylmethyl)-1-[4-(1-methyl-piperidin-4yl)-piperazin-1-yl]-4- [4-(2-oxo-1,2,4,5-tetrahydro-1,3-benzodiazepin-3-yl)-piperidin-1-yl]-butane-1,4-dione,
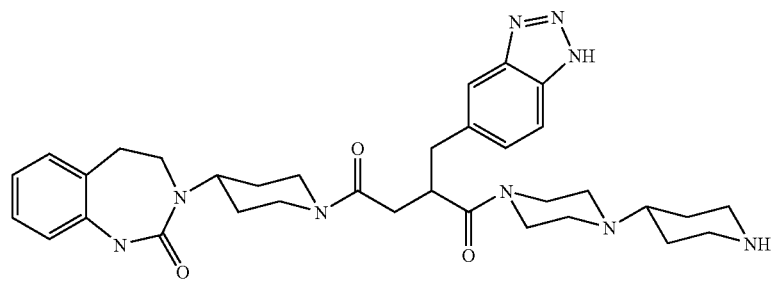
(126)
2-(1H-benzotriazol-5-ylmethyl)-4-[4-(2-oxo-1,2,4,5-tetrahydro-1,3-benzodiazepin-3-yl)-piperidin-1-yl]-1-(4-piperadin-4yl-piperazin-1yl)-butane-1,4-dione,
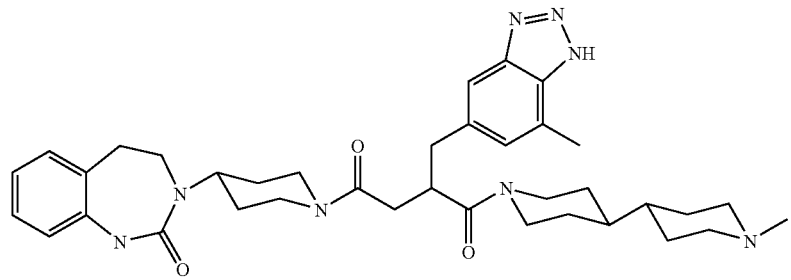
(127)

2-(7-methyl-1H-benzotriazol-5-ylmethyl)-1-(1'-methyl-4,4'-bipiperidinyl-1-yl)-4- [4-(2-oxo-1,2,4,5-tetrahydro-1,3-benzodiazepin-3-yl)-piperidin-1-yl]-butane-1,4-dione,
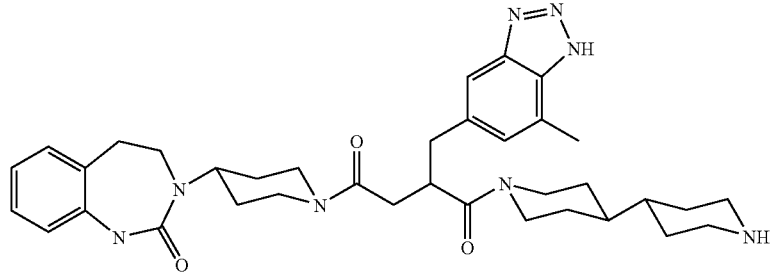
(128)
1-(4,4'-bipiperidinyl-1-yl)-2-(7-methyl-1H-benzotriazol-5-ylmethyl)-4-[4-(2-oxo-1,2,4,5-tetrahydro-1,3-benzodiazepin-3-yl)-piperidin-1-yl]-butane-1,4-dione,
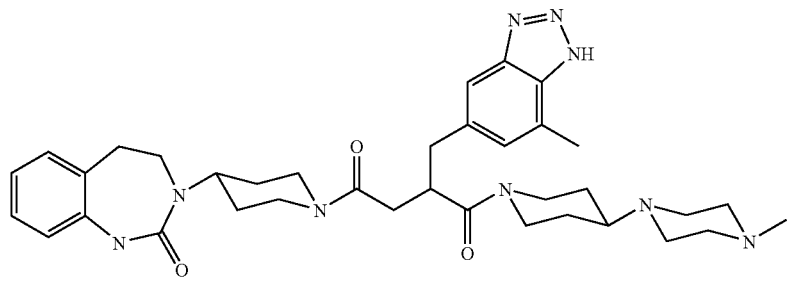
(129)
2-(7-methyl-1H-benzotriazol-5-ylmethyl)-1-[4(4-methyl-piperazin-1-yl)- piperidin-1-yl]-4-[4-(2-oxo-1,2,4,5-tetrahydro-1,3-benzodiazepin-3-yl)-piperidin-1-yl]-butane-1,4-dione,
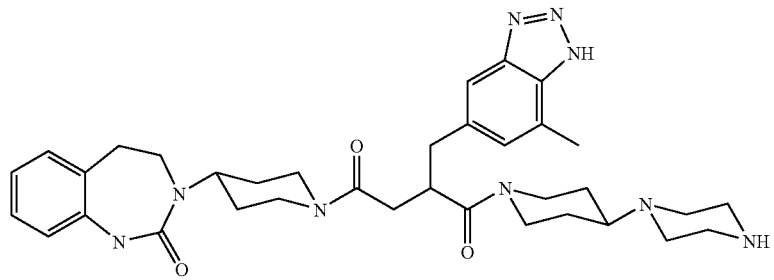
(130)

2-(7-methyl-1H-benzotriazol-5-ylmethyl)-4-[4-(2-oxo-1,2,4,5-tetrahydro-1,3- benzodiazepin-3-yl)-piperidin-1-yl]-1-(4-piperazin-1-yl-piperidin-1yl)-butane-1,4-dione,

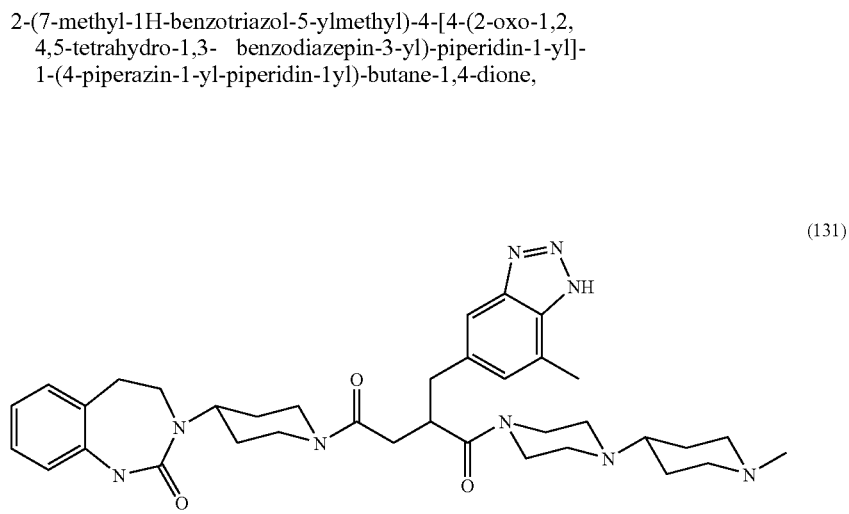

(131)

2-(7-methyl-1H-benzotriazol-5-ylmethyl)-1-[4(1-methyl-piperidin-4-yl)- piperazin-1-yl]-4-[4-(2-oxo-1,2,4,5-tetrahydro-1,3-benzodiazepin-3-yl)-piperidin-1-yl]-butane-1,4-dione,

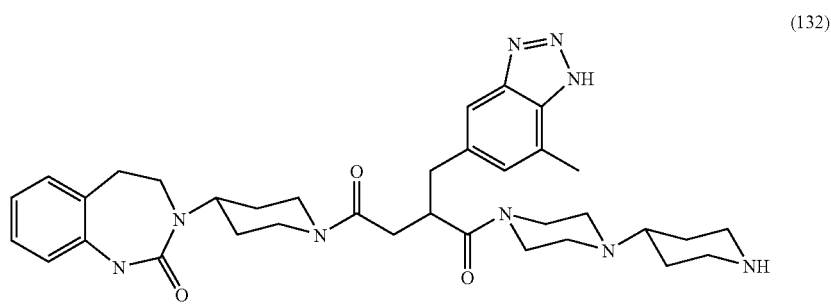

(132)

2-(7-methyl-1H-benzotriazol-5-ylmethyl)-4-[4(2-oxo-1,2,4,5-tetrahydro-1,3- benzodiazepin-3-yl)-piperidin-1-yl]-1-(4-piperadin-4-yl-piperazin-1yl)-butane-1,4-dione,

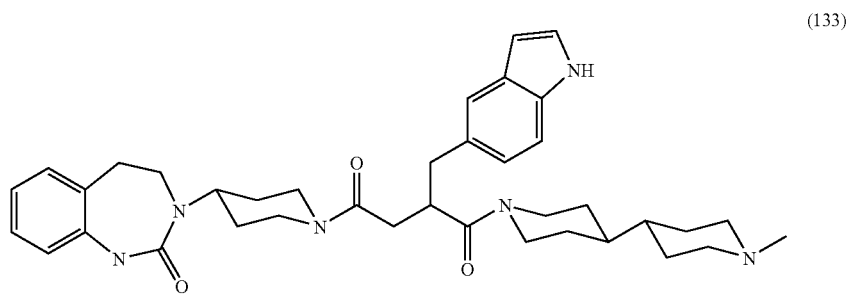

(133)

2-(1H-indol-5-ylmethyl)-1(1'-methyl-4,4'-bipiperidinyl-1yl)-4-[4-(2-oxo- 1,2,4,5-tetrahydro-1,3-benzodiazepin-3-yl)-piperidin-1-yl]-butane-1,4-dione,
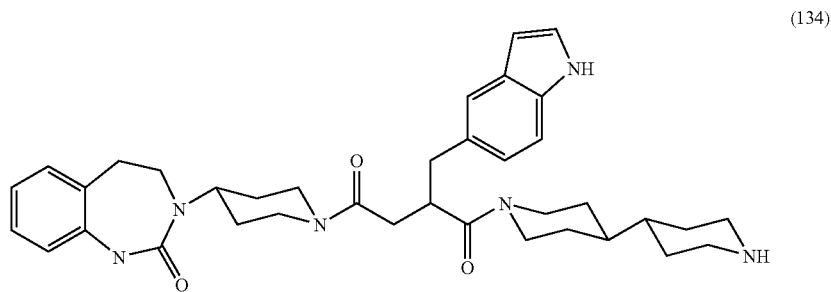
(134)
1-(4,4'-bipiperidinyl-1yl)-2-(1H-indol-5-ylmethyl)-4-[4-(2-oxo-1,2,4,5- tetrahydro-1,3-benzodiazepin-3-yl)-piperidin-1-yl]-butane-1,4-dione,
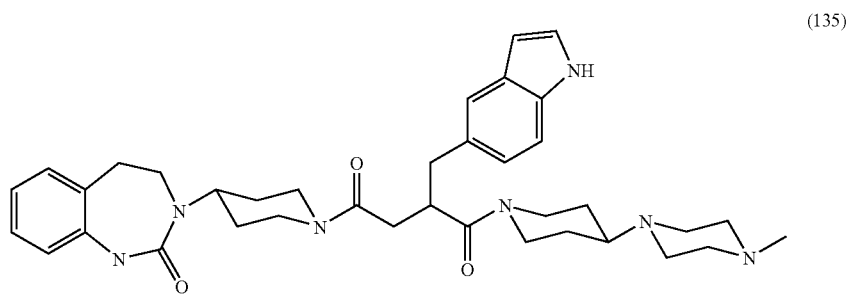
(135)
2-(1H-indol-5-ylmethyl)-1[4-(4-methyl-piperazin-1yl)-piperidin-1-yl]-4-[(2- oxo-1,2,4,5-tetrahydro-1,3-benzodiazepin-3-yl)-piperidin-1-yl]-butane-1,4-dione,
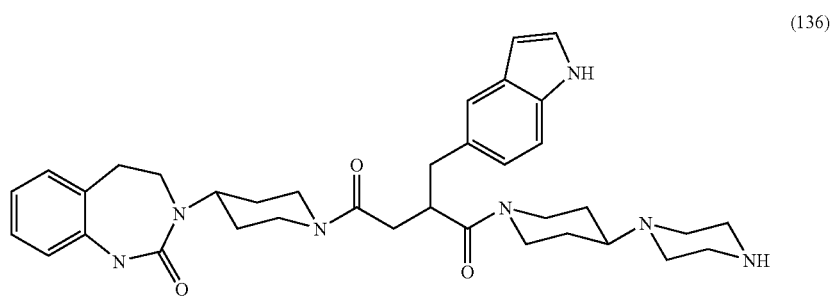
(136)

2-(1H-indol-5-ylmethyl)-4-[4-(2-oxo-1,2,4,5-tetrahydro-1,
3-benzodiazepin-3-    yl)-piperidin-1-yl]-1-(4-piperazin-
1yl-piperidin-1yl)-butane-1,4-dione,
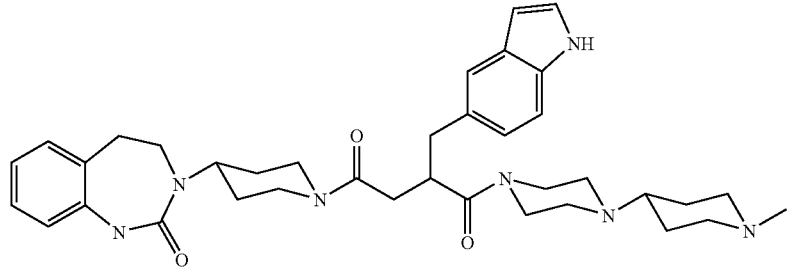
(137)
2-(1H-indol-5-ylmethyl)-1[4-(1-methyl-piperidin-4yl)-pip-
erazin-1yl]-4-[4-(2- oxo-1,2,4,5-tetrahydro-1,3-benzodi-
azepin-3-yl)-piperidin-1-yl]-butane-1,4-dione,
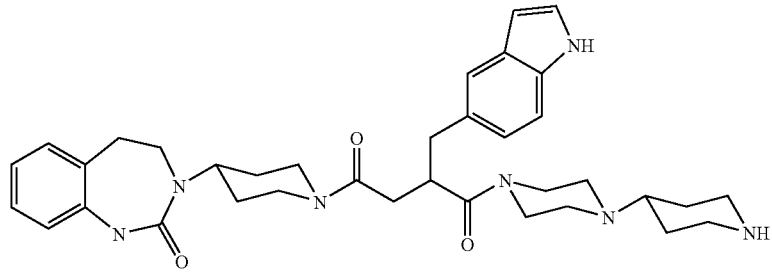
(138)
2-(1H-indol-5-ylmethyl)-4-[4-(2-oxo-1,2,4,5-tetrahydro-1,
3-benzodiazepin-3-    yl)-piperidin-1-yl]1-(4piperidin-4yl-
piperazin-1yl)-butane-1,4-dione,
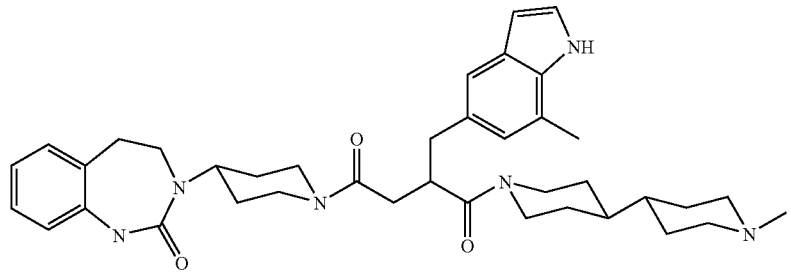
(139)

1-(1'-methyl-4,4'-bipiperidinyl-1yl)-2-(7-methyl-1H-indol-5-ylmethyl)-4-[4-(2- oxo-1,2,4,5-tetrahydro-1,3-benzodiazepin-3-yl)-piperidin-1-yl]-butane-1,4-dione,
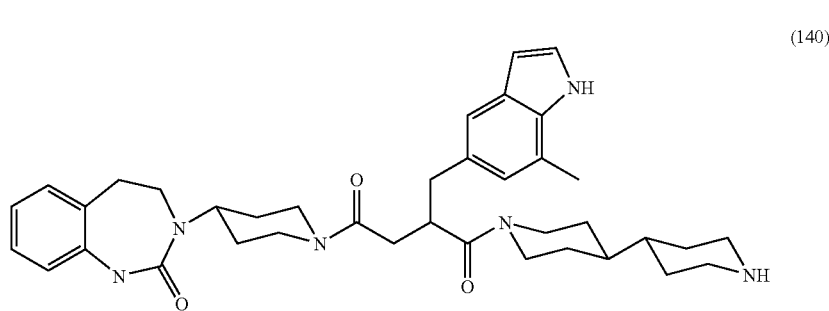
(140)
1-(4,4'-bipiperidinyl-1yl)-2-(7-methyl-1H-indol-5-ylmethyl)-4-[4-(2-oxo-1,2,4,5- tetrahydro-1,3-benzodiazepin-3-yl)-piperidin-1-yl]-butane-1,4-dione,
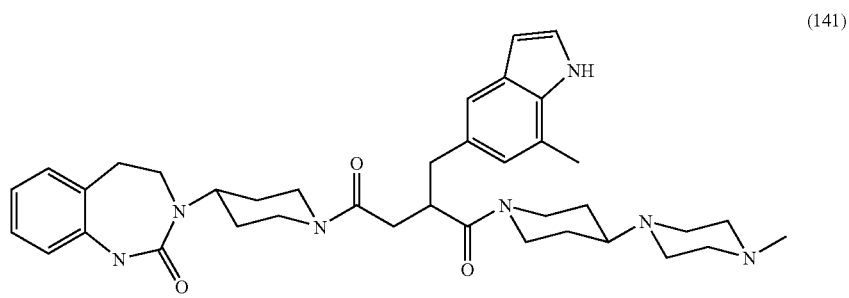
(141)
2-(7-methyl-1H-indol-5-ylmethyl)-1-[4-(4methyl-piperazin-1-yl)-piperidin-1-yl]- 4-[4-(2-oxo-1,2,4,5-tetrahydro-1,3-benzodiazepin-3-yl)-piperidin-1-yl]-butane-1,4-dione,
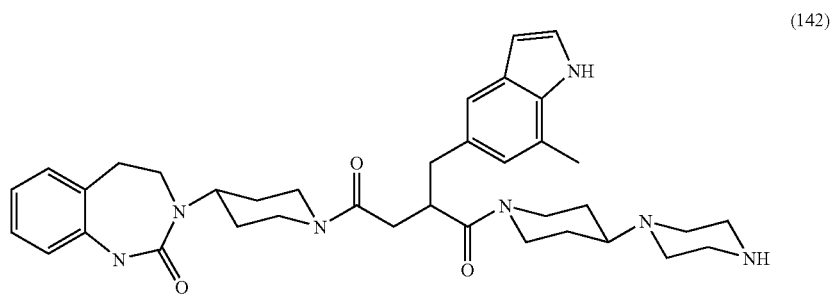
(142)

2-(7-methyl-1H-indol-5-ylmethyl)-4-[4-(2-oxo-1,2,4,5-tetrahydro-1,3- benzodiazepin-3-yl)-piperidin-1-yl]-1-(4-piperazin-1-yl-piperadin-1-yl)-butane-1,4-dione,
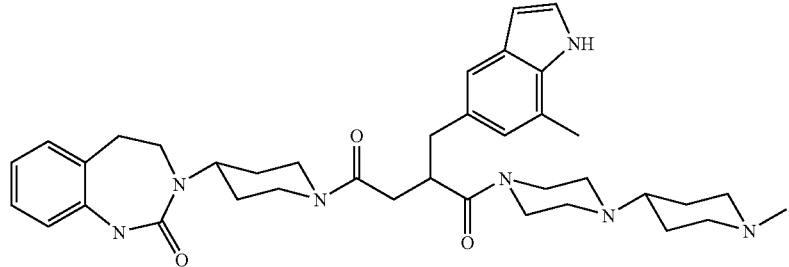
(143)
2-(7-methyl-1H-indol-5-ylmethyl)-1-[4-(1methyl-piperidin-4-yl)-piperazin-1-yl]- 4-[4-(2-oxo-1,2,4,5-tetrahydro-1,3-benzodiazepin-3-yl)-piperidin-1-yl]-butane-1,4-dione,
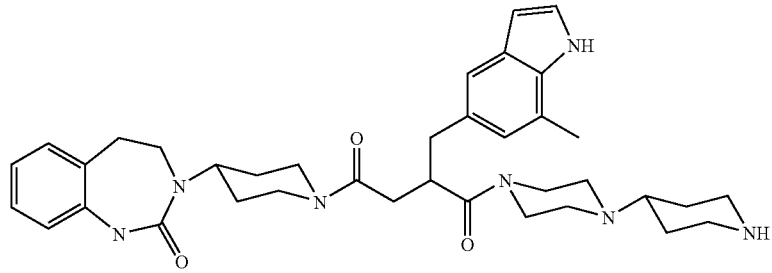
(144)
2-(7-methyl-1H-indol-5-ylmethyl)-4-[4-(2-oxo-1,2,4,5-tetrahydro-1,3- benzodiazepin-3-yl)-piperidin-1-yl]-1-(4-piperidin-4yl-piperazin-1yl)-butane-1,4-dione,
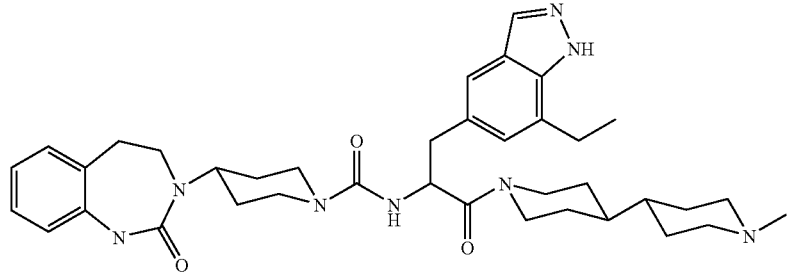
(145)

4-(2-oxo-1,2,4,5-tetrahydro-1,3-benzodiazepin-3-yl)-piperi-
dine-1-carboxylic acid [1-(7ethyl-1H-indazol-5-ylm-
ethyl)-2-(1'-methyl-4,4'-bipiperdinyl-1-yl)-2-oxo-ethyl]-
amide,

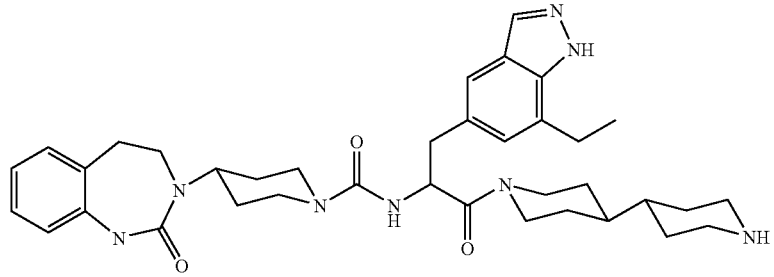

(146)

4-(2-oxo-1,2,4,5-tetrahydro-1,3-benzodiazepin-3-yl)-piperi-
dine-1-carboxylic acid [2-(4,4'-bipiperidinyl-1-yl)-1-
(7ethyl-1H-indazol-5-ylmethyl)-2-oxo-ethyl]-amide,

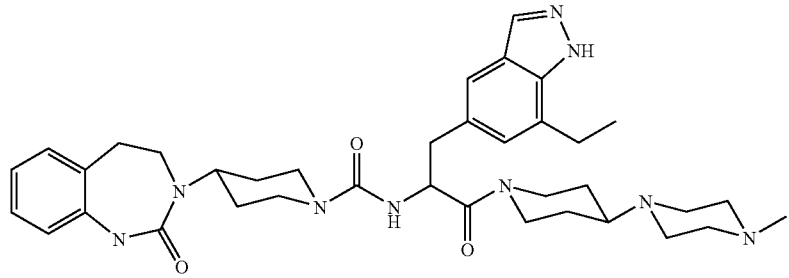

(147)

4-(2-oxo-1,2,4,5-tetrahydro-1,3-benzodiazepin-3-yl)-piperi-
dine-1-carboxylic acid {1-(7ethyl-1H-indazol-5-ylm-
ethyl)-2-[4-(4-methyl-piperazin-1yl)-piperidin-1-yl]-2-
oxo-ethyl}-amide,

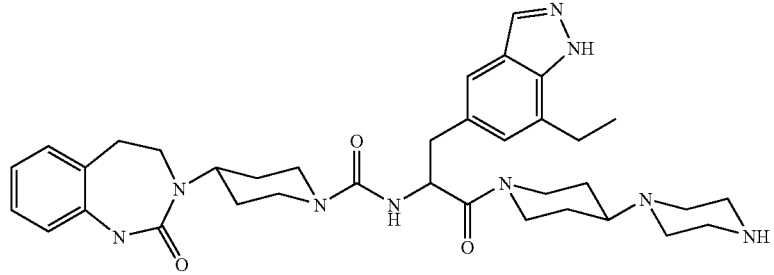

(148)

4-(2-oxo-1,2,4,5-tetrahydro-1,3-benzodiazepin-3-yl)-piperidine-1-carboxylic acid [1-(7ethyl-1H-indazol-5-ylmethyl)-2-oxo-2-(4-piperazin-1yl-piperidin-1-yl)-ethyl]-amide,

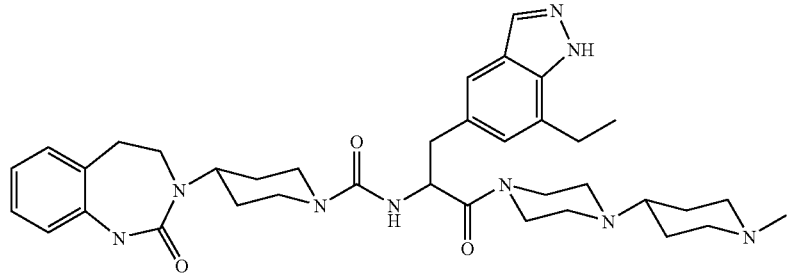

(149)

4-(2-oxo-1,2,4,5-tetrahydro-1,3-benzodiazepin-3-yl)-piperidine-1-carboxylic acid {1-(7ethyl-1H-indazol-5-ylmethyl)-2-[4-(1methyl-piperidin-4-yl)-piperazin-1-yl]-2-oxo-ethyl}-amide,

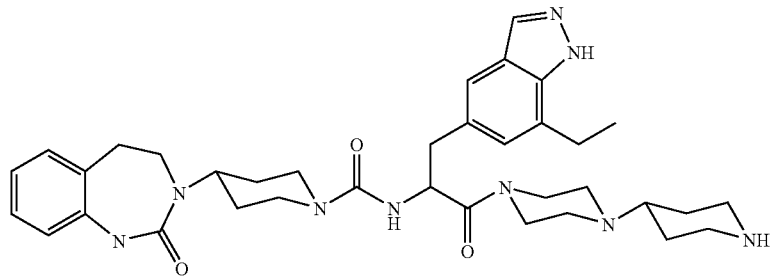

(150)

4-(2-oxo-1,2,4,5-tetrahydro-1,3-benzodiazepin-3-yl)-piperidine-1-carboxylic acid [1-(7ethyl-1H-indazol-5-ylmethyl)-2-oxo-2-(4-piperidin-4-yl-piperazin-1-yl)-ethyl]-amide,

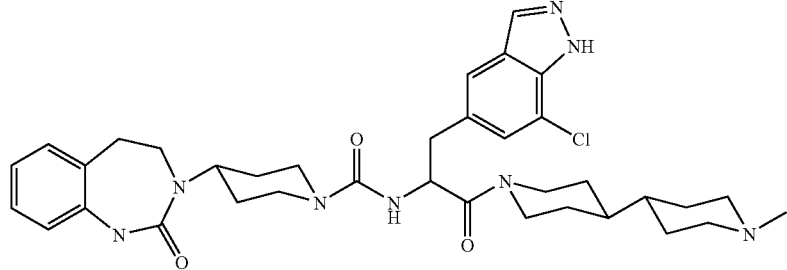

(151)

4-(2-oxo-1,2,4,5-tetrahydro-1,3-benzodiazepin-3-yl)-piperidine-1-carboxylic acid [1-(7-chloro-1H-indazol-5-ylmethyl)-2-(1'-methyl-4,4'-bipiperidinyl-1-yl)-2-oxo-ethyl]-amide,

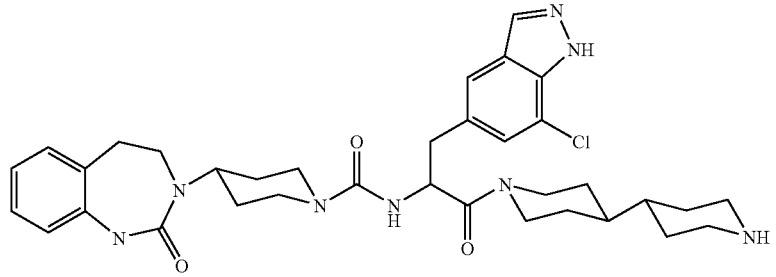

(152)

4-(2-oxo-1,2,4,5-tetrahydro-1,3-benzodiazepin-3-yl)-piperidine-1-carboxylic acid [2-(4,4'-bipiperidinyl-1-yl)-1-(7-chloro-1H-indazol-5-ylmethyl)-2-oxo-ethyl]-amide,

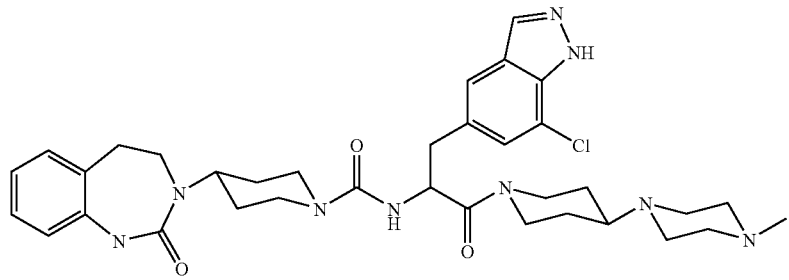

(153)

4-(2-oxo-1,2,4,5-tetrahydro-1,3-benzodiazepin-3-yl)-piperidine-1-carboxylic acid {1-(7-chloro-1H-indazol-5-ylmethyl)-2-[4-(4-methyl-piperazin-1-yl)-piperidin-1-yl]-2-oxo-ethyl}-amide,

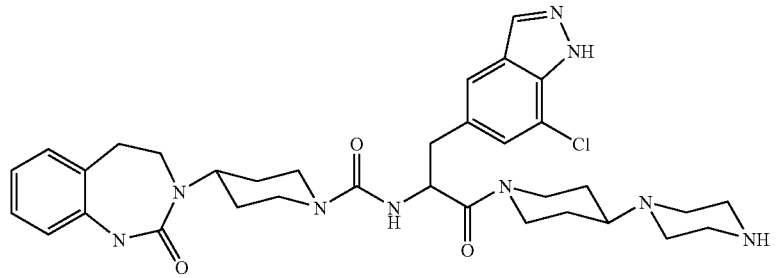

(154)

4-(2-oxo-1,2,4,5-tetrahydro-1,3-benzodiazepin-3-yl)-piperidine-1-carboxylic acid [1-(7-chloro-1H-indazol-5-ylmethyl)-2-oxo-2-(4-piperazin-1-yl-piperidin-1-yl)-ethyl]-amide,

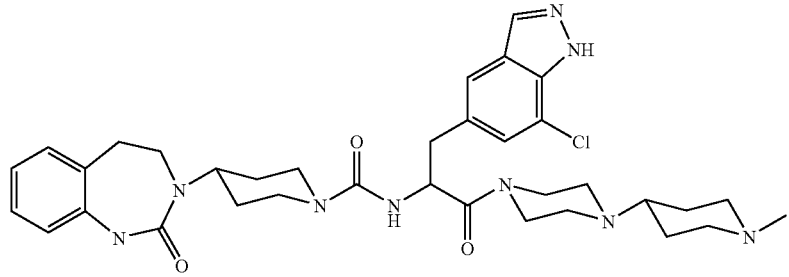

(155)

4-(2-oxo-1,2,4,5-tetrahydro-1,3-benzodiazepin-3-yl)-piperidine-1-carboxylic acid {1-(7-chloro-1H-indazol-5-ylmethyl)-2-[4-(1-methyl-piperidin-4-yl)-piperazin-1-yl]-2-oxo-ethyl}-amide,

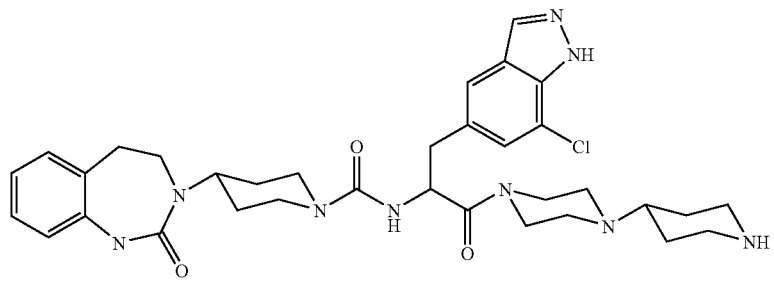

(156)

4-(2-oxo-1,2,4,5-tetrahydro-1,3-benzodiazepin-3-yl)-piperidine-1-carboxylic acid [1-(7-chloro-1H-indazol-5-ylmethyl)-2-oxo-2-(4-piperidin-4-yl-piperazin-1-yl)-ethyl]-amide,

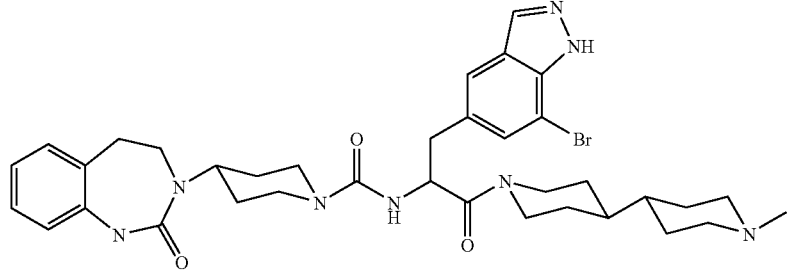

(157)

4-(2-oxo-1,2,4,5-tetrahydro-1,3-benzodiazepin-3-yl)-piperidine-1-carboxylic acid [1-(7-bromo-1H-indazol-5-ylmethyl)-2-(1'-methyl-4,4'-bipiperidinyl-1-yl)-2-oxo-ethyl]-amide,

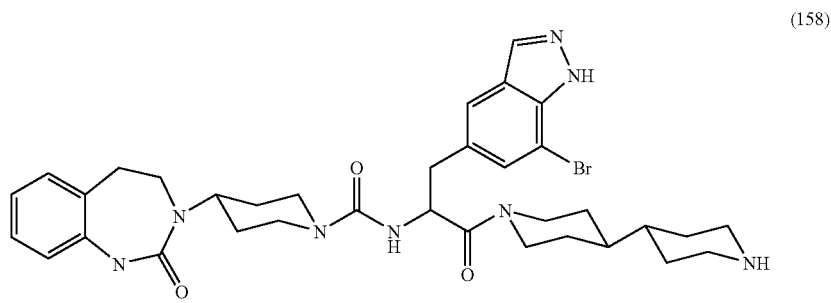

(158)

4-(2-oxo-1,2,4,5-tetrahydro-1,3-benzodiazepin-3-yl)-piperidine-1-carboxylic acid [2-(4,4'-bipiperidinyl-1-yl)-1-(7-bromo-1H-indazol-5-ylmethyl)-2-oxo-ethyl]-amide,

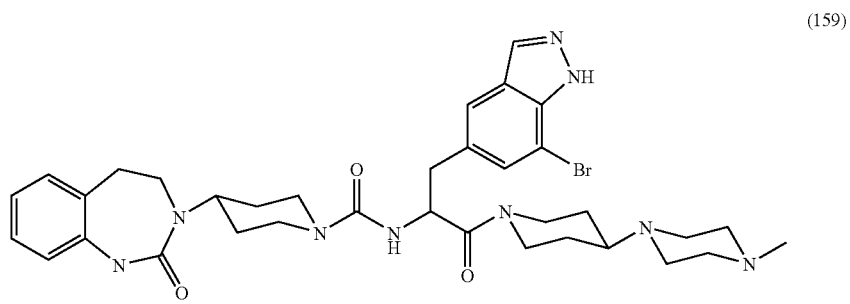

(159)

4-(2-oxo-1,2,4,5-tetrahydro-1,3-benzodiazepin-3-yl)-piperidine-1-carboxylic acid {1-(7-bromo-1H-indazol-5-ylmethyl)-2-[4-(4-methyl-piperazin-1-yl)-piperidin-1-yl]-2-oxo-ethyl}-amide,

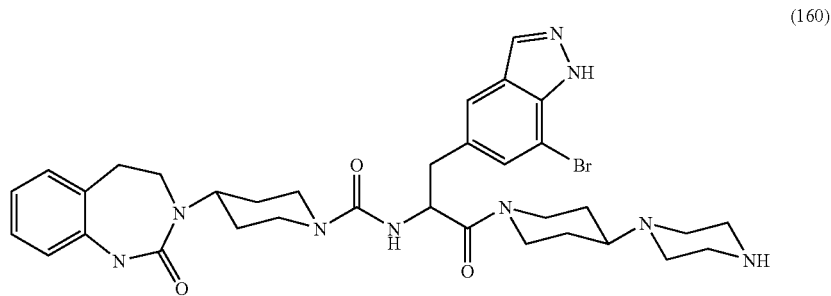

(160)

4-(2-oxo-1,2,4,5-tetrahydro-1,3-benzodiazepin-3-yl)-piperidine-1-carboxylic acid [1-(7-bromo-1H-indazol-5-ylmethyl)-2-oxo-2-(4-piperazin-1-yl-piperidin-1-yl)-ethyl]-amide,

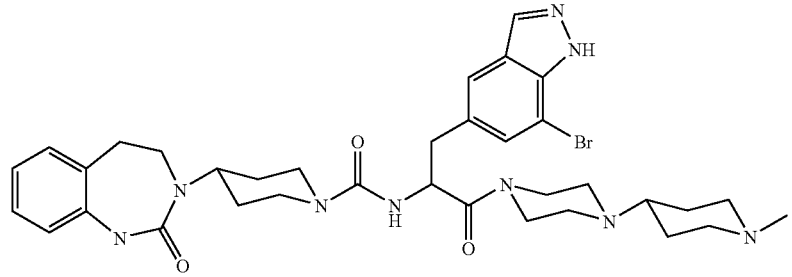

(161)

4-(2-oxo-1,2,4,5-tetrahydro-1,3-benzodiazepin-3-yl)-piperidine-1-carboxylic acid {1-(7-bromo-1H-indazol-5-ylmethyl)-2-[4-(1-methyl-piperidin-4-yl)-piperazin-1-yl]-2-oxo-ethyl}-amide,

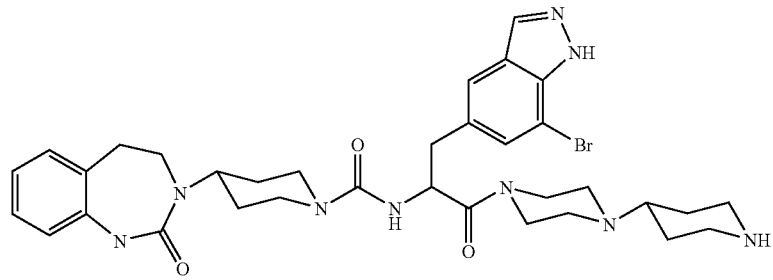

(162)

4-(2-oxo-1,2,4,5-tetrahydro-1,3-benzodiazepin-3-yl)-piperidine-1-carboxylic acid [1-(7-bromo-1H-indazol-5-ylmethyl)-2-oxo-2-(4-piperidin-4-yl-piperazin-1-yl)-ethyl]-amide,

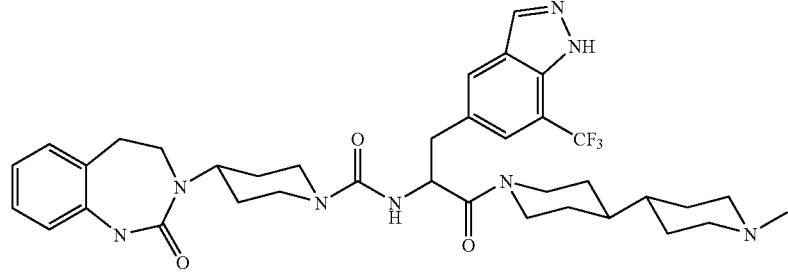

(163)

4-(2-oxo-1,2,4,5-tetrahydro-1,3-benzodiazepin-3-yl)-piperidine-1-carboxylic acid [2-(1'-methyl-4,4'-bipiperidinyl-1-yl)-2-oxo-1-(7-trifluoromethyl-1H-indazol-5-ylmethyl)-ethyl]-amide,

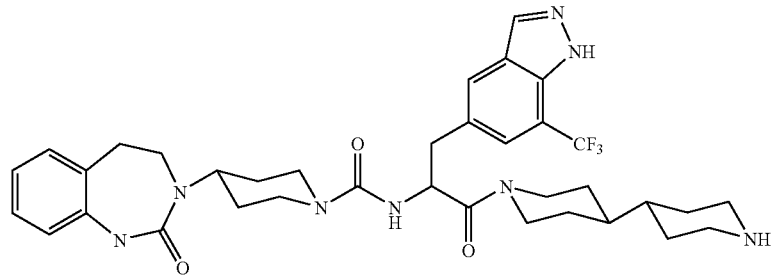

(164)

4-(2-oxo-1,2,4,5-tetrahydro-1,3-benzodiazepin-3-yl)-piperidine-1-carboxylic acid [2-(4,4'-bipiperidinyl-1-yl)-2-oxo-1-(7-trifluoromethyl-1H-indazol-5-ylmethyl)-ethyl]-amide,

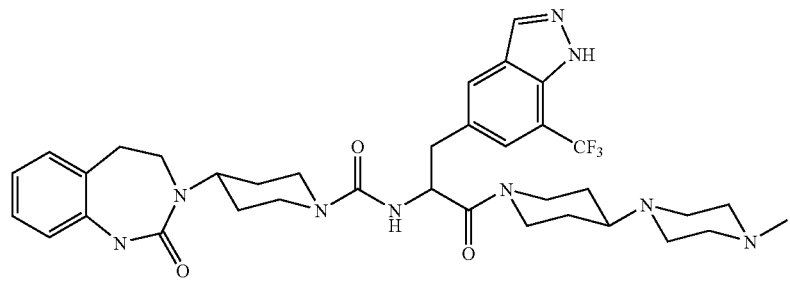

(165)

4-(2-oxo-1,2,4,5-tetrahydro-1,3-benzodiazepin-3-yl)-piperidine-1-carboxylic acid [2-[4-(4-methyl-piperazin-1-yl)-piperidin-1-yl]-2-oxo-1-(7-trifluoromethyl-1H-indazol-5-ylmethyl)-ethyl]-amide,

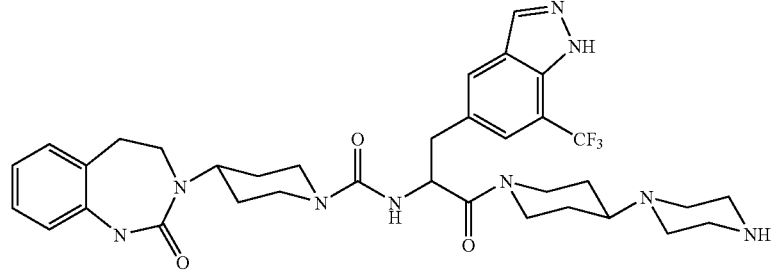

(166)

4-(2-oxo-1,2,4,5-tetrahydro-1,3-benzodiazepin-3-yl)-piperidine-1-carboxylic acid [2-oxo-2-(4-piperazin-1-yl-piperidin-1-yl)-1-(7-trifluoromethyl-1H-indazol-5-ylmethyl)-ethyl]-amide,

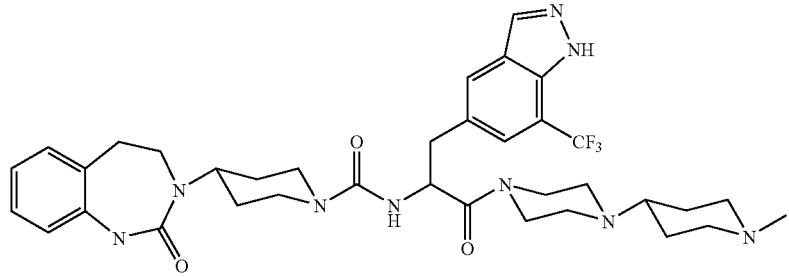

(167)

4-(2-oxo-1,2,4,5-tetrahydro-1,3-benzodiazepin-3-yl)-piperidine-1-carboxylic acid [2-[4-(1-methyl-piperidin-4-yl)-piperazin-1-yl]-2-oxo-1-(7-trifluoromethyl-1H-indazol-5-ylmethyl)-ethyl]-amide,

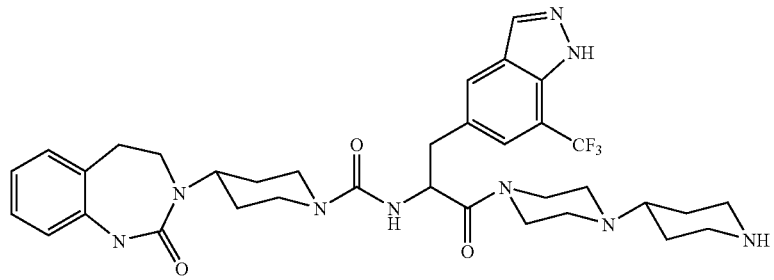

(168)

4-(2-oxo-1,2,4,5-tetrahydro-1,3-benzodiazepin-3-yl)-piperidine-1-carboxylic acid [2-oxo-2-(4-piperidin-4-yl-piperazin-1-yl)-1-(7-trifluoromethyl-1H-indazol-5-ylmethyl)-ethyl]-amide,

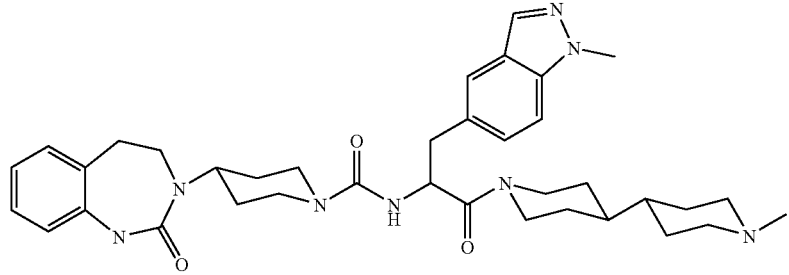

(169)

4-(2-oxo-1,2,4,5-tetrahydro-1,3-benzodiazepin-3-yl)-piperidine-1-carboxylic acid [2-(1'-methyl-4,4'-bipiperidinyl-1-yl)-1-(1-methyl-1H-indazol-5-ylmethyl)-2-oxo-ethyl]-amide,

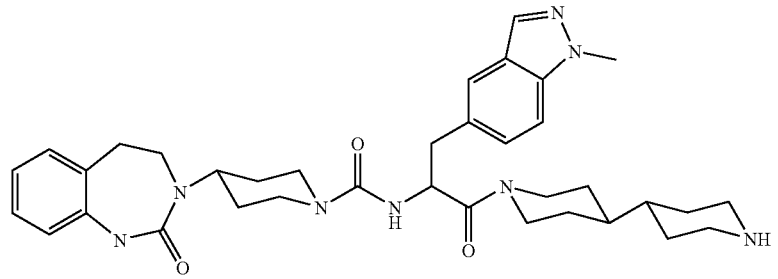

(170)

4-(2-oxo-1,2,4,5-tetrahydro-1,3-benzodiazepin-3-yl)-piperidine-1-carboxylic acid [2-(4,4'-bipiperidinyl-1-yl)-1-(1-methyl-1H-indazol-5-ylmethyl)-2-oxo-ethyl]-amide,

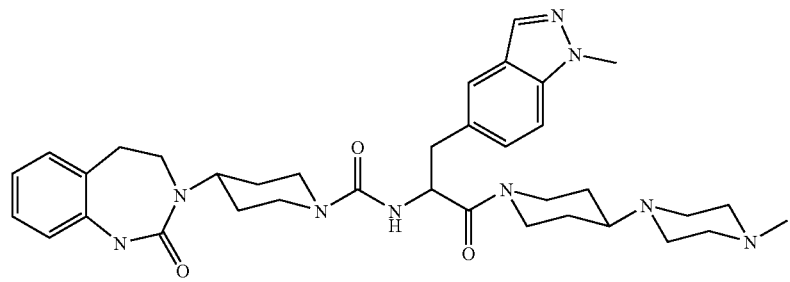

(171)

4-(2-oxo-1,2,4,5-tetrahydro-1,3-benzodiazepin-3-yl)-piperidine-1-carboxylic acid {1-(1-methyl-1H-indazol-5-ylmethyl)-2-[4-(4-methyl-piperazin-1-yl)-piperidin-1-yl]-2-oxo-ethyl}-amide,

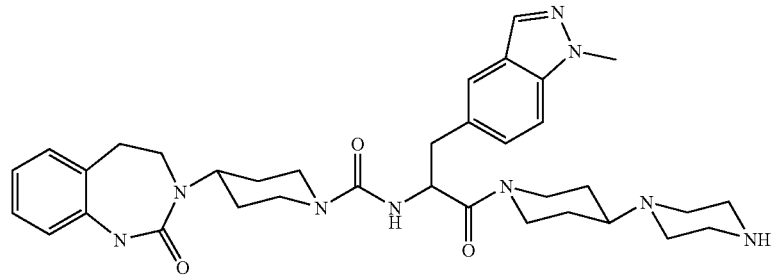

(172)

4-(2-oxo-1,2,4,5-tetrahydro-1,3-benzodiazepin-3-yl)-piperidine-1-carboxylic acid [1-(1-methyl-1H-indazol-5-ylmethyl)-2-oxo-2-(4-piperazin-1-yl-piperidin-1-yl)-ethyl]-amide,

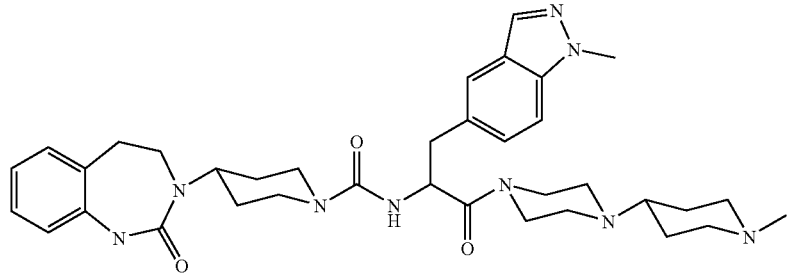

(173)

4-(2-oxo-1,2,4,5-tetrahydro-1,3-benzodiazepin-3-yl)-piperidine-1-carboxylic acid {1-(1-methyl-1H-indazol-5-ylmethyl)-2-[4-(1-methyl-piperidin-4-yl)-piperazin-1-yl]-2-oxo-ethyl}-amide,

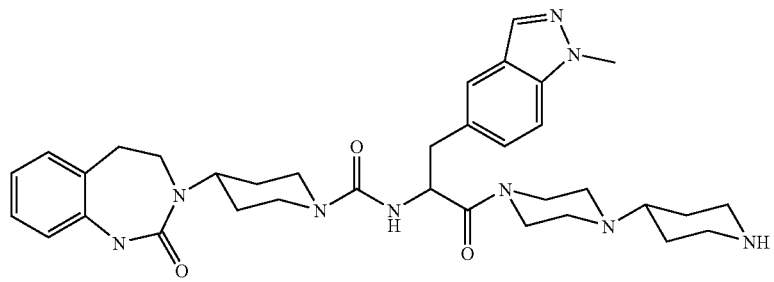

(174)

4-(2-oxo-1,2,4,5-tetrahydro-1,3-benzodiazepin-3-yl)-piperidine-1-carboxylic acid [1-(1-methyl-1H-indazol-5-ylmethyl)-2-oxo-2-(4-piperidin-4-yl-piperazin-1-yl)-ethyl]-amide,

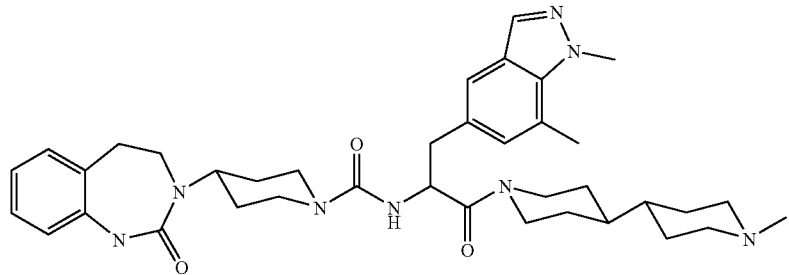

(175)

4-(2-oxo-1,2,4,5-tetrahydro-1,3-benzodiazepin-3-yl)-piperidine-1-carboxylic acid [1-(1,7-dimethyl-1H-indazol-5-yl-methyl)-2-(1'-methyl-4,4'-bipiperidinyl-1-yl)-2-oxo-ethyl]-amide,

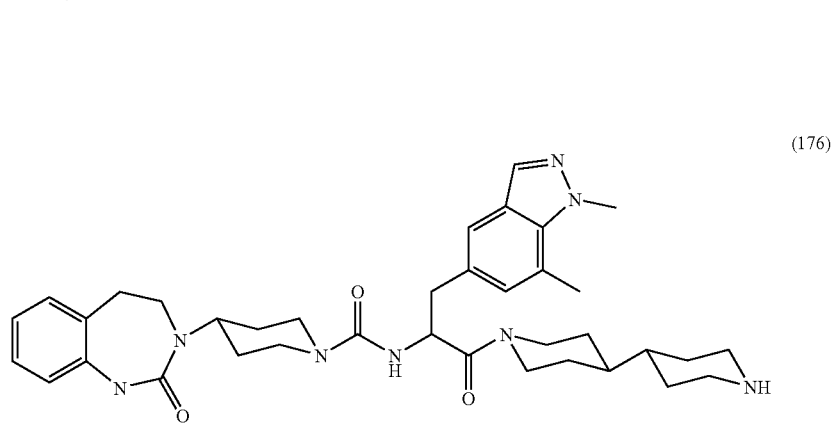
(176)

4-(2-oxo-1,2,4,5-tetrahydro-1,3-benzodiazepin-3-yl)-piperidine-1-carboxylic acid [2-(4,4'-bipiperidinyl-1-yl)-1-(1,7-dimethyl-1H-indazol-5-ylmethyl)-2-oxo-ethyl]-amide,

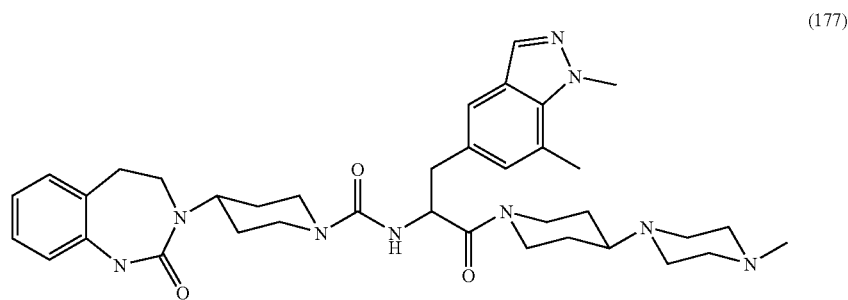
(177)

4-(2-oxo-1,2,4,5-tetrahydro-1,3-benzodiazepin-3-yl)-piperidine-1-carboxylic acid {1-(1,7-dimethyl-1H-indazol-5-ylmethyl)-2-[4-(4-methyl-piperazin-1-yl)-piperidin-1-yl]-2-oxo-ethyl}-amide,

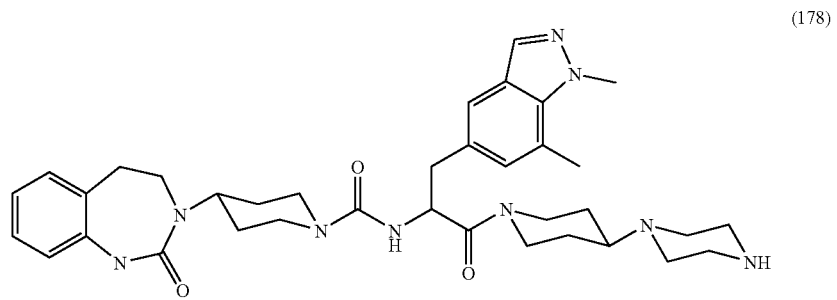
(178)

4-(2-oxo-1,2,4,5-tetrahydro-1,3-benzodiazepin-3-yl)-piperidine-1-carboxylic acid [1-(1,7-dimethyl-1H-indazol-5-ylmethyl)-2-oxo-2-(4-piperazin-1-yl-piperidin-1-yl)-ethyl]-amide,

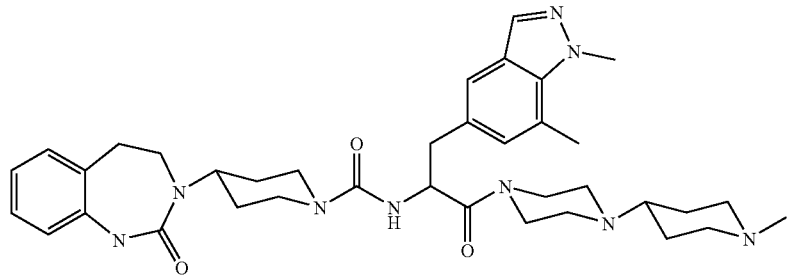

(179)

4-(2-oxo-1,2,4,5-tetrahydro-1,3-benzodiazepin-3-yl)-piperidine-1-carboxylic acid {1-(1,7-dimethyl-1H-indazol-5-ylmethyl)-2-[4-(1-methyl-piperidin-4-yl)-piperazin-1-yl]-2-oxo-ethyl}-amide,

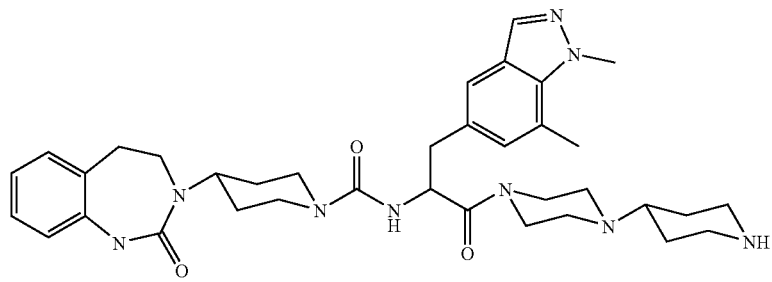

(180)

4-(2-oxo-1,2,4,5-tetrahydro-1,3-benzodiazepin-3-yl)-piperidine-1-carboxylic acid [1-(1,7-dimethyl-1H-indazol-5-ylmethyl)-2-oxo-2-(4-piperidin-4-yl-piperazin-1-yl)-ethyl]-amide,

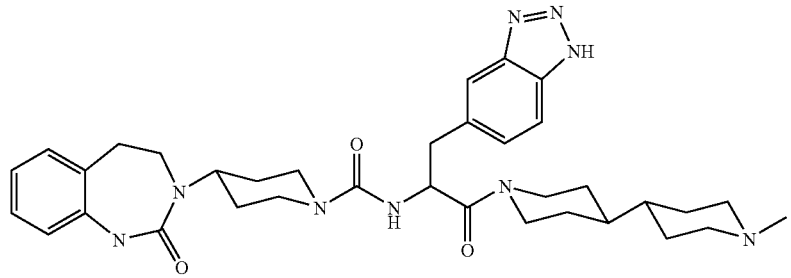

(181)

4-(2-oxo-1,2,4,5-tetrahydro-1,3-benzodiazepin-3-yl)-piperi-
dine-1-carboxylic acid [1-(1H-benzotriazol-5-ylmethyl)-
2-(1'-methyl-4,4'-bipiperidinyl-1-yl)-2-oxo-ethyl]-amide,

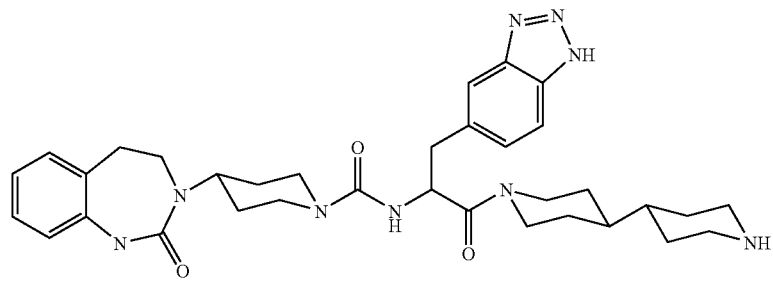

(182)

4-(2-oxo-1,2,4,5-tetrahydro-1,3-benzodiazepin-3-yl)-piperi-
dine-1-carboxylic acid [1-(1H-benzotriazol-5-ylmethyl)-
2-(4,4'-bipiperidinyl-1-yl)-2-oxo-ethyl]-amide,

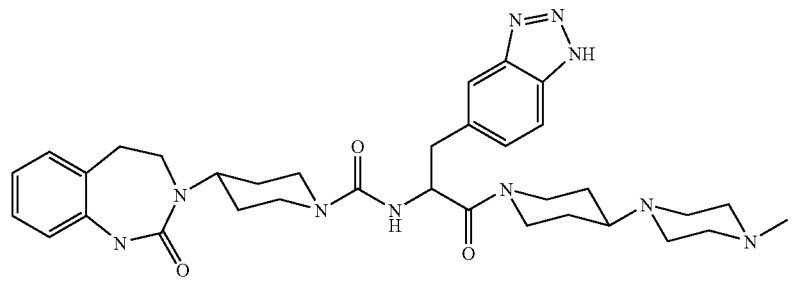

(183)

4-(2-oxo-1,2,4,5-tetrahydro-1,3-benzodiazepin-3-yl)-piperi-
dine-1-carboxylic acid {1-(1H-benzotriazol-5-ylmethyl)-
2-[4-(4-methyl-piperazin-1-yl)-piperidin-1-yl]-2-oxo-
ethyl}-amide,

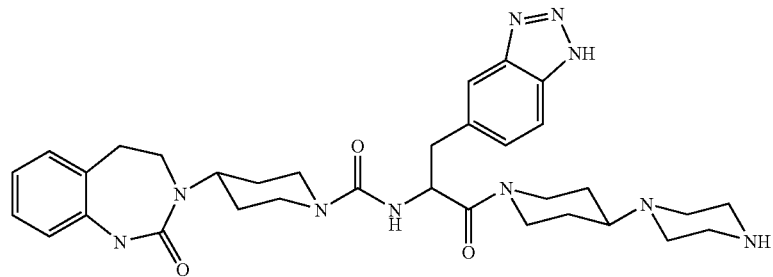

(184)

4-(2-oxo-1,2,4,5-tetrahydro-1,3-benzodiazepin-3-yl)-piperi-
dine-1-carboxylic acid [1-(1H-benzotriazol-5-ylmethyl)-
2-oxo-2-(4-piperazin-1-yl-piperidin-1-yl)-ethyl]-amide,

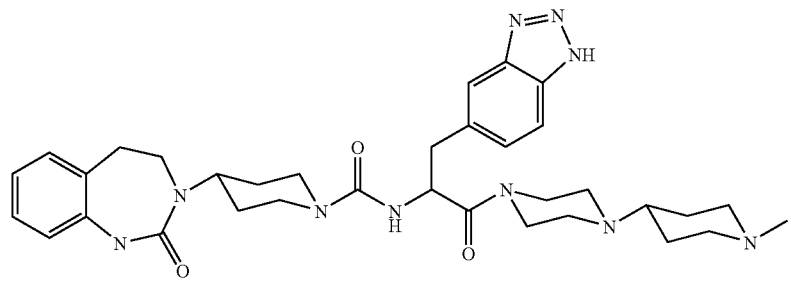

(185)

4-(2-oxo-1,2,4,5-tetrahydro-1,3-benzodiazepin-3-yl)-piperi-
dine-1-carboxylic acid {1-(1H-benzotriazol-5-ylmethyl)-
2-[4-(1-methyl-piperidin-4-yl)-piperazin-1-yl]-2-oxo-
ethyl}-amide,

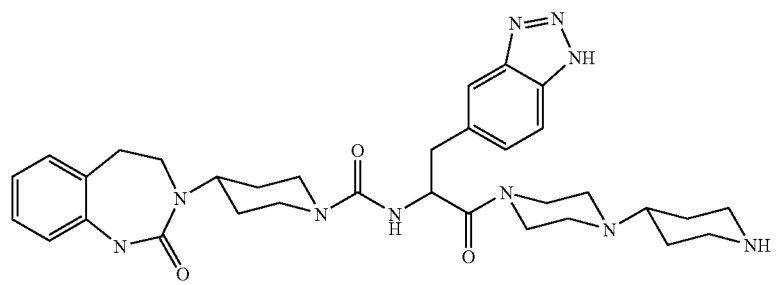

(186)

4-(2-oxo-1,2,4,5-tetrahydro-1,3-benzodiazepin-3-yl)-piperi-
dine-1-carboxylic acid [1-(1H-benzotriazol-5-ylmethyl)-
2-oxo-2-(4-piperidin-4-yl-piperazin-1-yl)-ethyl]-amide,

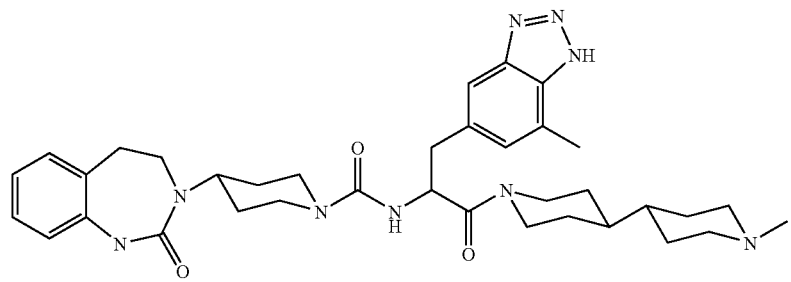

(187)

4-(2-oxo-1,2,4,5-tetrahydro-1,3-benzodiazepin-3-yl)-piperidine-1-carboxylic acid [1-(7-methyl-1H-benzotriazol-5-ylmethyl)-2-(1'-methyl-4,4'-bipiperidinyl-1-yl)-2-oxo-ethyl]-amide,

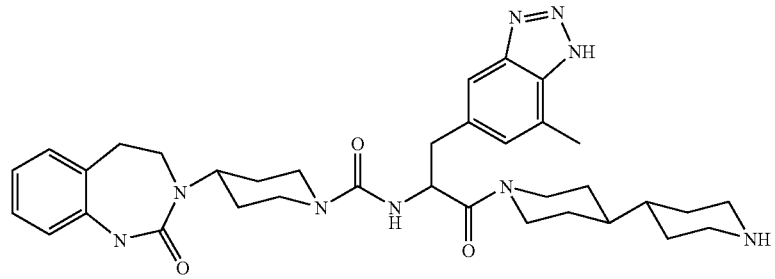

(188)

4-(2-oxo-1,2,4,5-tetrahydro-1,3-benzodiazepin-3-yl)-piperidine-1-carboxylic acid [2-(4,4'-bipiperidinyl-1-yl)-1-(7-methyl-1H-benzotriazol-5-ylmethyl)-2-oxo-ethyl]-amide,

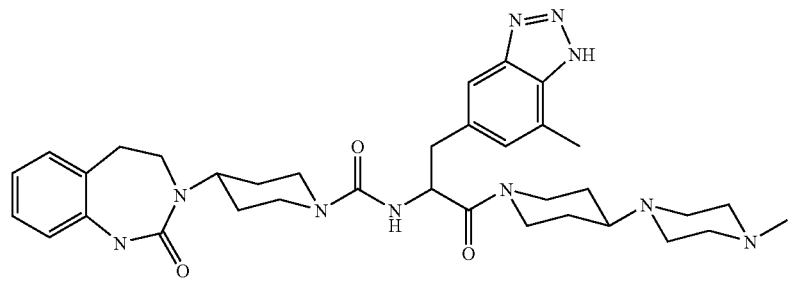

(189)

4-(2-oxo-1,2,4,5-tetrahydro-1,3-benzodiazepin-3-yl)-piperidine-1-carboxylic acid {1-(7-methyl-1H-benzotriazol-5-ylmethyl)-2-[4-(4-methyl-piperazin-1-yl)-piperidin-1-yl]-2-oxo-ethyl}-amide,

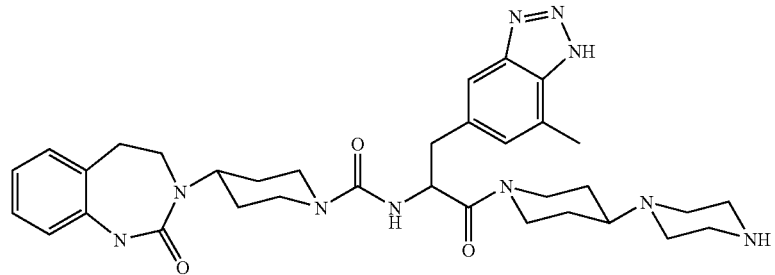

(190)

4-(2-oxo-1,2,4,5-tetrahydro-1,3-benzodiazepin-3-yl)-piperidine-1-carboxylic acid [1-(7-methyl-1H-benzotriazol-5-ylmethyl)-2-oxo-2-(4-piperazin-1-yl-piperidin-1-yl)-ethyl]-amide,

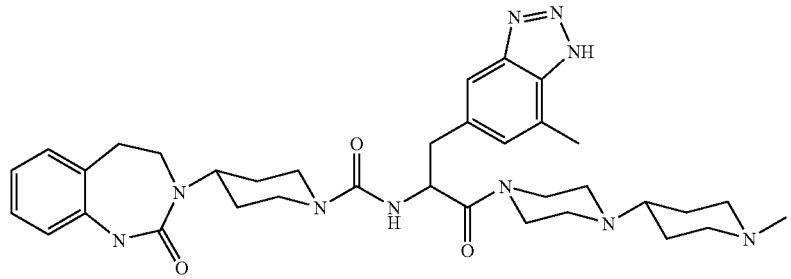

(191)

4-(2-oxo-1,2,4,5-tetrahydro-1,3-benzodiazepin-3-yl)-piperidine-1-carboxylic acid {1-(7-methyl-1H-benzotriazol-5-ylmethyl)-2-[4-(1-methyl-piperidin-4-yl)-piperazin-1-yl]-2-oxo-ethyl}-amide,

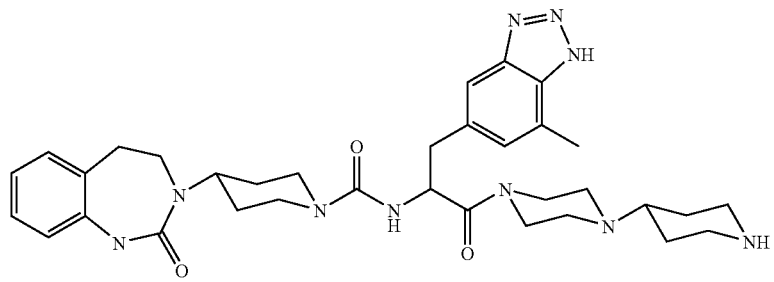

(192)

4-(2-oxo-1,2,4,5-tetrahydro-1,3-benzodiazepin-3-yl)-piperidine-1-carboxylic acid [1-(7-methyl-1H-benzotriazol-5-ylmethyl)-2-oxo-2-(4-piperidin-4-yl-piperazin-1-yl)-ethyl]-amide,

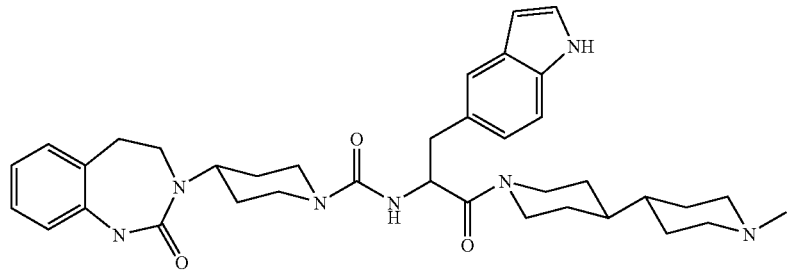

(193)

4-(2-oxo-1,2,4,5-tetrahydro-1,3-benzodiazepin-3-yl)-piperi-
dine-1-carboxylic acid [1-(1H-indol-5-ylmethyl)-2-(1'-
methyl-4,4'-bipiperidinyl-1-yl)-2-oxo-ethyl]-amide,

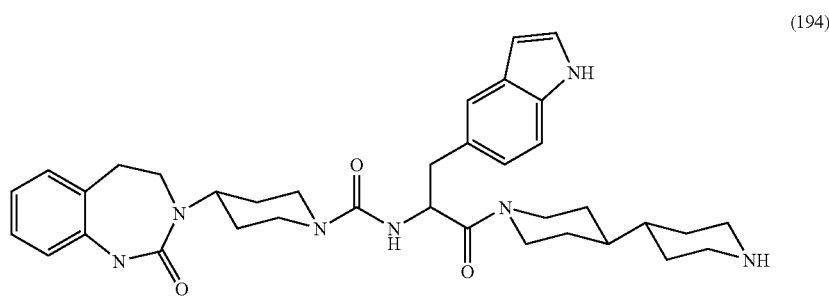
(194)

4-(2-oxo-1,2,4,5-tetrahydro-1,3-benzodiazepin-3-yl)-piperi-
dine-1-carboxylic acid [2-(4,4'-bipiperidinyl-1-yl)-1-(1H-
indol-5-ylmethyl)-2-oxo-ethyl]-amide,

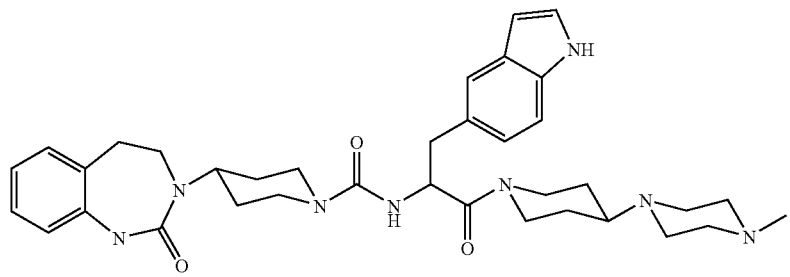
(195)

4-(2-oxo-1,2,4,5-tetrahydro-1,3-benzodiazepin-3-yl)-piperi-
dine-1-carboxylic acid {1-(1H-indol-5-ylmethyl)-2-[4-(4-
methyl-piperazin-1-yl)-piperidin-1-yl]-2-oxo-ethyl}-
amide,

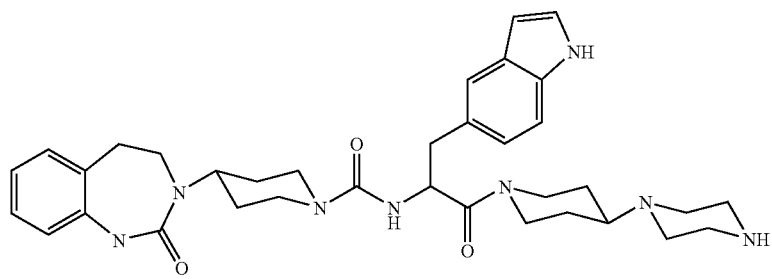
(196)

4-(2-oxo-1,2,4,5-tetrahydro-1,3-benzodiazepin-3-yl)-piperi-
   dine-1-carboxylic acid [1-(1H-indol-5-ylmethyl)-2-oxo-
   2-(4-piperazin-1-yl-piperidin-1-yl)-ethyl]-amide,

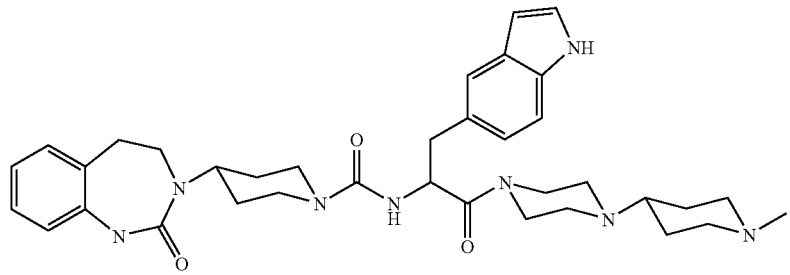

(197)

4-(2-oxo-1,2,4,5-tetrahydro-1,3-benzodiazepin-3-yl)-piperi-
   dine-1-carboxylic acid {1-(1H-indol-5-ylmethyl)-2-[4-(1-
   methyl-piperidin-4-yl)-piperazin-1-yl]-2-oxo-ethyl}-
   amide,

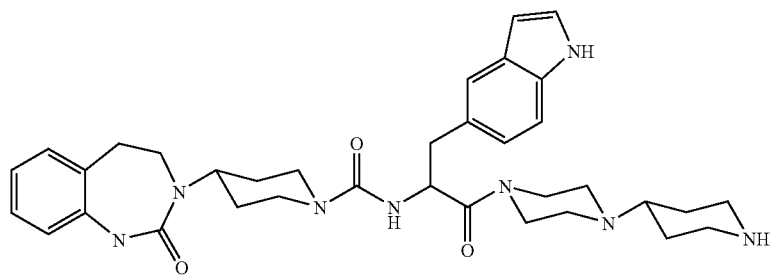

(198)

4-(2-oxo-1,2,4,5-tetrahydro-1,3-benzodiazepin-3-yl)-piperi-
   dine-1-carboxylic acid [1-(1H-indol-5-ylmethyl)-2-oxo-
   2-(4-piperidin-4-yl-piperazin-1-yl)-ethyl]-amide,

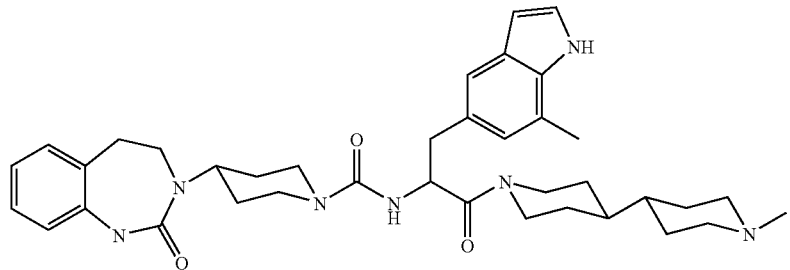

(199)

4-(2-oxo-1,2,4,5-tetrahydro-1,3-benzodiazepin-3-yl)-piperidine-1-carboxylic acid [2-(1'-methyl-4,4'-bipiperidinyl-1-yl)-1-(7-methyl-1H-indol-5-ylmethyl)-2-oxo-ethyl]-amide,

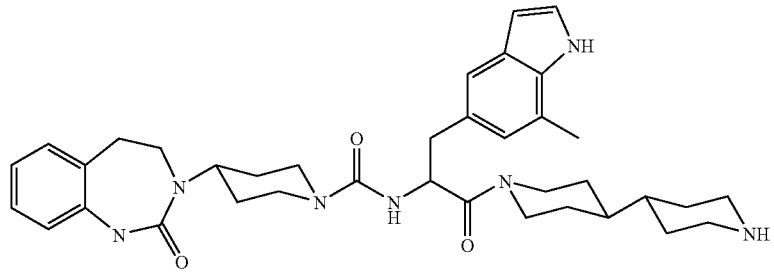

(200)

4-(2-oxo-1,2,4,5-tetrahydro-1,3-benzodiazepin-3-yl)-piperidine-1-carboxylic acid [2-(4,4'-bipiperidinyl-1-yl)-1-(7-methyl-1H-indol-5-ylmethyl)-2-oxo-ethyl]-amide,

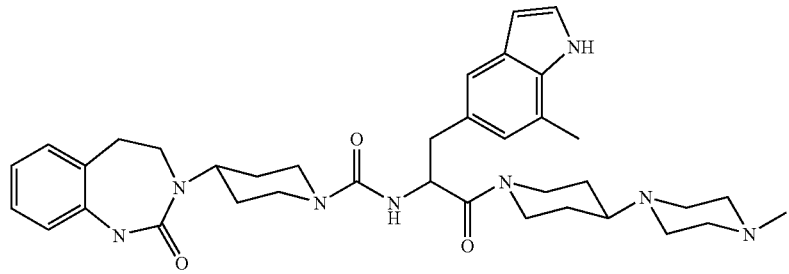

(201)

4-(2-oxo-1,2,4,5-tetrahydro-1,3-benzodiazepin-3-yl)-piperidine-1-carboxylic acid {1-(7-methyl-1H-indol-5-ylmethyl)-2-[4-(4-methyl-piperazin-1-yl)-piperidin-1-yl]-2-oxo-ethyl}-amide,

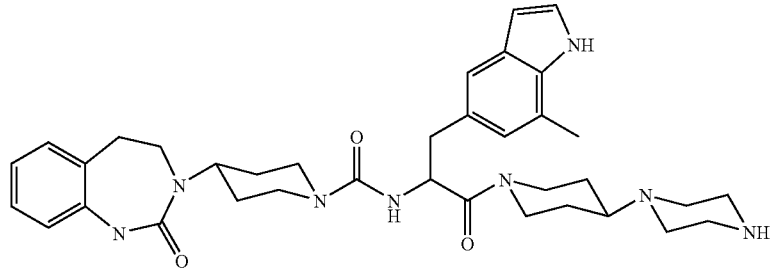

(202)

4-(2-oxo-1,2,4,5-tetrahydro-1,3-benzodiazepin-3-yl)-piperidine-1-carboxylic acid [1-(7-methyl-1H-indol-5-ylmethyl)-2-oxo-2-(4-piperazin-1-yl-piperidin-1-yl)-ethyl]-amide,

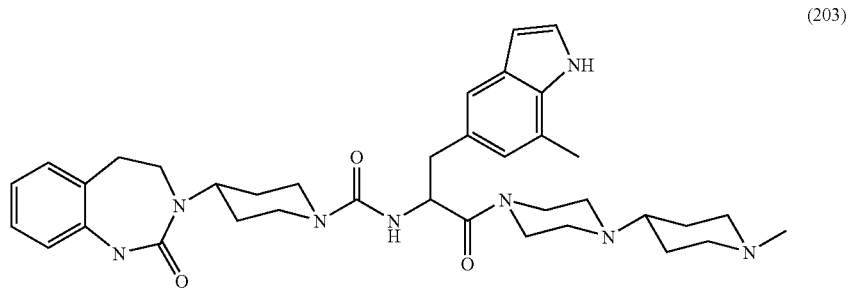

(203)

4-(2-oxo-1,2,4,5-tetrahydro-1,3-benzodiazepin-3-yl)-piperidine-1-carboxylic acid {1-(7-methyl-1H-indol-5-ylmethyl)-2-[4-(1-methyl-piperidin-4-yl)-piperazin-1-yl]-2-oxo-ethyl}-amide,

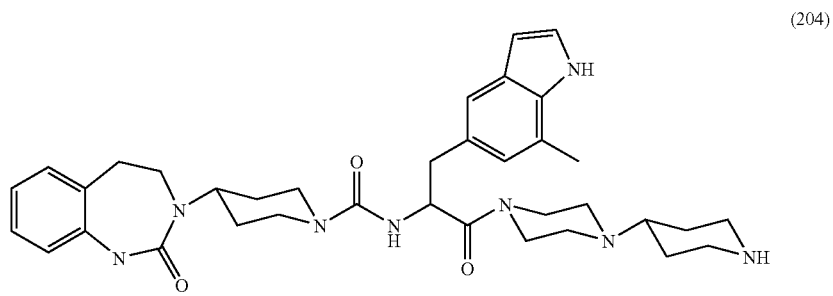

(204)

4-(2-oxo-1,2,4,5-tetrahydro-1,3-benzodiazepin-3-yl)-piperidine-1-carboxylic acid [1-(7-methyl-1H-indol-5-ylmethyl)-2-oxo-2-(4-piperidin-4-yl-piperazin-1-yl)-ethyl]-amide.

The following Examples describe the preparation of pharmaceutical formulations which contain as active substance any desired compound of general formula (I):

EXAMPLE I

Capsules for Powder Inhalation Containing 1 mg of Active Ingredient

Composition:

| 1 capsule for powder inhalation contains: | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

EXAMPLE II

Inhalable Solution for Respimat® Containing 1 mg of Active Ingredient

Composition:

| 1 puff contains: | |
|---|---|
| active ingredient | 1.0 mg |
| benzalkonium chloride | 0.002 mg |
| disodium edetate | 0.0075 mg |
| purified water ad | 15.0 μl |

Method of Preparation:

The active ingredient and benzalkonium chloride are dissolved in water and transferred into Respimat® cartridges.

EXAMPLE III

Inhalable Solution for Nebulisers Containing 1 mg of Active Ingredient

Composition:

| 1 vial contains: | |
| --- | --- |
| active ingredient | 0.1 g |
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

EXAMPLE IV

Propellant Gas-Operated Metering Aerosol Containing 1 mg of Active Ingredient

Composition:

| 1 puff contains: | |
| --- | --- |
| active ingredient | 1.0 mg |
| lecithin | 0.1% |
| propellant gas ad | 50.0 µl |

Method of Preparation:

The micronised active ingredient is homogeneously suspended in the mixture of lecithin and propellant gas. The suspension is transferred into a pressurised container with a metering valve.

EXAMPLE V

Nasal Spray Containing 1 mg of Active Ingredient

Composition:

| active ingredient | 1.0 mg |
| --- | --- |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

EXAMPLE VI

Injectable Solution Containing 5 mg of Active Substance Per 5 ml

Composition:

| active substance | 5 mg |
| --- | --- |
| glucose | 250 mg |
| human serum albumin | 10 mg |
| glycofurol | 250 mg |
| water for injections ad | 5 ml |

Preparation:

Glycofurol and glucose are dissolved in water for injections (Wfl); human serum albumin is added; active ingredient is dissolved with heating; made up to specified volume with Wfl; transferred into ampoules under nitrogen gas.

EXAMPLE VII

Injectable Solution Containing 100 mg of Active Substance Per 20 ml

Composition:

| active substance | 100 mg |
| --- | --- |
| monopotassium dihydrogen phosphate = $KH_2PO_4$ | 12 mg |
| disodium hydrogen phosphate = $Na_2HPO_4.2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

EXAMPLE VIII

Lyophilisate Containing 10 mg of Active Substance

Composition:

| Active substance | 10 mg |
| --- | --- |
| Mannitol | 300 mg |
| human serum albumin | 20 mg |
| water for injections ad | 2 ml |

Preparation:

Mannitol is dissolved in water for injections (Wfl); human serum albumin is added; active ingredient is dissolved with heating; made up to specified volume with Wfl; transferred into vials; freeze-dried.

| Solvent for lyophilisate: | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (Wfl); transferred into ampoules.

EXAMPLE IX

Tablets Containing 20 mg of Active Substance

Composition:

| active substance | 20 mg |
|---|---|
| lactose | 120 mg |
| maize starch | 40 mg |
| magnesium stearate | 2 mg |
| Povidone K 25 | 18 mg |

Preparation:

Active substance, lactose and maize starch are homogeneously mixed; granulated with an aqueous solution of Povidone; mixed with magnesium stearate; compressed in a tablet press; weight of tablet 200 mg.

EXAMPLE X

Capsules Containing 20 mg Active Substance

Composition:

| active substance | 20 mg |
|---|---|
| maize starch | 80 mg |
| highly dispersed silica | 5 mg |
| magnesium stearate | 2.5 mg |

Preparation:

Active substance, maize starch and silica are homogeneously mixed; mixed with magnesium stearate; the mixture is packed into size for 3 hard gelatine capsules in a capsule filling machine.

EXAMPLE XI

Suppositories Containing 50 mg of Active Substance

Composition:

| active substance | 50 mg |
|---|---|
| hard fat (*Adeps solidus*) q.s. ad | 1700 mg |

Preparation:

Hard fat is melted at about 38° C.; ground active substance is homogeneously dispersed in the molten hard fat; after cooling to about 35° C. it is poured into chilled moulds.

EXAMPLE XII

Injectable Solution Containing 10 mg of Active Substance Per 1 ml

Composition:

| active substance | 10 mg |
|---|---|
| mannitol | 50 mg |
| human serum albumin | 10 mg |
| water for injections ad | 1 ml |

Preparation:

Mannitol is dissolved in water for injections (Wfl); human serum albumin is added; active ingredient is dissolved with heating; made up to specified volume with Wfl; transferred into ampoules under nitrogen gas.

What is claimed is:

1. A compound of the formula (I)

wherein
  A denotes a nitrogen atom or a CH group,
  B denotes a nitrogen atom or a CH group,
  D denotes a hydrogen atom or a methyl group,
  E denotes a hydrogen, fluorine, chlorine or bromine atom, a methyl, ethyl or trifluoromethyl group,
  X denotes a methylene group,
  $R^1$ denotes a group of formula or and
  $R^2$ denotes a group of formula

,

-continued
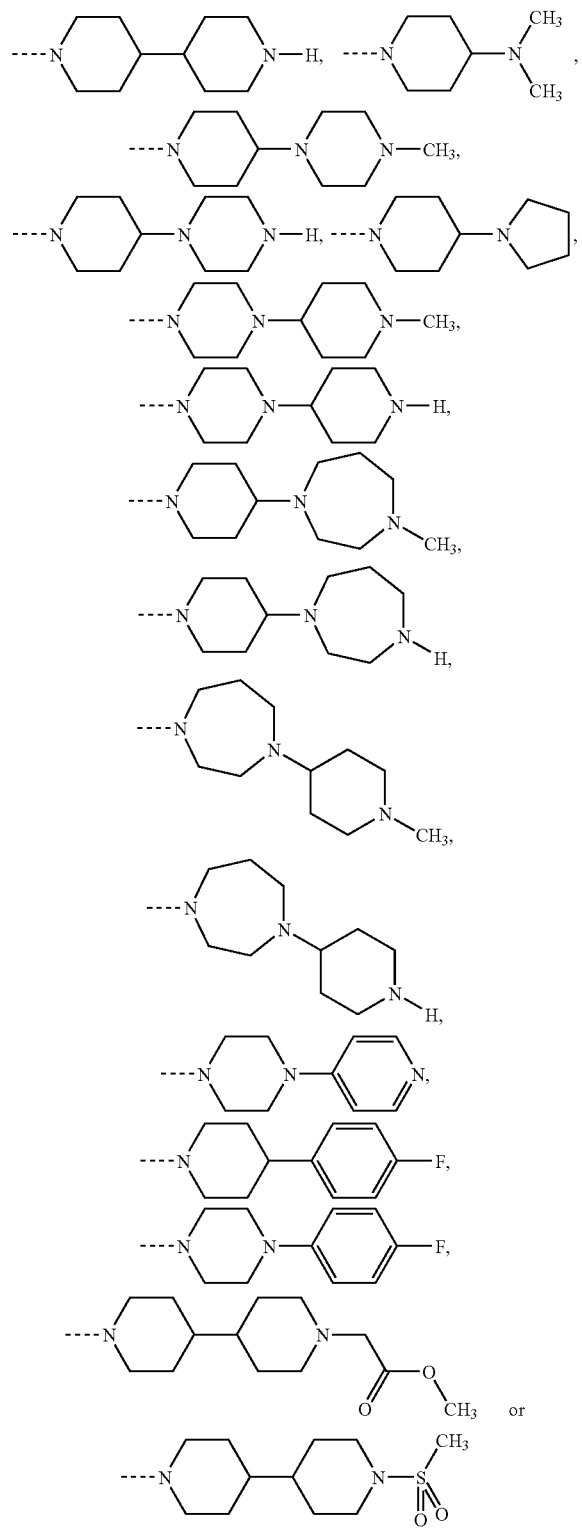
or a tautomer or pharmaceutically acceptable salt thereof.
2. A compound of the formula I according to claim 1, wherein
the combination of A, B, D and E denotes a group of formula
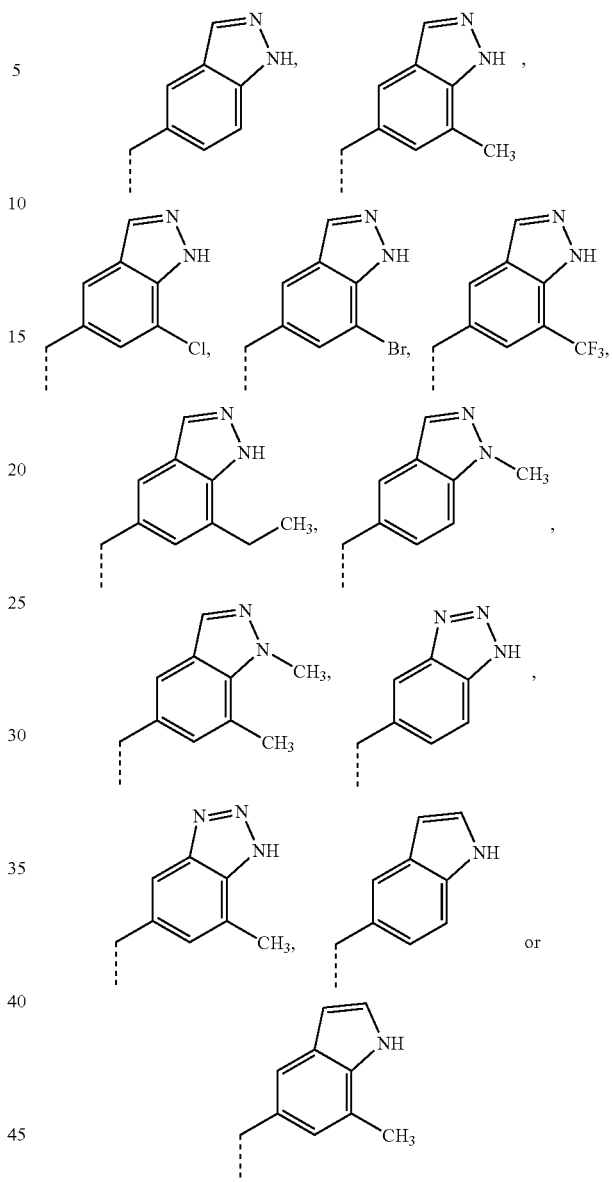
$R^1$ denotes a group of formula
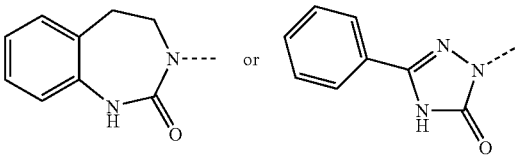
and
$R^2$ denotes a group of formula
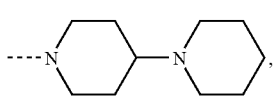

-continued

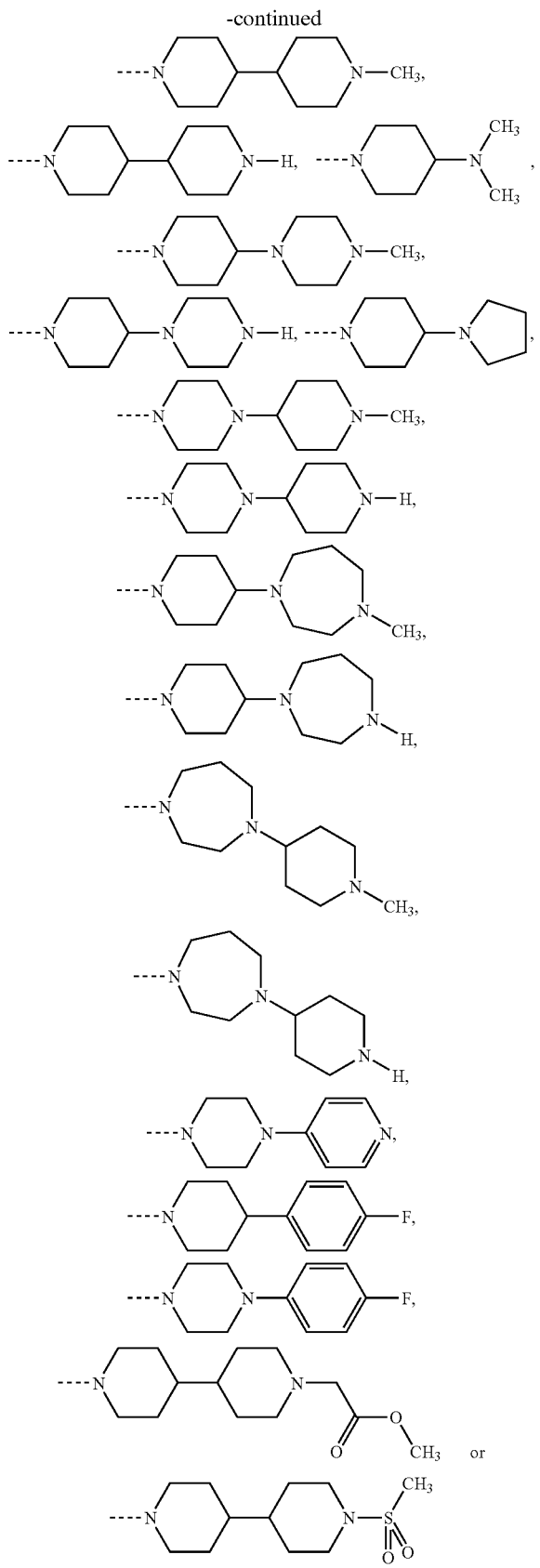

or a tautomer or pharmaceutically acceptable salt thereof.

3. A compound selected from the group consisting of:
(1) 1-(1,4'-bipiperidinyl-1'-yl)-2-(1H-indazol-5-ylmethyl)-4-[4-(2-oxo-1,2,4,5-tetrahydro-1,3-benzodiazepin-3-yl)-piperidin-1-yl]-butane-1,4-dione,
(2) 2-(1H-indazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione,
(3) 1-(4,4'-bipiperidinyl-1-yl)-2-(1H-indazol-5-ylmethyl)-4-[4-(2-oxo-1,2,4,5-tetrahydro-1,3-benzodiazepin-3-yl)-piperidin-1-yl]-butane-1,4-dione,
(4) 1-(4-dimethylamino-piperidin-1-yl)-2-(1H-indazol-5-ylmethyl)-4-[4-(2-oxo-1,2,4,5-tetrahydro-1,3-benzodiazepin-3-yl)-piperidin-1-yl]-butane-1,4-dione,
(5) (S)-2-(1H-indazol-5-yl methyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione,
(6) 2-(1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione,
(7) 2-(1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione,
(8) 2-(1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione,
(9) 2-(1H-indazol-5-ylmethyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butane-1,4-dione,
(10) 2-(1H-indazol-5-ylmethyl)-4-[4-(2-oxo-1,2,4,5-tetrahydro-1,3-benzodiazepin-3-yl)-piperidin-1-yl]-1-(4-perhydro-1,4-diazepin-1-yl-piperidin-1-yl)-butane-1,4-dione,
(11) 2-(1H-indazol-5-ylmethyl)-1-[4-(1-methyl-piperidin-4-yl)-perhydro-1,4-diazepin-1-yl]-4-[4-(2-oxo-1,2,4,5-tetrahydro-1,3-benzodiazepin-3-yl)-piperidin-1-yl]-butane-1,4-dione,
(12) 2-(1H-indazol-5-ylmethyl)-4-[4-(2-oxo-1,2,4,5-tetrahydro-1,3-benzodiazepin-3-yl)-piperidin-1-yl]-1-(4-piperidin-4-yl-perhydro-1,4-diazepin-1-yl)-butane-1,4-dione,
(13) 1-[4-(4-fluoro-phenyl)-piperazin-1-yl]-2-(1H-indazol-5-ylmethyl)-4-[4-(2-oxo-1,2,4,5-tetrahydro-1,3-benzodiazepin-3-yl)-piperidin-1-yl]-butane-1,4-dione,
(14) 1-[4-(4-fluoro-phenyl)-piperidin-1-yl]-2-(1H-indazol-5-ylmethyl)-4-[4-(2-oxo-1,2,4,5-tetrahydro-1,3-benzodiazepin-3-yl)-piperidin-1-yl]-butane-1,4-dione,
(15) 2-(1H-indazol-5-ylmethyl)-4-[4-(2-oxo-1,2,4,5-tetrahydro-1,3-benzodiazepin-3-yl)-piperidin-1-yl]-1-(4-pyridin-4-yl-piperazin-1-yl)-butane-1,4-dione,
(16) methyl (1'-{2-(1H-indazol-5-ylmethyl)-4-oxo-4-[4-(2-oxo-1,2,4,5-tetrahydro-1,3-benzodiazepin-3-yl)-piperidin-1-yl]-butyryl}-4,4'-bipiperidinyl-1-yl)-acetate,
(17) 2-(1H-indazol-5-ylmethyl)-1-(1'-methanesulphonyl-4,4'-bipiperidinyl-1-yl)-4-[4-(2-oxo-1,2,4,5-tetrahydro-1,3-benzodiazepin-3-yl)-piperidin-1-yl]-butane-1,4-dione,
(35) 1-(1,4'-bipiperidinyl-1'-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,
(36) 1-(1'-methyl-4,4'-bipiperidinyl-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(37) 1-(4,4'-bipiperidinyl-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(38) 1-(4-dimethylamino-piperidin-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(39) 2-(7-methyl-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione,

(40) 2-(7-methyl-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione,

(41) 2-(7-methyl-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione,

(42) 2-(7-methyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione,

(43) 2-(7-methyl-1H-indazol-5-ylmethyl)-1-[4-(4-methyl-perhydro-1,4-diazepin-1-yl)-piperidin-1-yl]-4-[4-(2-oxo-1,2,4,5-tetrahydro-1,3-benzodiazepin-3-yl)-piperidin-1-yl]-butane-1,4-dione,

(44) 2-(7-methyl-1H-indazol-5-ylmethyl)-4-[4-(2-oxo-1,2,4,5-tetrahydro-1,3-benzodiazepin-3-yl)-piperidin-1-yl]-1-(4-perhydro-1,4-diazepin-1-yl-piperidin-1-yl)-butane-1,4-dione,

(45) 2-(7-methyl-1H-indazol-5-ylmethyl)-1-[4-(1-methyl-piperidin-4-yl)-perhydro-1,4-diazepin-1-yl]-4-[4-(2-oxo-1,2,4,5-tetrahydro-1,3-benzodiazepin-3-yl)-piperidin-1-yl]-butane-1,4-dione,

(46) 2-(7-methyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-perhydro-1,4-diazepin-1-yl)-butane-1,4-dione,

(47) 1-[4-(4-fluoro-phenyl)-piperazin-1-yl]-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(48) 1-[4-(4-fluoro-phenyl)-piperidin-1-yl]-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(49) 2-(7-methyl-1H-indazol-5-ylmethyl)-4-[4-(2-oxo-1,2,4,5-tetrahydro-1,3-benzodiazepin-3-yl)-piperidin-1-yl]-1-(4-pyridin-4-yl-piperazin-1-yl)-butane-1,4-dione,

(50) methyl (1'-{2-(7-methyl-1H-indazol-5-ylmethyl)-4-oxo-4-[4-(2-oxo-1,2,4,5-tetrahydro-1,3-benzodiazepin-3-yl)-piperidin-1-yl]-butyryl}-4,4'-bipiperidinyl-1-yl)-acetate,

(51) 1-(1'-methanesulphonyl-4,4'-bipiperidinyl-1-yl)-2-(7-methyl-1H-indazol-5-ylmethyl)-4-[4-(2-oxo-1,2,4,5-tetrahydro-1,3-benzodiazepin-3-yl)-piperidin-1-yl]-butane-1,4-dione,

(69) 2-(1H-indazol-5-ylmethyl)-1-(1'-methyl-4,4'-bipiperidinyl-1-yl)-4-[4-(5-oxo-3-phenyl-4,5-dihydro-1,2,4-triazol-1-yl)-piperidin-1-yl]-butane-1,4-dione,

(70) 1-(4,4'-bipiperidinyl-1-yl)-2-(1H-indazol-5-ylmethyl)-4-[4-(5-oxo-3-phenyl-4,5-dihydro-1,2,4-triazol-1-yl)-piperidin-1-yl]-butane-1,4-dione,

(71) 2-(1H-indazol-5-ylmethyl)-1-[4-(4-methyl-piperazin-1-yl)-piperidin-1-yl]-4-[4-(5-oxo-3-phenyl-4,5-dihydro-1,2,4-triazol-1-yl)-piperidin-1-yl]-butane-1,4-dione,

(72) 2-(1H-indazol-5-ylmethyl)-4-[4-(5-oxo-3-phenyl-4,5-dihydro-1,2,4-triazol-1-yl)-piperidin-1-yl]-1-(4-piperazin-1-yl-piperidin-1-yl)-butane-1,4-dione,

(73) 2-(1H-indazol-5-ylmethyl)-1-[4-(1-methyl-piperidin-4-yl)-piperazin-1-yl]-4-[4-(5-oxo-3-phenyl-4,5-dihydro-1,2,4-triazol-1-yl)-piperidin-1-yl]-butane-1,4-dione,

(74) 2-(1H-indazol-5-ylmethyl)-4-[4-(5-oxo-3-phenyl-4,5-dihydro-1,2,4-triazol-1-yl)-piperidin-1-yl]-1-(4-piperidin-4-yl-piperazin-1-yl)-butane-1,4-dione,

(75) 1-(1,4'-bipiperidinyl-1'-yl)-2-(1H-indazol-5-ylmethyl)-4-[4-(5-oxo-3-phenyl-4,5-dihydro-1,2,4-triazol-1-yl)-piperidin-1-yl]-butane-1,4-dione,

(76) 1-(4-dimethylamino-piperidin-1-yl)-2-(1H-indazol-5-ylmethyl)-4-[4-(5-oxo-3-phenyl-4,5-dihydro-1,2,4-triazol-1-yl)-piperidin-1-yl]-butane-1,4-dione,

(85) 2-(7-ethyl-1H-indazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione,

(86) 1-(4,4'-bipiperidinyl-1-yl)-2-(7-ethyl-1H-indazol-5-ylmethyl)-4-[4-(2-oxo-1,2,4,5-tetrahydro-1,3-benzodiazepin-3-yl)-piperidin-1-yl]-butane-1,4-dione,

(87) 2-(7-ethyl-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione,

(88) 2-(7-ethyl-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione,

(89) 2-(7-ethyl-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione,

(90) 2-(7-ethyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione,

(91) 2-(7-chloro-1H-indazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione,

(92) 1-(4,4'-bipiperidinyl-1-yl)-2-(7-chloro-1H-indazol-5-ylmethyl)-4-[4-(2-oxo-1,2,4,5-tetrahydro-1,3-benzodiazepin-3-yl)-piperidin-1-yl]-butane-1,4-dione,

(93) 2-(7-chloro-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione,

(94) 2-(7-chloro-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione,

(95) 2-(7-chloro-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione,

(96) 2-(7-chloro-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione,

(97) 2-(7-bromo-1H-indazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione,

(98) 1-(4,4'-bipiperidinyl-1-yl)-2-(7-bromo-1H-indazol-5-ylmethyl)-4-[4-(2-oxo-1,2,4,5-tetrahydro-1,3-benzodiazepin-3-yl)-piperidin-1-yl]-butane-1,4-dione,

(99) 2-(7-bromo-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (100) 2-(7-bromo-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (101) 2-(7-bromo-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (102) 2-(7-bromo-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (103) 1-(1'-methyl-4,4'-bipiperidinyl-1-yl)-4-[4-(2-oxo-1,2,4,5-tetrahydro-1,3-benzodiazepin-3-yl)-piperidin-1-yl]-2-(7-trifluoromethyl-1H-indazol-5-ylmethyl)-butane-1,4-dione, (104) 1-(4,4'-bipiperidinyl-1-yl)-4-[4-(2-oxo-1,2,4,5-tetrahydro-1,3-benzodiazepin-3-yl)-piperidin-1-yl]-2-(7-trifluoromethyl-1H-indazol-5-ylmethyl)-butane-1,4-dione, (105) 2-(7-methyl-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, -oxo-1,2,4,5-tetrahydro-1,3-benzodiazepin-3-yl)-piperidin-1-yl]-butane-1,4-dione, (106) 4-[4-(2-oxo-1,2,4,5-tetrahydro-1,3-benzodiazepin-3-yl)-piperidin-1-yl]-1-(4-piperazin-1-yl-piperidin-1-yl)-2-(7-trifluoromethyl-1H-indazol-5-ylmethyl)-butane-1,4-dione, (107) 1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-2-(7-trifluoromethyl-1H-indazol-5-ylmethyl)-butane-1,4-dione, (108) 4-[4-(2-oxo-1,2,4,5-tetrahydro-1,3-benzodiazepin-3-yl)-piperidin-1-yl]-1-(4-piperidin-4-yl-piperazin-1-yl)-2-(7-trifluoromethyl-1H-indazol-5-ylmethyl)-butane-1,4-dione, (109) 1-(1'-methyl-4,4'-bipiperidinyl-1-yl)-2-(1-methyl-1H-indazol-5-ylmethyl)-4-[4-(2-oxo-1,2,4,5-tetrahydro-1,3-benzodiazepin-3-yl)-piperidin-1-yl]-butane-1,4-dione, (110) 1-(4,4'-bipiperidinyl-1-yl)-2-(1-methyl-1H-indazol-5-ylmethyl)-4-[4-(2-oxo-1,2,4,5-tetrahydro-1,3-benzodiazepin-3-yl)-piperidin-1-yl]-butane-1,4-dione, (111) 2-(1-methyl-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (112) 2-(1-methyl-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (113) 2-(1-methyl-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (114) 2-(1-methyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (115) 2-(1,7-dimethyl-1H-indazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione, (116) 1-(4,4'-bipiperidinyl-1-yl)-2-(1,7-dimethyl-1H-indazol-5-ylmethyl)-4-[4-(2-oxo-1,2,4,5-tetrahydro-1,3-benzodiazepin-3-yl)-piperidin-1-yl]-butane-1,4-dione, (117) 2-(1,7-dimethyl-1H-indazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (118) 2-(1,7-dimethyl-1H-indazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (119) 2-(1,7-dimethyl-1H-indazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (120) 2-(1,7-dimethyl-1H-indazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (121) 2-(1H-benzotriazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione, (122) 2-(1H-benzotriazol-5-ylmethyl)-1-(4,4'-bipiperidinyl-1-yl)-4-[4-(2-oxo-1,2,4,5-tetrahydro-1,3-benzodiazepin-3-yl)-piperidin-1-yl]-butane-1,4-dione, (123) 2-(1H-benzotriazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (124) 2-(1H-benzotriazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (125) 2-(1H-benzotriazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (126) 2-(1H-benzotriazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (127) 2-(7-methyl-1H-benzotriazol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione, (128) 1-(4,4'-bipiperidinyl-1-yl)-2-(7-methyl-1H-benzotriazol-5-ylmethyl)-4-[4-(2-oxo-1,2,4,5-tetrahydro-1,3-benzodiazepin-3-yl)-piperidin-1-yl]-butane-1,4-dione, (129) 2-(7-methyl-1H-benzotriazol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (130) 2-(7-methyl-1H-benzotriazol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (131) 2-(7-methyl-1H-benzotriazol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (132) 2-(7-methyl-1H-benzotriazol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (133) 2-(1H-indol-5-ylmethyl)-1-(1'-methyl-4,4'-bipiperidinyl-1-yl)-4-[4-(2-oxo-1,2,4,5-tetrahydro-1,3-benzodiazepin-3-yl)-piperidin-1-yl]-butane-1,4-dione, (134) 1-(4,4'-bipiperidinyl-1-yl)-2-(1H-indol-5-ylmethyl)-4-[4-(2-oxo-1,2,4,5-tetrahydro-1,3-benzodiazepin-3-yl)-piperidin-1-yl]-butane-1,4-dione, (135) 2-(1H-indol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (136) 2-(1H-indol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (137) 2-(1H-indol-5-ylmethyl)-1-[4-(1-methyl-piperidin-4-yl)-piperazin-1-yl]-4-[4-(2-oxo-1,2,4,5-tetrahydro-1,3-benzodiazepin-3-yl)-piperidin-1-yl]-butane-1,4-dione, (138) 2-(1H-indol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, (139) 1-(1'-methyl-4,4'-bipiperidinyl-1-yl)-2-(7-methyl-1H-indol-5-ylmethyl)-4-[4-(2-oxo-1,2,4,5-tetrahydro-1,3-benzodiazepin-3-yl)-piperidin-1-yl]-butane-1,4-dione, (140) 1-(4,4'-bipiperidinyl-1-yl)-2-(7-methyl-1H-indol-5-ylmethyl)-4-[4-(2-oxo-1,2,4,5-tetrahydro-1,3-benzodiazepin-3-yl)-piperidin-1-yl]-butane-1,4-dione, (141) 2-(7-methyl-1H-indol-5-ylmethyl)-1-[4-(4-methyl-piperazin-1-yl)-piperidin-1-yl]-4-[4-(2-oxo-1,2,4,5-tetrahydro-1,3-benzodiazepin-3-yl)-piperidin-1-yl]-butane-1,4-dione, (142) 2-(7-methyl-1H-indol-5-ylmethyl)-4-[4-(2-oxo-1,2,4,5-tetrahydro-1,3-benzodiazepin-3-yl)-piperidin-1-yl]-1-(4-piperazin-1-yl-piperidin-1-yl)-butane-1,4-dione, (143) 2-(7-methyl-1H-indol-5-ylmethyl)-1-[4-(1-methyl-piperidin-4-yl)-piperazin-1yl]-4-[4-(2-oxo-1,2,4,5-tetrahydro-1,3-benzodiazepin-3-yl)-piperidin-1-yl]-butane-1,4-dione, (144) 2-(7-methyl-1H-indol-5-ylmethyl)-4-[4-(2-oxo-1,2,4,5-tetrahydro-1,3-benzodiazepin-3-yl)-piperidin-1-yl]-1-(4-piperidin-4-yl-piperazin-1-yl)-butane-1,4-dione, or a tautomer or pharmaceutically acceptable salt thereof.

4. A pharmaceutical composition comprising a compound according to claim 1, 2 or 3 together with one or more inert carriers and/or diluents.

5. A method for treating headaches which comprises administering a therapeutically effective amount of a compound according to claim 1, 2 or 3.

* * * * *